(12) United States Patent
Weinstein et al.

(10) Patent No.: US 11,813,065 B2
(45) Date of Patent: Nov. 14, 2023

(54) SYSTEMS, DEVICES, AND METHODS FOR CARDIAC DIAGNOSIS AND/OR MONITORING

(71) Applicant: ZOLL Medical Israel Ltd., Kfar-Saba (IL)

(72) Inventors: Uriel Weinstein, Mazkeret Batya (IL); Rafi Ravid, Savyon (IL); David Meshulam, Hod Hasharon (IL); Vered Cohen Sharvit, Modiin (IL); Arkadi Averboukh, Rehovot (IL); Jacob Hecht, Kfar Hess (IL)

(73) Assignee: ZOLL Medical Israel Ltd., Kfar saba (IL)

( * ) Notice: Subject to any disclaimer, the term of this patent is extended or adjusted under 35 U.S.C. 154(b) by 359 days.

(21) Appl. No.: 17/083,472

(22) Filed: Oct. 29, 2020

(65) Prior Publication Data

US 2021/0121090 A1 Apr. 29, 2021

Related U.S. Application Data

(60) Provisional application No. 62/927,428, filed on Oct. 29, 2019.

(51) Int. Cl.
*A61B 5/00* (2006.01)
*A61B 5/363* (2021.01)
(Continued)

(52) U.S. Cl.
CPC ............ *A61B 5/363* (2021.01); *A61B 5/0006* (2013.01); *A61B 5/25* (2021.01); *A61B 5/316* (2021.01); *A61B 5/6833* (2013.01); *A61B 5/7267* (2013.01)

(58) Field of Classification Search
CPC ......... A61B 5/0006; A61B 5/25; A61B 5/257; A61B 5/282; A61B 5/316; A61B 5/363;
(Continued)

(56) References Cited

U.S. PATENT DOCUMENTS 6,253,099 B1 6/2001 Oskin et al.
7,212,850 B2 5/2007 Prystowsky et al.
(Continued)

FOREIGN PATENT DOCUMENTS

| EP | 2030565 A1 | 4/2009 |
|---|---|---|
| WO | 2012011066 A1 | 1/2012 |
| WO | 2016115175 A1 | 7/2016 |

OTHER PUBLICATIONS

"ZOLL Introduces New Technology to Improve the Management of Acute Heart Failure Patients", News Release, Jun. 10, 2019, 2 pages.

*Primary Examiner* — George Manuel
(74) *Attorney, Agent, or Firm* — THE WEBB LAW FIRM

(57) ABSTRACT

Some embodiments of the current disclosure are directed toward cardiac diagnosis and/or arrhythmia monitoring, and more particularly, systems, devices and methods for arrhythmia monitoring with a trained classifier including at least one neural network. In some embodiments, an external heart monitoring device may include a plurality ECG electrodes to sense surface ECG activity, ECG processing circuitry to process the surface ECG activity to provide at least one ECG signal, a non-transitory computer-readable medium comprising a rhythm change classifier comprising at least one neural network, and at least one processor to receive the ECG signal(s), detect with the rhythm change classifier time data corresponding to a predetermined rhythm change in the ECG signal(s), determine based on the detected time data at least one ECG signal portion corresponding to the prede-
(Continued)

termined rhythm change, and transmit the at least one determined ECG signal portion to a remote computer system.

26 Claims, 30 Drawing Sheets

(51) Int. Cl.
*A61B 5/25* (2021.01)
*A61B 5/316* (2021.01)

(58) Field of Classification Search
CPC .... A61B 5/6805; A61B 5/6833; A61B 5/7267
See application file for complete search history.

(56) References Cited

U.S. PATENT DOCUMENTS

| | | |
|---|---|---|
| 7,715,905 B2 | 5/2010 | Kurzweil et al. |
| 8,945,019 B2 | 2/2015 | Prystowsky et al. |
| 8,983,587 B2 | 3/2015 | Kurzweil et al. |
| 9,179,851 B2 | 11/2015 | Baumann et al. |
| 9,788,752 B2 | 10/2017 | Weinstein et al. |
| 10,548,485 B2 | 2/2020 | Arditi et al. |
| 2008/0214946 A1 | 9/2008 | Miller et al. |
| 2011/0130800 A1 | 6/2011 | Weinstein et al. |
| 2016/0135706 A1 | 5/2016 | Sullivan et al. |
| 2018/0116537 A1* | 5/2018 | Sullivan ................. A61N 1/046 |
| 2018/0116598 A1 | 5/2018 | Lee et al. |
| 2019/0046038 A1 | 2/2019 | Weinstein et al. |
| 2019/0051393 A1 | 2/2019 | Whiting et al. |
| 2019/0059763 A1* | 2/2019 | Shakur ................... G16H 40/67 |
| 2019/0090769 A1 | 3/2019 | Boleyn et al. |
| 2019/0164134 A1 | 5/2019 | Morrow et al. |

* cited by examiner

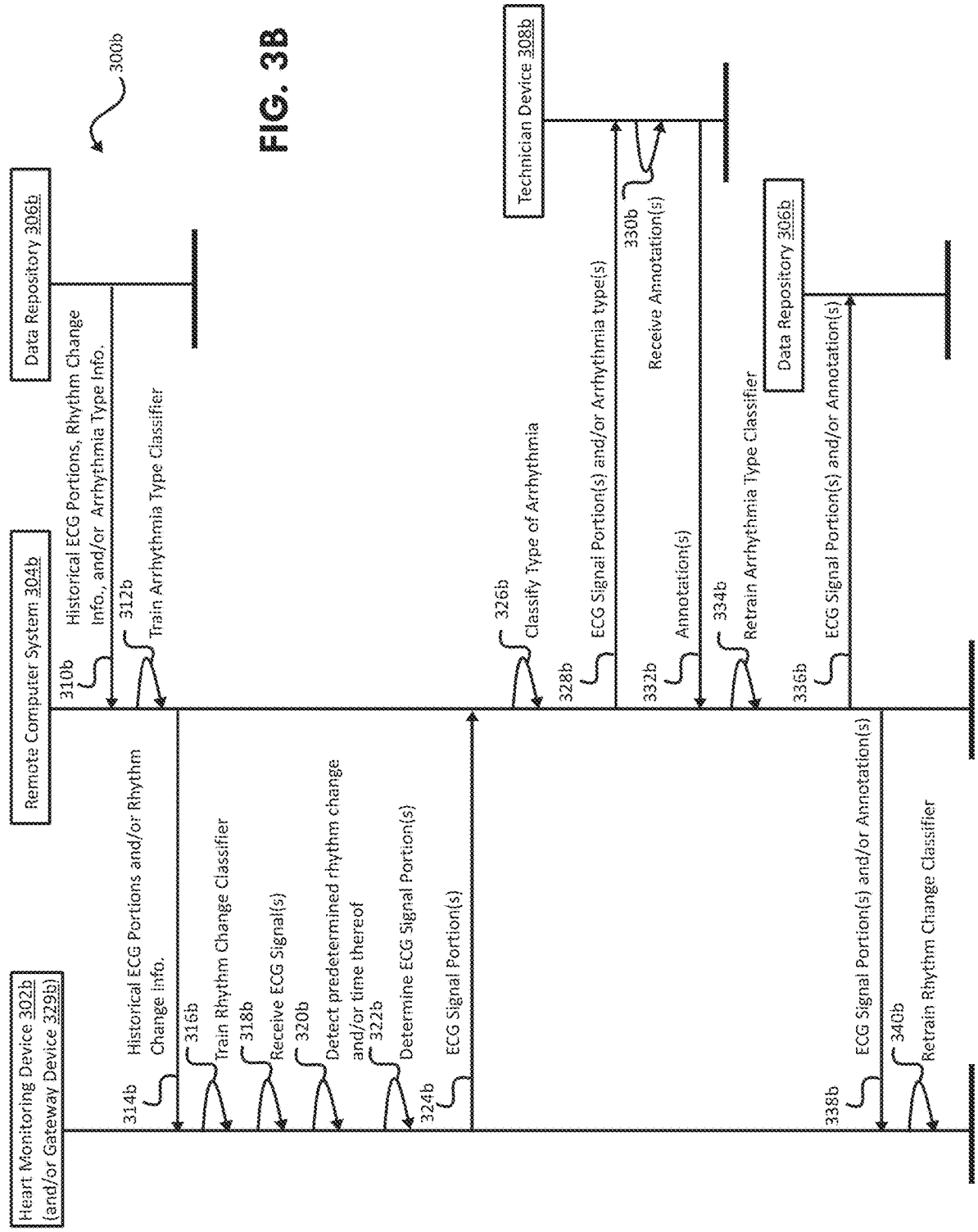

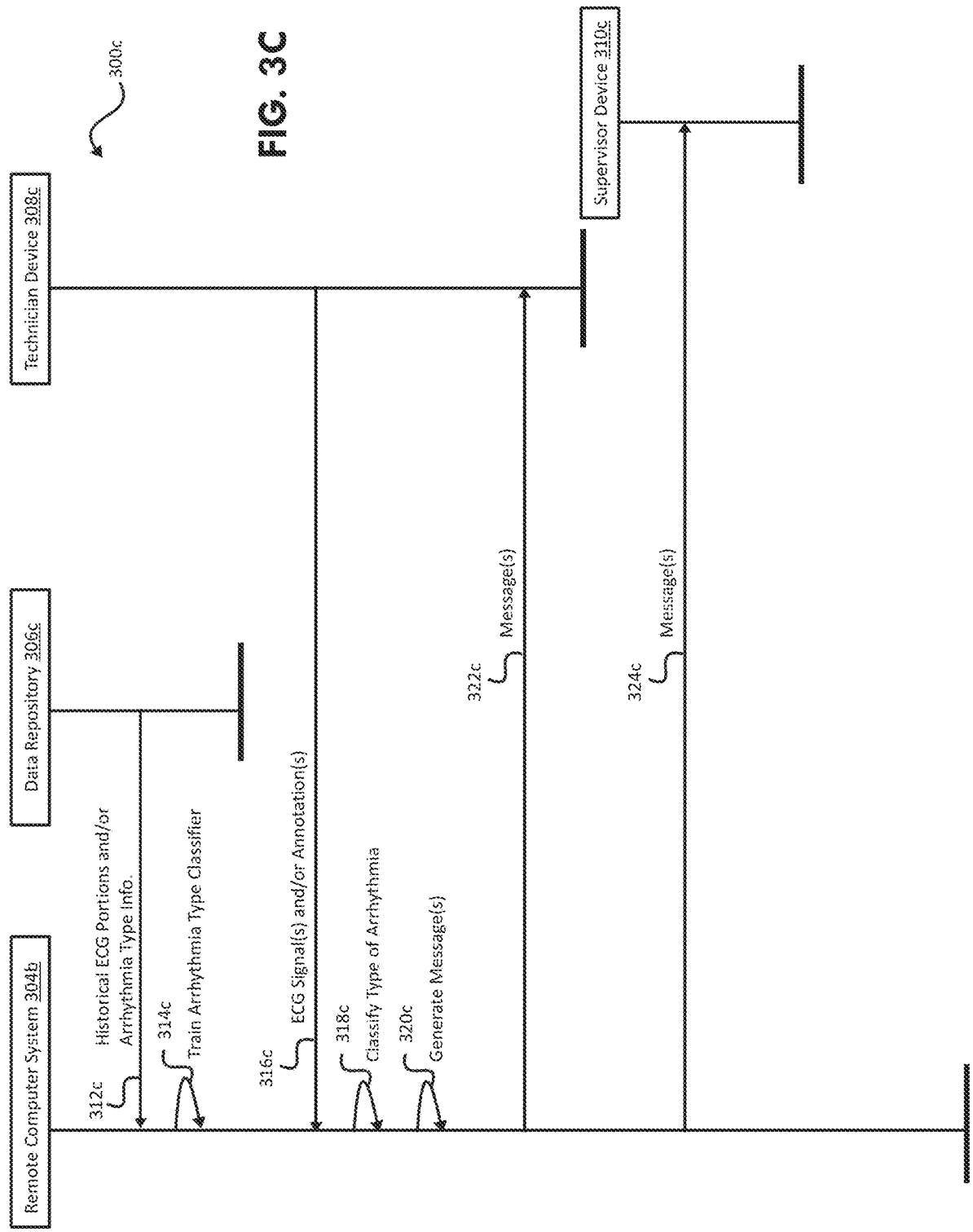

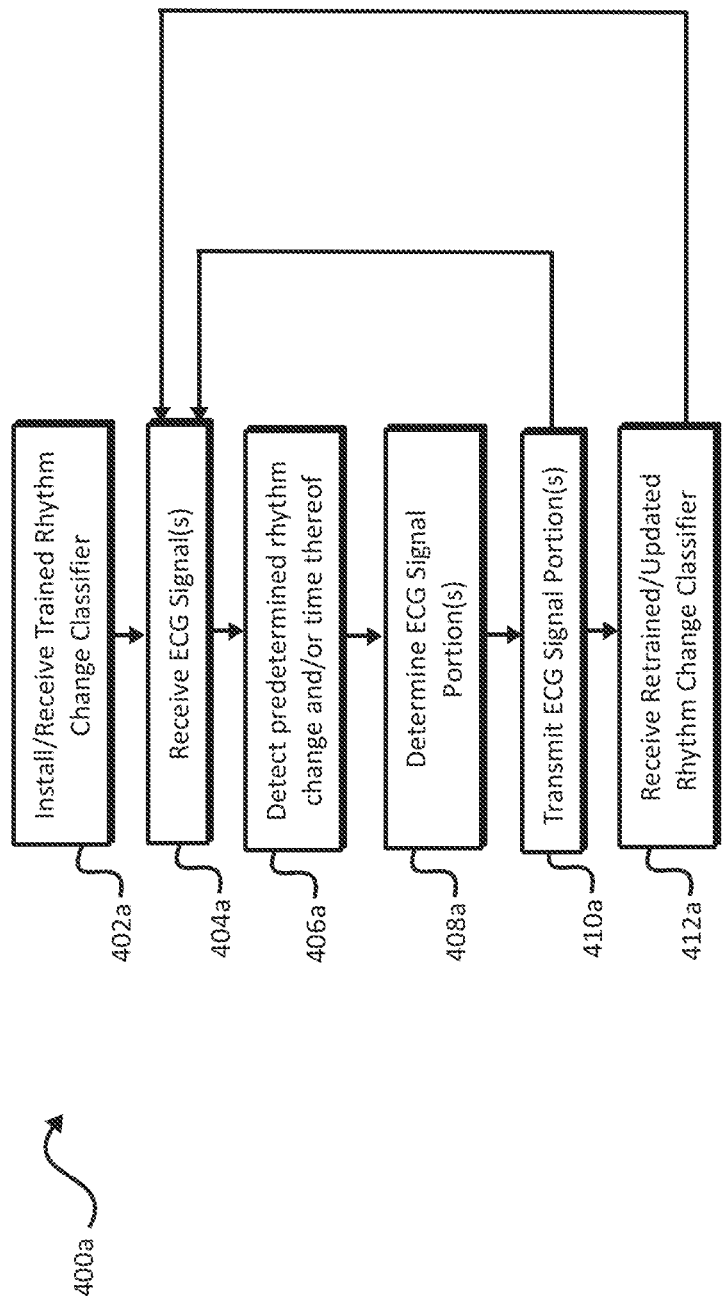

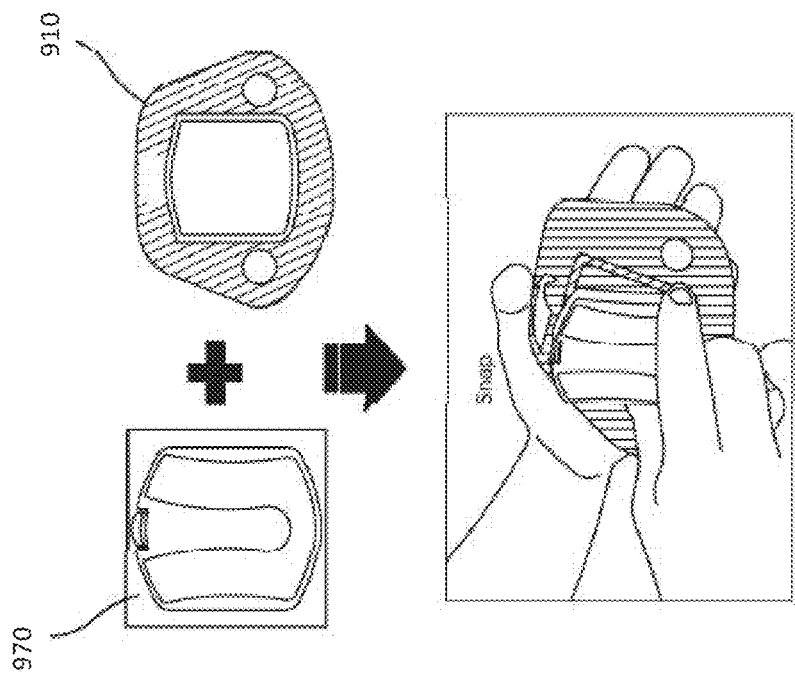
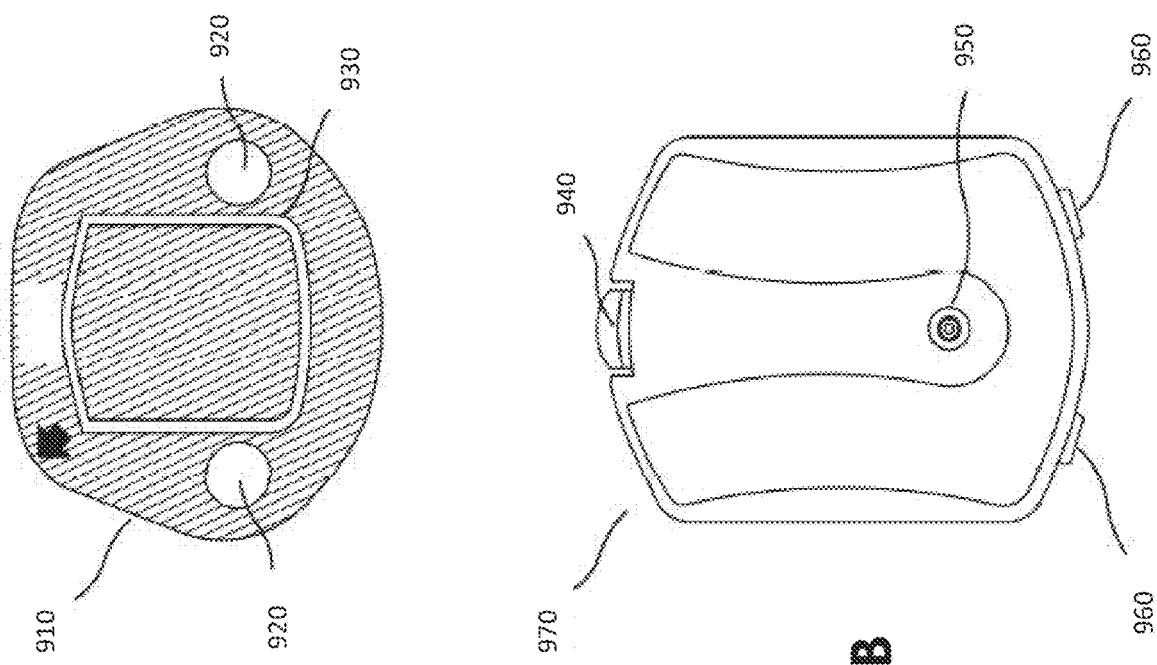
FIG. 9A  FIG. 9B  FIG. 9C

SYSTEMS, DEVICES, AND METHODS FOR CARDIAC DIAGNOSIS AND/OR MONITORING

CROSS REFERENCE TO RELATED APPLICATION

The present application claims the benefit of U.S. Provisional Patent Application No. 62/927,428, filed Oct. 29, 2019, the disclosure of which is hereby incorporated by reference in its entirety.

FIELD OF THE DISCLOSURE

Embodiments of the current disclosure are directed toward cardiac diagnosis and/or monitoring, and more particularly, systems, devices and methods for arrhythmia monitoring with a trained classifier including at least one neural network.

BACKGROUND OF THE DISCLOSURE

There is a wide variety of electronic and mechanical devices for monitoring and/or treating patients' medical conditions. In some examples, depending on the underlying medical condition being monitored and/or treated, medical devices such as cardiac monitors or defibrillators may be surgically implanted or externally connected to the patient. In some cases, physicians may use medical devices alone or in combination with drug therapies to treat conditions such as cardiac arrhythmias.

Such patients can include heart failure patients, e.g., congestive heart failure (CHF) patients. CHF is a condition in which the heart's function as a pump is inadequate to meet the body's needs. Generally, many disease processes can impair the pumping efficiency of the heart to cause congestive heart failure. The symptoms of congestive heart failure vary, but can include fatigue, diminished exercise capacity, shortness of breath, and swelling (edema). The diagnosis of congestive heart failure is based on knowledge of the individual's medical history, a careful physical examination, and selected laboratory tests.

Additionally or alternatively, patients can suffer from cardiac arrhythmias One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, e.g., by providing a therapeutic shock to the heart in an attempt to restore normal rhythm. To treat conditions such as bradycardia, an implanted or external pacing device can provide pacing stimuli to the patient's heart until intrinsic cardiac electrical activity returns. External pacemakers, defibrillators and other medical monitors designed for ambulatory and/or long-term use have further improved the ability to timely detect and treat life-threatening conditions. Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

Certain cardiac monitoring and/or treatment devices may communicate biometric data (e.g., ECG signal samples and/or ECG signal portions/strips) associated with the patient to the cloud (e.g., to a remote server, a cardiac monitoring facility, and/or the like) for review (e.g., by technicians, prescribers/treating physicians, and/or the like). However, such communication may require large bandwidth (e.g., all measured biometric data constantly streaming in real time and/or the like), may include a large amount of biometric data not associated with a cardiac event (e.g., biometric data associated with normal sinus rhythm (NSR) and/or the like), and may require human reviewers to review the large amounts of data without guidance as to which portions thereof are associated with cardiac events. Additionally or alternatively, it may be difficult to accurately determine whether a human reviewer correctly identified and/or annotated cardiac events in the biometric data. For example, technicians may be different levels of experience and expertise, and failing to identify a cardiac event and/or falsely identifying a cardiac event may result in harm to the patient (e.g., failure to provide needed treatment and/or providing treatment that is unnecessary, respectively).

SUMMARY OF SOME OF THE EMBODIMENTS

Embodiments of the current disclosure include an arrhythmia monitoring system. In some embodiments, the arrhythmia monitoring system may include an external heart monitoring device for a patient. The external heart monitoring device may include a plurality of electrocardiogram (ECG) electrodes configured to sense surface ECG activity of the patient, ECG processing circuitry configured to process the surface ECG activity of the patient to provide at least one ECG signal for the patient on at least one ECG channel, a non-transitory computer-readable medium including a rhythm change classifier, and at least one processor operatively connected to the at least one ECG channel and the non-transitory computer-readable medium. In some embodiments, the rhythm change classifier may include at least one neural network trained based on a historical collection of a plurality of ECG signal portions with known rhythm change information. In some embodiments, the at least one processor may be configured to receive the at least one ECG signal received via the at least one ECG channel; detect with the rhythm change classifier time data corresponding to a predetermined rhythm change in the at least one ECG signal, the time data comprising at least one of a start time, a time interval, or any combination thereof; determine based on the detected time data at least one ECG signal portion associated with the detected time data corresponding to the predetermined rhythm change in the at least one ECG signal; and transmit the at least one determined ECG signal portion to a remote computer system.

In some embodiments, the predetermined rhythm change may be associated with an arrhythmia.

In some embodiments, the non-transitory computer readable medium may include at least one of a memory, a programmable circuit board, a field programmable gate array, an integrated circuit, or any combination thereof. In some embodiments, the at least one neural network may include at least one of a convolutional neural network, a recurrent neural network, an attention network, a fully connected neural network, or any combination thereof.

In some embodiments, the at least one neural network may include at least one convolutional neural network having a plurality of convolutional layers. Additionally or alternatively, the plurality of convolutional layers may include at least seven convolutional layers and no more than ten convolutional layers. Additionally or alternatively, the at least one convolutional network may further include an input layer and an output layer.

In some embodiments, the at least one ECG signal may include a plurality of ECG signal samples. Additionally or alternatively, the input layer may include at least one node for each ECG signal sample of the plurality of ECG signal samples. In some embodiments, an output of the output layer may include an indication of the time data corresponding to the rhythm change.

In some embodiments, the at least one ECG signal portion may include an ECG signal portion having a duration greater than or equal to 15 seconds and less than or equal to 120 seconds. For example, the ECG signal portion may have a duration greater than or equal to 15 seconds and less than or equal to 60 seconds.

In some embodiments, the at least one ECG signal may include a plurality of ECG signal samples. Additionally or alternatively, the plurality of ECG signal samples may be sampled at a rate greater than or equal to 100 Hz and less than or equal to 500 Hz.

In some embodiments, the plurality of ECG signal samples may sampled at a rate greater than 100 Hz and less than 500 Hz.

In some embodiments, the at least one ECG channel may include a plurality of ECG channels. Additionally or alternatively, the at least one ECG signal may include at least one respective ECG signal associated with each respective ECG channel of the plurality of ECG channels. In some embodiments, the plurality of ECG channels may include a first ECG channel and a second ECG channel. Additionally or alternatively, the at least one ECG signal may include a first respective ECG signal associated with the first ECG channel and a second respective ECG signal associated with the second ECG channel. In some embodiments, the first respective ECG signal may be orthogonal to the second respective ECG signal.

In some embodiments, the at least one neural network may include a plurality of Siamese branches. Additionally or alternatively, each respective Siamese branch of the plurality of Siamese branches may be associated with a respective ECG channel of the plurality of ECG channels. In some embodiments, the at least one neural network may further include at least one further layer connected to the plurality of Siamese branches. In some embodiments, each Siamese branch of the plurality of Siamese branches may include a plurality of convolutional layers. Additionally or alternatively, dimensions of each of the plurality of convolutional layers of each respective Siamese branch may be the same as the dimensions of each of the plurality of convolutional layers of each other Siamese branch.

In some embodiments, the processor may be further configured to detect with the rhythm change classifier the predetermined rhythm change based on the at least one ECG signal.

In some embodiments, at least one sensor and associated sensor circuitry may be configured to sense non-ECG biometric data of the patient. Additionally or alternatively, detecting the predetermined rhythm change may be further based on the non-ECG biometric data of the patient. In some embodiments, the at least one sensor may include at least one of an accelerometer, a heart sound detector, or a combination thereof. Additionally or alternatively, the non-ECG biometric data may include at least one of acceleration data, heart sound data, or any combination thereof.

In some embodiments, detecting the predetermined rhythm change may be further based on at least one baseline ECG signal portion of the patient. Additionally or alternatively, detecting the predetermined rhythm change may be further based on at least one reference vector of the patient.

In some embodiments, detecting the predetermined rhythm change may be further based on at least one calibration measurement of the patient. Additionally or alternatively, the at least one calibration measurement may be based on at least one second ECG signal from second surface ECG activity sensed by a second plurality of ECG electrodes. Additionally or alternatively, the second plurality of ECG electrodes may be independent of the plurality of ECG electrodes of the external heart monitoring device.

In some embodiments, detecting the predetermined rhythm change may be further based at least one previous ECG signal portion.

In some embodiments, a gateway device may be included. Additionally or alternatively, transmitting the at least one determined ECG signal portion to the remote computer system may include transmitting the at least one determined ECG signal portion from the external heart monitoring device to the gateway device. Additionally or alternatively, the gateway device may be configured to receive the at least one determined ECG signal portion from the external heart monitoring device and transmit the at least one determined ECG signal portion to the remote server.

In some embodiments, the remote computer system may be in communication with the external heart monitoring device. Additionally or alternatively, the remote computer system may be configured to receive the at least one determined ECG signal portion from the external heart monitoring device and/or analyze the at least one determined ECG signal portion to classify a type of arrhythmia for the rhythm change in the at least one ECG signal. In some embodiments, the type of arrhythmia may include at least one of a change in heart rate, atrial fibrillation, flutter, supraventricular tachycardia, ventricular tachycardia, pause, AV block, ventricular fibrillation, bigeminy, trigeminy, ventricular ectopic beats, bradycardia, tachycardia, a change in morphology of the at least one ECG signal, or any combination thereof.

In some embodiments, the remote computer system may include an arrhythmia type classifier including at least one second neural network trained based on a second historical collection of a second plurality of ECG signal portions with known arrhythmia type information. Additionally or alternatively, analyzing the at least one determined ECG signal portion may include detecting with the arrhythmia type classifier the type of arrhythmia associated with the rhythm change based on the at least one determined ECG signal portion.

In some embodiments, the remote computer system may be further configured to transmit at least one message associated with the at least one determined ECG signal portion and the type of arrhythmia associated with the rhythm change to a computing device associated with a technician.

In some embodiments, the remote computer system may be further configured to analyze the at least one determined ECG signal portion to identify a rare arrhythmia for the rhythm change in the at least one ECG signal.

In some embodiments, the processor may be further configured to determine with the rhythm change classifier a confidence score associated with the predetermined rhythm change based on the at least one ECG signal.

In some embodiments, the processor may be further configured to transmit at least one second ECG signal portion of the at least one ECG signal to the remote computer system. Additionally or alternatively, the at least one second ECG signal portion may be independent of the detected time data corresponding to the predetermined rhythm change in the at least one ECG signal. In some embodiments, the processor may be further configured to randomly determine the at least one second ECG signal portion. In some embodiments, the processor may be further configured to determine with the rhythm change classifier a first confidence score associated with the predetermined rhythm change based on the at least one ECG signal, wherein the first confidence score is above a first threshold. Additionally or alternatively, the processor may be further configured to detect with the rhythm change classifier second time data corresponding to a potential rhythm change in the at least one ECG signal. Additionally or alternatively, the processor may be further configured to determine with the rhythm change classifier a second confidence score associated with the potential rhythm change based on the at least one ECG signal, wherein the second confidence score is below the first threshold and above a second threshold. Additionally or alternatively, the processor may be further configured to determine based on the detected second time data the at least one second ECG signal portion associated with the detected second time data corresponding to the potential rhythm change in the at least one ECG signal.

In some embodiments, the remote computer system is further configured to transmit at least one message associated with the at least one second ECG signal portion to a computing device associated with a technician and/or receive from the computing device associated with the technician annotation data associated with at least one annotation for the at least one second ECG signal portion.

In some embodiments, the remote computer system may be further configured to transmit the at least one annotation for the at least one second ECG signal portion to the external heart monitoring device. Additionally or alternatively, the processor may be further configured to retrain the rhythm change classifier based on the at least one second ECG signal portion and the annotation data.

In some embodiments, the remote computer system may be further configured to add the at least one second ECG signal portion to the historical collection of the plurality of ECG signal portions. Additionally or alternatively, the known rhythm change information for the at least one second ECG signal portion may include at least a portion of the annotation data. Additionally or alternatively, the remote computer system may be further configured to train an updated rhythm change classifier based on the historical collection of the plurality of ECG signal portions with the known rhythm change information. the remote computer system may be further configured to transmit the updated rhythm change classifier to the external heart monitoring device. Additionally or alternatively, the processor may be further configured to replace the rhythm change classifier with the updated rhythm change classifier.

In some embodiments, the remote computer system may include an arrhythmia type classifier comprising at least one second neural network trained based on a second historical collection of a second plurality of ECG signal portions with known arrhythmia type information. Additionally or alternatively, the remote computer system may be further configured to add the at least one second ECG signal portion to the second historical collection of the second plurality of ECG signal portions. Additionally or alternatively, the known arrhythmia type information for the at least one second ECG signal portion comprises at least a portion of the annotation data. Additionally or alternatively, the remote computer system may be further configured to retrain the arrhythmia type classifier based on the second historical collection of the second plurality of ECG signal portions with known arrhythmia type information.

In some embodiments, the at least one determined ECG signal portion may include a plurality of determined ECG signal portions. Additionally or alternatively, the remote computer system may be in communication with the external heart monitoring device. Additionally or alternatively, the remote computer system may be configured to receive the plurality of determined ECG signal portions from the external heart monitoring device and/or analyze each respective determined ECG signal portion of the plurality of determined ECG signal portions to classify a respective class for each respective determined ECG signal portion. Additionally or alternatively, the class for at least two respective determined ECG signal portions may include a first class. In some embodiments, the remote computer system may be further configured to transmit at least one message associated with the at least two respective determined ECG signal portions and the first class to a computing device associated with a technician.

In some embodiments, the processor may be further configured to detect with the rhythm change classifier at least one of a count of peaks or a heart rate based on the at least one ECG signal. Additionally or alternatively, the processor may be further configured to determine the detected at least one of the count of peaks or the heart rate is above a first threshold for the patient or below a second threshold for the patient. Additionally or alternatively, the second threshold for the patient may be less than the first threshold for the patient. Additionally or alternatively, the processor may be further configured to detect the predetermined rhythm change based on the at least one of the count of peaks or the heart rate being above the first threshold for the patient or below the second threshold for the patient.

In some embodiments, the historical collection of the plurality of ECG signal portions may include a second plurality of ECG signal portions of at least one second ECG signal based on second surface ECG activity sensed by a second plurality of ECG electrodes. Additionally or alternatively, the second plurality of ECG electrodes independent of the plurality of ECG electrodes of the external heart monitoring device.

In some embodiments, the historical collection of the plurality of ECG signal portions may include a first ECG signal portion associated with a first time and a second ECG signal portion associated with a second time after the first time. Additionally or alternatively, the rhythm change classifier may be trained by predicting with the rhythm change classifier a predicted ECG signal portion associated with the second time based on the first ECG signal portion, determining at least one error value based on the predicted ECG signal portion and the second ECG signal portion, and/or training the rhythm change classifier based on the at least one error value. In some embodiments, the at least one error value may include one of a prediction error or a contrastive loss.

In some embodiments, the historical collection of the plurality of ECG signal portions may include a first ECG signal portion associated with a first time and a second ECG signal portion associated with a second time. Additionally or alternatively, the rhythm change classifier may be trained by predicting with the rhythm change classifier a predicted time associated with the second ECG signal portion based on the a first ECG signal portion and the second ECG signal, determining at least one error value based on the predicted time and the second time, and/or training the rhythm change classifier based on the at least one error value.

Embodiments of the current disclosure include an arrhythmia detection system. In some embodiments, the arrhythmia detection system may include a non-transitory computer-readable medium including an arrhythmia type classifier and at least one processor operatively connected to the non-transitory computer readable medium. In some embodiments, the arrhythmia type classifier may include at least one neural network trained based on a historical collection of a plurality of ECG signal portions with known arrhythmia type information. Additionally or alternatively, the at least one processor may be configured to receive at least one ECG signal and annotation data associated with at least one annotation for each of the at least one ECG signal, detect with the arrhythmia type classifier a type of arrhythmia in at least one ECG signal and time data associated with the detected type of arrhythmia, determine based on the time data at least one ECG signal portion associated with the detected type of arrhythmia in the at least one ECG signal, determine a plausibility score for the at least one annotation based on the detected type of arrhythmia, generate at least one message based on the at least one determined ECG signal portion and the plausibility score for the at least one annotation, and/or transmit the at least one message associated with the at least one determined ECG signal portion. In some embodiments, the at least one message may indicate at least one of a recommendation to annotate the at least one determined ECG signal portion based on the detected type of arrhythmia or a recommendation to reevaluate the annotation data associated with the at least one determined ECG signal portion based on the plausibility score.

In some embodiments, the at least one processor may be further configured to determine the plausibility score is below a threshold. Additionally or alternatively, generating the at least one message may include generating, based on the determination that the plausibility score is below the threshold, the at least one message indicating the recommendation to reevaluate the annotation data associated with the at least one determined ECG signal portion.

In some embodiments, the annotation data may be received from a first computing device associated with a technician. Additionally or alternatively, the at least one message may be transmitted to a second computing device associated with a supervisor of the technician.

In some embodiments, the at least one neural network may include at least one deep neural network, a convolutional neural network, a recurrent neural network, an attention network, a fully connected neural network, or any combination thereof.

In some embodiments, the known arrhythmia type information may include a plurality of annotations. Additionally or alternatively, each annotation of the plurality of annotations may be associated with a respective ECG signal portion of the plurality of ECG signal portions, Additionally or alternatively, the arrhythmia type classifier may be trained based on the plurality of ECG signals and the plurality of annotations.

In some embodiments, the plurality of annotations may be from a plurality of technicians. Additionally or alternatively, each annotation of the plurality of annotations may be associated with a respective technician of the plurality of technicians and the respective ECG signal portion of the plurality of ECG signal portions. Additionally or alternatively, the arrhythmia type classifier for a first technician of the plurality of technicians may be trained based on a subset of the plurality of ECG signals and the plurality of annotations associated with at least one other technician of the plurality of technicians different than the first technician. In some embodiments, each annotation may be associated with at least one type of arrhythmia associated with the respective ECG signal portion.

In some embodiments, the historical collection of the plurality of ECG signal portions may include a first plurality of ECG signal portions associated with at least one first ECG electrode and a second plurality of ECG signal portions associated with at least one second ECG electrode. Additionally or alternatively, each respective ECG signal portion of the second plurality of ECG signal portions may correspond to a respective ECG signal portion of the first plurality of ECG signal portions. Additionally or alternatively, the known arrhythmia type information may include a plurality of annotations, and/or each respective annotation of the plurality of annotations may be associated with a respective ECG signal portion of the first plurality of ECG signal portions. Additionally or alternatively, the arrhythmia type classifier may be trained by predicting with the arrhythmia type classifier a predicted type of arrhythmia in each respective ECG signal portion of the second plurality of ECG signal portions, determining at least one error value based on the predicted type of arrhythmia and the respective annotation of the plurality of annotations associated with a respective ECG signal portion of the first plurality of ECG signal portions corresponding to the respective ECG signal portion of the second plurality of ECG signal portions, and training the arrhythmia type classifier based on the at least one error value.

In some embodiments, the historical collection of the plurality of ECG signal portions may include a first plurality of ECG signal portions of at least one first ECG signal based on first surface ECG activity sensed by at least one first ECG electrode and a second plurality of ECG signal portions of at least one second ECG signal based on second surface ECG activity sensed by at least one second ECG electrode. Additionally or alternatively, the at least one second ECG electrode may be independent of the at least one first ECG electrode. Additionally or alternatively, each ECG signal portion of the first plurality of ECG signal portions may be combined with a respective ECG signal portion of the second plurality of ECG signal portions to form a plurality of extrapolated ECG signal portion. Additionally or alternatively, the known arrhythmia type information may include a plurality of annotations, and/or each respective annotation of the plurality of annotations may be associated with a respective extrapolated ECG signal portion of the plurality of extrapolated ECG signal portions.

In some embodiments, at least some of the plurality of ECG signal portions of the historical collection may be time warped to form a plurality of warped ECG signal portions.

In some embodiments, at least some of the plurality of ECG signal portions of the historical collection may be at least one of filtered, inverted, or a combination thereof.

In some embodiments, at least one noise signal portion may be combined with at least some of the plurality of ECG signal portions of the historical collection.

In some embodiments, at least some of the plurality of ECG signal portions of the historical collection may be style transferred.

Embodiments of the current disclosure include an arrhythmia monitoring system. In some embodiments, the arrhythmia monitoring system may include an external heart monitoring device for a patient and a gateway device. The external heart monitoring device may include a plurality of electrocardiogram (ECG) electrodes configured to sense surface ECG activity of the patient, ECG processing circuitry configured to process the surface ECG activity of the patient to provide at least one ECG signal for the patient on at least one ECG channel, and at least one first processor operatively connected to the at least one ECG channel. The first processor(s) may be configured to receive the ECG signal(s) received via the ECG channel(s) and transmit the ECG signal(s) (e.g., to the gateway device). The gateway device may include a non-transitory computer-readable medium comprising a rhythm change classifier and at least one second processor operatively connected to the non-transitory computer-readable medium. The rhythm change classifier may include at least one neural network trained based on a historical collection of a plurality of ECG signal portions with known rhythm change information. The second processor(s) may be configured to receive the ECG signal(s) from the external heart monitoring device; detect with the rhythm change classifier time data corresponding to a predetermined rhythm change in the ECG signal(s), the time data comprising at least one of a start time, a time interval, or any combination thereof; determine based on the detected time data at least one ECG signal portion associated with the detected time data corresponding to the predetermined rhythm change in the ECG signal(s), and transmit the determined ECG signal portion(s) to a remote computer system.

Some embodiments of the current disclosure may include an arrhythmia monitoring system, device, or method according to any one and/or another of the embodiments illustrated, described, and/or disclosed herein.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 3A-C show example swim lane diagrams of communication flows for exemplary processes for cardiac diagnosis and/or arrhythmia monitoring, according to some embodiments.

FIGS. 4A-C show example flowcharts of processes for cardiac diagnosis and/or arrhythmia monitoring, according to some embodiments.

FIGS. 9A-E show an example sensor(s) (e.g., of external heart monitoring device(s)) disclosed herein, a patch configured to hold the sensor(s) in proximity to a body, and attachment of a patch housing a sensor(s) onto skin of a patient, according to some embodiments.

DETAILED DESCRIPTION OF SOME OF THE EMBODIMENTS

Figure 1A:
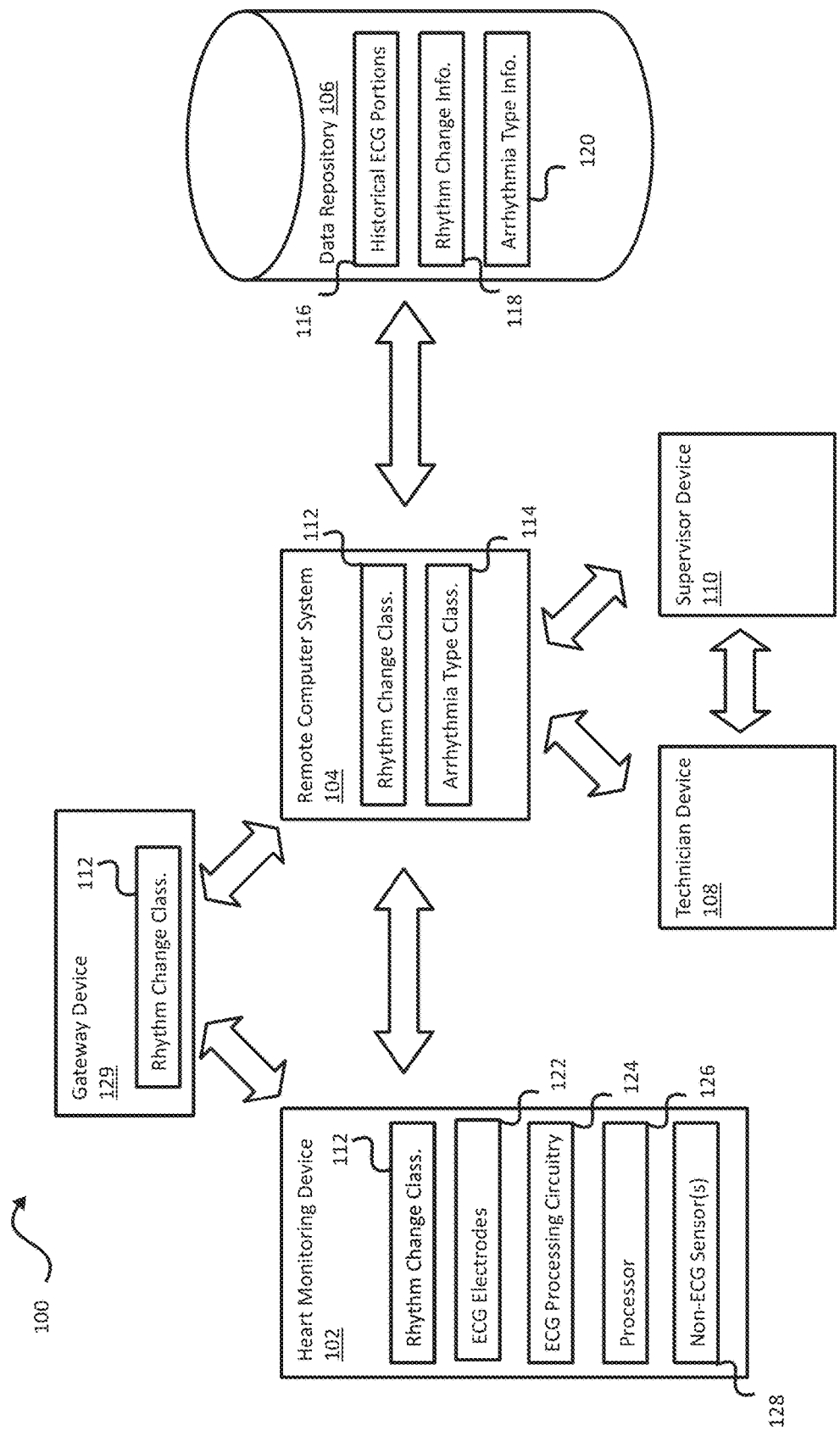
FIGS. 1A-C show example block diagrams of an environment for cardiac diagnosis and/or arrhythmia monitoring, according to some embodiments.

This disclosure relates to systems, devices and methods for cardiac diagnosis and/or arrhythmia monitoring, including heart failure status monitoring. For example, one or more trained classifier(s), each of which including at least one neural network, may be used by a heart monitoring device (e.g., external, wearable, and/or the like heart monitoring device), computer system, and/or the like to detect (e.g., identify and/or the like) a rhythm change, a type of arrhythmia, and/or the like based on at least one ECG signal or portion(s) thereof. Example use scenarios include use of the systems, devices, and methods for cardiac diagnosis and/or arrhythmia monitoring in the context of mobile cardiac telemetry, cardiac holter monitoring (including extended cardiac holter monitoring), wearable cardiac monitors, wearable defibrillators, wearable cardioverter defibrillators, and other such ambulatory cardiac monitoring and/or treatment systems.

In some embodiments, an arrhythmia monitoring system may include an external heart monitoring device for a patient. For example, the external heart monitoring device may include a plurality of electrocardiogram (ECG) electrodes to sense surface ECG activity of the patient. ECG processing circuitry may process the surface ECG activity of the patient to provide at least one ECG signal for the patient on at least one ECG channel A rhythm change classifier may be implemented in a non-transitory computer-readable medium (e.g., a memory, a programmable circuit board, a field programmable gate array, an integrated circuit, any combination thereof, and/or the like). The rhythm change classifier may include at least one neural network trained based on a historical collection of a plurality of ECG signal portions with known rhythm change information. Additionally, at least one processor may be operatively connected to the ECG channel(s) and the non-transitory computer-readable medium. The processor(s) may receive the ECG signal(s) via the ECG channel(s). The processor(s) may also use the rhythm change classifier to detect time data corresponding to a rhythm change (e.g., predetermined rhythm change and/or the like) in the ECG signal(s). For example, the time data may include a start time, a time interval, any combination thereof, and/or the like. The processor(s) may also determine, based on the detected time data, at least one ECG signal portion associated with the detected time data corresponding to the predetermined rhythm change in the ECG signal(s). The processor(s) may also transmit the determined ECG signal portion(s) to a remote computer system (e.g., a remote server, a cardiac monitoring facility, and/or the like).

For example, in such embodiments, the rhythm change classifier (e.g., neural network(s) and/or the like thereof) may detect (e.g., identify and/or the like) the rhythm change without having to classify the specific rhythm type. For the purpose of illustration, the rhythm change classifier may detect a rhythm when heart rhythm changes from normal sinus rhythm (NSR) to Atrial Fibrillation (AFIB), from AFIB to NSR, from AFIB to Atrial Flutter (AFL), from one morphology to another, and/or the like. Additionally, every time a rhythm change is detected (e.g., identified and/or the like), an ECG signal portions (e.g., ECG strip and/or the like) containing the detected rhythm change may be transmitted to the remote computer system (e.g., with an indication, message, marking, and/or the like indicating a detected rhythm change). Additionally or alternatively, the rhythm change classifier may determine a confidence score associated with the detected rhythm change (e.g., output the confidence score associated with the probability that the detected rhythm change actually is a rhythm change).

In some embodiments, the rhythm change classifier may also use (e.g., receive as input for the neural network(s) and/or the like) data associated with additional sensors (e.g., non-ECG biometric data from at least one sensor), including but not limited to accelerometer data, heart sound data, electromagnetic waves (e.g., radio frequency (RF) waves and/or the like) scattered and/or reflected from internal tissues, any combination thereof, and/or the like. Such additional non-ECG biometric data may further enhance the accuracy, confidence, and/or the like associated with the detection of rhythm changes.

In some embodiments, the rhythm change classifier may also use (e.g., receive as input for the neural network(s), compare, and/or the like) data associated baseline ECG signal(s), reference vector(s), calibration measurement(s), previous measurement(s), and/or the like for the patient. For example, such baseline signal(s) and/or additional measurement(s) may be acquired in a clinic using high-accuracy equipment, acquired by the external heart monitoring device during known rest times, and/or the like. Use of such baseline signal(s) and/or additional measurement(s) specific to the patient may further enhance the accuracy, confidence, and/or the like associated with the detection of rhythm changes.

In some embodiments, the use of a trained neural network to detect (e.g., identify and/or the like) the rhythm change(s) and only transmit the ECG signal portion(s) when the rhythm change(s) is (are) detected may allow for reduced power consumption, e.g., suitable for a wearable external device with a relatively small power source (e.g., battery and/or the like). Additionally, the rhythm change classifier (e.g., neural network(s) thereof) may be implemented using low-power hardware (e.g., a programmable circuit board, a field programmable gate array, an integrated circuit, and/or the like), which may further reduce the power consumption.

In some embodiments, classifier(s) and/or neural network logic thereof may be distributed across multiple devices (e.g., the external heart monitoring device, a gateway device, and/or the remote computer system), e.g., to optimize power consumption, to reduce the amount of data transmitted, enhance accuracy of detection of rhythm changes, and/or to address other constraints. For example, the rhythm change classifier may be implemented (e.g., completely, partially, and/or the like) on a gateway device (e.g., mobile computing device, such as a smart phone, tablet, laptop computer, and/or the like), which may receive the ECG signal data and/or other sensor data from the external heart monitoring device (e.g., via low-power wireless transmission, such as Bluetooth, Bluetooth Low Energy (BLE), and/or the like). Additionally or alternatively, a second classifier (e.g., larger and more accurate rhythm change classifier, arrhythmia type classifier, and/or the like) may be implemented (e.g., completely, partially, and/or the like) on the remote computer system.

In some embodiments, additional ECG signal portions may be sampled (e.g., randomly, at predetermined intervals, based on confidence scores below an upper threshold but above a lower threshold, and/or the like) and transmitted from the external heart monitoring device to the remote computer system for annotation (e.g., by technicians and/or the like) in order to test performance of the classifier(s) (e.g., rhythm change classifier, arrhythmia type classifier, and/or the like), to enlarge the training dataset (e.g., be added to the historical collection of ECG signal portions and/or the like), to retrain the classifier(s), and/or the like.

In some embodiments, ECG signal portions transmitted from the external heart monitoring device to the remote computer system may be classified (e.g., bucketed and/or the like), grouped, and/or the like. Additionally, ECG signal portions in the same classification/group may be presented to a user (e.g., technician and/or the like) together, which may enhance human review (e.g., processing, interrogation, annotation, and/or the like) of such ECG signal portion(s).

In some embodiments, an arrhythmia detection system may include at least one non-transitory computer-readable medium (e.g., a memory, a programmable circuit board, a field programmable gate array, an integrated circuit, any combination thereof, and/or the like) and at least one processor may be operatively connected thereto. An arrhythmia type classifier may be implemented in the non-transitory computer-readable medium. The arrhythmia type classifier may include at least one neural network trained based on a historical collection of a plurality of ECG signal portions with known arrhythmia type information. The processor(s) may receive at least one ECG signal and annotation data associated with at least one annotation for each of the ECG signal(s). For example, the annotation data may be received from a computing device associated with a technician. The processor(s) may detect, with the arrhythmia type classifier, a type of arrhythmia in the ECG signal(s) and time data associated with the detected type of arrhythmia. The time data may include at least one of a start time, a time interval, or any combination thereof. The processor(s) may determine, based on the time data, at least one ECG signal portion associated with the detected type of arrhythmia in the ECG signal(s). The processor(s) may determine a plausibility score for the annotation(s) based on the detected type of arrhythmia. The processor(s) may generate at least one message based on the determined ECG signal portion(s) and the plausibility score for the annotation(s). for example, the message(s) may indicate at least one of a recommendation to annotate the determined ECG signal portion(s) based on the detected type of arrhythmia, a recommendation to reevaluate the annotation data associated with the determined ECG signal portion(s) based on the plausibility score, and/or the like. The processor(s) may transmit the message(s) associated with the ECG signal portion(s), e.g., to the computing device of the technician.

For example, in such embodiments, technicians may have different levels of experience, expertise, and/or the like. Such a system, using such an arrhythmia type classifier, may identify inconsistencies, anomalies, missed arrhythmias, and/or the like. Additionally or alternatively, such a system may route (e.g., communicate, transmit, and/or the like) the identified ECG signal portions to the technician, to another more senior technician (e.g., supervisor of the initial technician) and/or the like, for additional review (e.g., processing, interrogation, annotation, and/or the like).

Figure 1B:
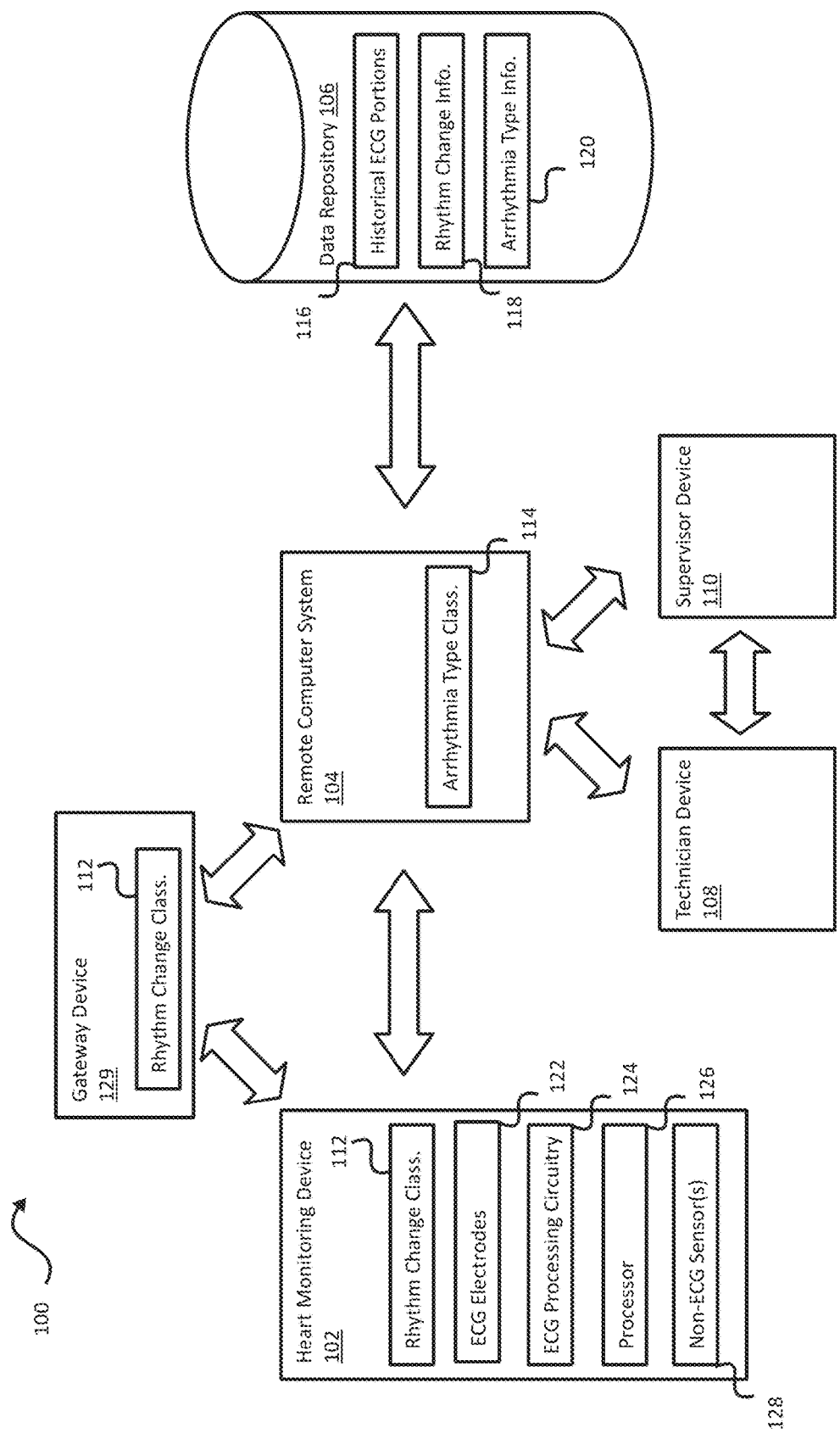
Figure 1C:
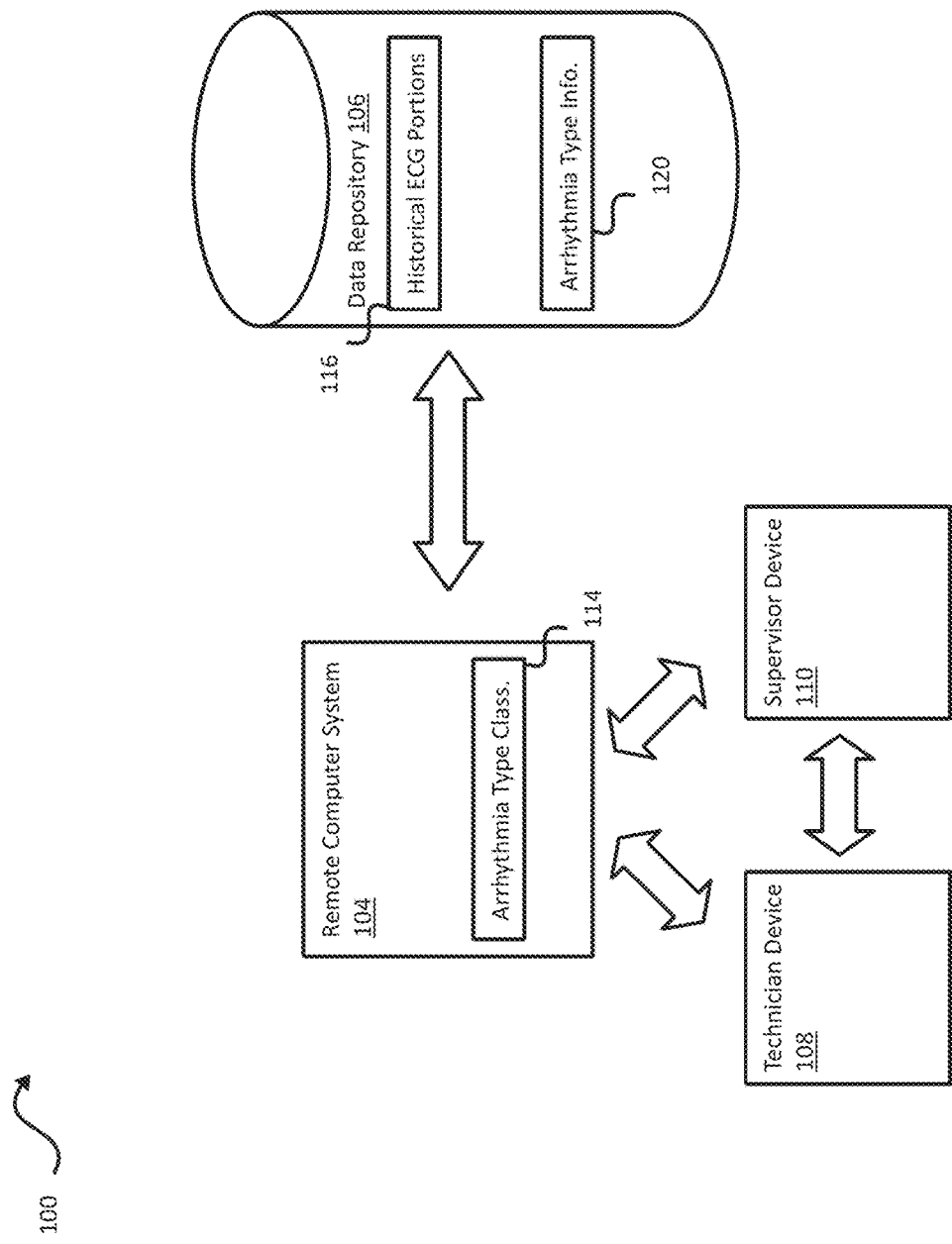

Referring to FIGS. 1A-C, FIGS. 1A-C show example block diagrams of an environment 100 in which systems, products, and/or methods, as described herein, may be implemented. As shown in FIGS. 1A-C, environment 100 may include heart monitoring device 102, remote computer system 104, data repository 106, technician device 108, supervisor device 110, and/or gateway device 129.

Heart monitoring device 102 may include one or more devices capable of receiving information from and/or communicating information to remote computer system 104, gateway device 129, data repository 106, technician device 108, and/or supervisor device 110 (e.g., directly and/or indirectly via wired and/or wireless network and/or any other suitable communication technique). In some embodiments, heart monitoring device 102 may be an external heart monitoring device (e.g., wearable by a patient, connected externally to a patient, and/or the like), as described herein. In some embodiments, heart monitoring device 102 may include a ECG electrodes 122 (e.g., a plurality of ECG electrodes configured to sense surface ECG activity of the patient), ECG processing circuitry 124 (e.g., ECG processing circuitry configured to process the surface ECG activity of the patient to provide at least one ECG signal for the patient on at least one ECG channel), rhythm change classifier 112 (e.g., implemented by at least one non-transitory computer readable medium), processor 126 (e.g., at least one processor operatively connected to the at least one ECG channel and the non-transitory computer-readable medium), non-ECG sensors 128 (e.g., at least one sensor and associated sensor circuitry configured to sense non-ECG biometric data of the patient), and/or the like, as described herein. In some embodiments, rhythm change classifier 112 may include at least one neural network trained based on historical collection of a plurality of ECG signal portions 116 with known rhythm change information 118, as described herein. In some embodiments, processor 126 may be configured to receive at least one ECG signal via the at least one ECG channel (e.g., from ECG processing circuitry 124), as described herein. Additionally or alternatively, processor 126 may be configured to detect (e.g., with rhythm change classifier 112) time data corresponding to a predetermined rhythm change in the ECG signal(s), as described herein. In some embodiments, the time data may include at least one of a start time, a time interval, any combination thereof, and/or the like, as described herein. Additionally or alternatively, processor 126 may be configured to determine (e.g., based on the detected time data) at least one ECG signal portion associated with the detected time data corresponding to the predetermined rhythm change in the at least one ECG signal, as described herein. Additionally or alternatively, processor 126 may be configured to transmit the at least one determined ECG signal portion to remote computer system 104, as described herein.

Remote computer system 104 may include one or more devices capable of receiving information from and/or communicating information to heart monitoring device 102, gateway device 129, data repository 106, technician device 108, and/or supervisor device 110 (e.g., directly and/or indirectly via wired and/or wireless network and/or any other suitable communication technique). In some embodiments, remote computer system 104 may include a server, a group of servers, and/or other like devices, as described herein. Additionally or alternatively, remote computer system 104 may include at least one other computing device separate from or including the server and/or group of servers, such as a portable and/or handheld device (e.g., a computer, a laptop, a personal digital assistant (PDA), a smartphone, a tablet, and/or the like), a desktop computer, and/or other like devices, as described herein. In some embodiments, remote computer system 104 may be associated with a cardiac monitoring facility, and/or the like, as described herein. Additionally or alternatively, the cardiac monitoring facility may be associated with a provider (e.g., manufacturer, distributor, and/or the like) of heart monitoring device 102, as described herein. In some embodiments, remote computer system 104 may include at least one classifier (e.g., rhythm change classifier 112, arrhythmia type classifier 114, and/or the like), as described herein. Additionally or alternatively, each classifier (e.g., rhythm change classifier 112, arrhythmia type classifier 114, and/or the like) may be implemented by at least one non-transitory computer readable medium. In some embodiments, remote computer system 104 may include at least one processor operatively connected to the non-transitory computer readable medium, as described herein. In some embodiments, remote computer system 104 may be in communication with data repository 106, which may be local or remote to remote computer system 104. In some embodiments, remote computer system 104 may be capable of receiving information from, storing information in, communicating information to, or searching information stored in data repository 106.

In some embodiments, remote computer system 104 (e.g., processor(s) thereof) may be configured to receive at least one determined ECG signal portion from (external) heart monitoring device 102, analyze the determined ECG signal portion(s) to classify a type of arrhythmia for the rhythm change in the ECG signal(s), and/or the like, as described herein. For example, arrhythmia type classifier 114 may include at least one (second) neural network trained based on a (second) historical collection of a (second) plurality of ECG signal portions 116 with known arrhythmia type information 120, as described herein. In some embodiments, the type of arrhythmia may include at least one of a change in heart rate, atrial fibrillation, flutter, supraventricular tachycardia, ventricular tachycardia, pause, AV block, ventricular fibrillation, bigeminy, trigeminy, ventricular ectopic beats, bradycardia, tachycardia, a change in morphology of the at least one ECG signal, any combination thereof, and/or the like, as described herein.

In some embodiments, remote computer system 104 (e.g., processor(s) thereof) may be configured to receive at least one ECG signal and annotation data associated with at least one annotation for each ECG signal, as described herein. Additionally or alternatively, remote computer system 104 (e.g., processor(s) thereof) may be configured to detect (e.g., with arrhythmia type classifier 114) a type of arrhythmia in the ECG signal(s) and time data associated with the detected type of arrhythmia, as described herein. In some embodiments, the time data may include at least one of a start time, a time interval, any combination thereof, and/or the like, as described herein. In some embodiments, remote computer system 104 (e.g., processor(s) thereof) may be configured to determine (e.g., based on the time data) at least one ECG signal portion associated with the detected type of arrhythmia in the ECG signal(s), as described herein. In some embodiments, remote computer system 104 (e.g., processor(s) thereof) may be configured to determine a plausibility score for the annotation(s) based on the detected type of arrhythmia, as described herein. In some embodiments, remote computer system 104 (e.g., processor(s) thereof) may be configured to generate at least one message based on the determined ECG signal portion(s) and the plausibility score for the annotation(s), as described herein. Additionally or alternatively, the message(s) may indicate at least one of a recommendation to annotate the determined ECG signal portion(s) based on the detected type of arrhythmia, a recommendation to reevaluate the annotation data associated with the determined ECG signal portion(s) based on the plausibility score, and/or the like, as described herein. In some embodiments, remote computer system 104 (e.g., processor(s) thereof) may be configured to transmit the message(s) associated with the determined ECG signal portion(s) (e.g., to technician device 108, supervisor device 110, and/or the like).

Data repository 106 may include one or more devices capable of receiving information from and/or communicating information to heart monitoring device 102, remote computer system 104, gateway device 129, technician device 108, and/or supervisor device 110 (e.g., directly and/or indirectly via wired and/or wireless network and/or any other suitable communication technique). In some embodiments, data repository 106 may include a server, a group of servers, and/or other like devices, as described herein. In some embodiments, data repository 106 may be associated with a cardiac monitoring facility, and/or the like, as described herein. Additionally or alternatively, the cardiac monitoring facility may be associated with a provider (e.g., manufacturer, distributor, and/or the like) of heart monitoring device 102, as described herein. In some embodiments, data repository 106 may be part of remote computer system 104. Additionally or alternatively, data repository 106 may be local or remote to remote computer system 104. In some embodiments, remote computer system 104 may be capable of receiving information from, storing information in, communicating information to, or searching information stored in data repository 106.

In some embodiments, data repository 106 may include at least one historical collection of a plurality of ECG signal portions 116, as described herein. Additionally or alternatively, data repository 106 may include known rhythm change information 118 for at least some of the historical collection of a plurality of ECG signal portions 116 (e.g., a first plurality of ECG signal portions and/or the like), as described herein. Additionally or alternatively, data repository 106 may include known arrhythmia type information 120 for at least some of the historical collection of a plurality of ECG signal portions 116 (e.g., a second plurality of ECG signal portions and/or the like), as described herein. In some embodiments, the data repository 106 may include patient-specific information, e.g., baseline ECG and/or other baseline physiological information, reference ECG and/or other reference physiological information specific to the patient, patient-specific calibration data, and/or the like. For example, prior to initial deployment on the patient, heart monitoring device 102 may be fitted on the patient, and/or initial patient-specific information (e.g., baseline ECG and/or physiological data and/or the like) may be determined using heart monitoring device 102. Such patient-specific information may be designated as the baseline data for the patient. Additionally or alternatively, certain patient-specific data may be designated as reference data for certain analysis, as described herein. In some embodiments, data repository 106 may include patient-specific classifiers (e.g., patient-specific rhythm change classifiers, patient-specific arrhythmia type classifiers, and/or the like) that may be trained as described herein based on such baseline and/or reference data.

Technician device 108 may include one or more devices associated with a technician and capable of receiving information from and/or communicating information to heart monitoring device 102, remote computer system 104, gateway device 129, data repository 106, and/or supervisor device 110 (e.g., directly and/or indirectly via wired and/or wireless network and/or any other suitable communication technique). In some embodiments, technician device 108 may include at least one computing device, such as a portable and/or handheld device (e.g., a computer, a laptop, a personal digital assistant (PDA), a smartphone, a tablet, and/or the like), a desktop computer, and/or other like devices, as described herein. In some embodiments, technician device 108 may be associated with a cardiac monitoring facility, and/or the like, as described herein. Additionally or alternatively, the cardiac monitoring facility may be associated with a provider (e.g., manufacturer, distributor, and/or the like) of heart monitoring device 102, as described herein. In some embodiments, technician device 108 may be part of remote computer system 104. Additionally or alternatively, technician device 108 may be local or remote to remote computer system 104. In some embodiments, technician device 108 may include at least one input component that permits technician device 108 to receive information, such as via user input (e.g., a touch screen display, a keyboard, a keypad, a mouse, a button, a switch, a microphone, a camera, and/or the like). Additionally or alternatively, technician device 108 may include at least one output component that provides output information from technician device 108 (e.g., a display, a touch screen, a speaker, and/or the like). In some embodiments, technician device 108 may receive messages (e.g., recommendations regarding annotations, identifications of types of arrhythmia, identifications of rhythm changes, classifications, and/or the like) associated with ECG signals and/or portions thereof (e.g., from remote computer system 104, heart monitoring device 102, supervisor device 110, and/or the like), as described herein. Additionally or alternatively, technician device 108 may communicate annotation data associated with at least one annotation for a respective ECG signal and/or portion thereof (e.g., to remote computer system 104, heart monitoring device 102, supervisor device 110, and/or the like), as described herein.

Supervisor device 110 may include one or more devices associated with a supervisor (e.g., supervisor of at least one technician and/or the like) and capable of receiving information from and/or communicating information to heart monitoring device 102, remote computer system 104, gateway device 129, data repository 106, and/or technician device 108 (e.g., directly and/or indirectly via wired and/or wireless network and/or any other suitable communication technique). In some embodiments, supervisor device 110 may include at least one computing device, such as a portable and/or handheld device (e.g., a computer, a laptop, a personal digital assistant (PDA), a smartphone, a tablet, and/or the like), a desktop computer, and/or other like devices, as described herein. In some embodiments, supervisor device 110 may be associated with a cardiac monitoring facility, and/or the like, as described herein. Additionally or alternatively, the cardiac monitoring facility may be associated with a provider (e.g., manufacturer, distributor, and/or the like) of heart monitoring device 102, as described herein. In some embodiments, supervisor device 110 may be part of remote computer system 104. Additionally or alternatively, supervisor device 110 may be local or remote to remote computer system 104. In some embodiments, supervisor device 110 may include at least one input component that permits supervisor device 110 to receive information, such as via user input (e.g., a touch screen display, a keyboard, a keypad, a mouse, a button, a switch, a microphone, a camera, and/or the like). Additionally or alternatively, supervisor device 110 may include at least one output component that provides output information from supervisor device 110 (e.g., a display, a touch screen, a speaker, and/or the like). In some embodiments, supervisor device 110 may receive messages (e.g., recommendations regarding annotations, identifications of types of arrhythmia, identifications of rhythm changes, classifications, and/or the like) associated with ECG signals and/or portions thereof (e.g., from remote computer system 104, heart monitoring device 102, technician device 108, and/or the like), as described herein. Additionally or alternatively, supervisor device 110 may communicate annotation data associated with at least one annotation for a respective ECG signal and/or portion thereof (e.g., to remote computer system 104, heart monitoring device 102, technician device 108, and/or the like), as described herein.

Gateway device 129 may include one or more devices capable of receiving information from and/or communicating information to heart monitoring device 102, remote computer system 104, data repository 106, technician device 108, and/or supervisor device 110 (e.g., directly and/or indirectly via wired and/or wireless network and/or any other suitable communication technique). In some embodiments, gateway device 129 may include at least one computing device, such as a portable and/or handheld device (e.g., a computer, a laptop, a personal digital assistant (PDA), a smartphone, a tablet, and/or the like), a desktop computer, and/or other like devices, as described herein. In some embodiments, gateway device 129 may be associated with a patient, e.g., a respective patient associated with (e.g., connected to, implanted with, and/or the like) heart monitoring device 102. In some embodiments, gateway device 129 may be associated with a cardiac monitoring facility, and/or the like, as described herein. Additionally or alternatively, the cardiac monitoring facility may be associated with a provider (e.g., manufacturer, distributor, and/or the like) of heart monitoring device 102, as described herein. In some embodiments, gateway device 129 may be local or remote to remote heart monitoring system 102. Additionally or alternatively, gateway device 129 may be local or remote to remote computer system 104. In some embodiments, gateway device 129 may include at least one input component that permits gateway device 129 to receive information, such as via user input (e.g., a touch screen display, a keyboard, a keypad, a mouse, a button, a switch, a microphone, a camera, and/or the like). Additionally or alternatively, gateway device 129 may include at least one output component that provides output information from gateway device 129 (e.g., a display, a touch screen, a speaker, and/or the like). In some embodiments, gateway device 129 may receive biometric data (e.g., ECG signals, ECG signal portions, non-ECG biometric data associated with at least one sensor, and/or the like) from heart monitoring device 102 and/or the like, as described herein. Additionally or alternatively, gateway device 129 may communicate biometric data (e.g., ECG signals, ECG signal portions, non-ECG biometric data associated with at least one sensor, and/or the like) to remote computer system 104 and/or the like, as described herein. In some embodiments, rhythm change classifier 112 may be implemented (e.g., completely, partially, and/or the like) by a non-transitory computer readable medium of gateway device 129 (e.g., independent of, in lieu of, or in addition to heart monitoring device 102). Additionally or alternatively, a processor of gateway device 129 may be configured to receive at least one ECG signal (e.g., from heart monitoring device 102) and/or detect (e.g., with rhythm change classifier 112) time data corresponding to a predetermined rhythm change in the ECG signal(s), as described herein. In some embodiments, the time data may include at least one of a start time, a time interval, any combination thereof, and/or the like, as described herein. Additionally or alternatively, a processor of gateway device 129 may be configured to determine (e.g., based on the detected time data) at least one ECG signal portion associated with the detected time data corresponding to the predetermined rhythm change in the at least one ECG signal and/or transmit the at least one determined ECG signal portion to remote computer system 104, as described herein.

In some embodiments, heart monitoring device 102, remote computer system 104, data repository 106, technician device 108, supervisor device 110, and/or gateway device 129 may be connected by one or more networks. The network(s) may include one or more wired and/or wireless networks. For example, the network(s) may include a cellular network (e.g., a long-term evolution (LTE) network, a third generation (3G) network, a fourth generation (4G)

network, a code division multiple access (CDMA) network, and/or the like), a public land mobile network (PLMN), a local area network (LAN), a wide area network (WAN), a metropolitan area network (MAN), a telephone network (e.g., the public switched telephone network (PSTN)), a private network, a virtual private network (VPN), a local network, an ad hoc network, an intranet, the Internet, a fiber optic-based network, a cloud computing network, and/or the like, and/or a combination of these or other types of networks.

Figure 2A:
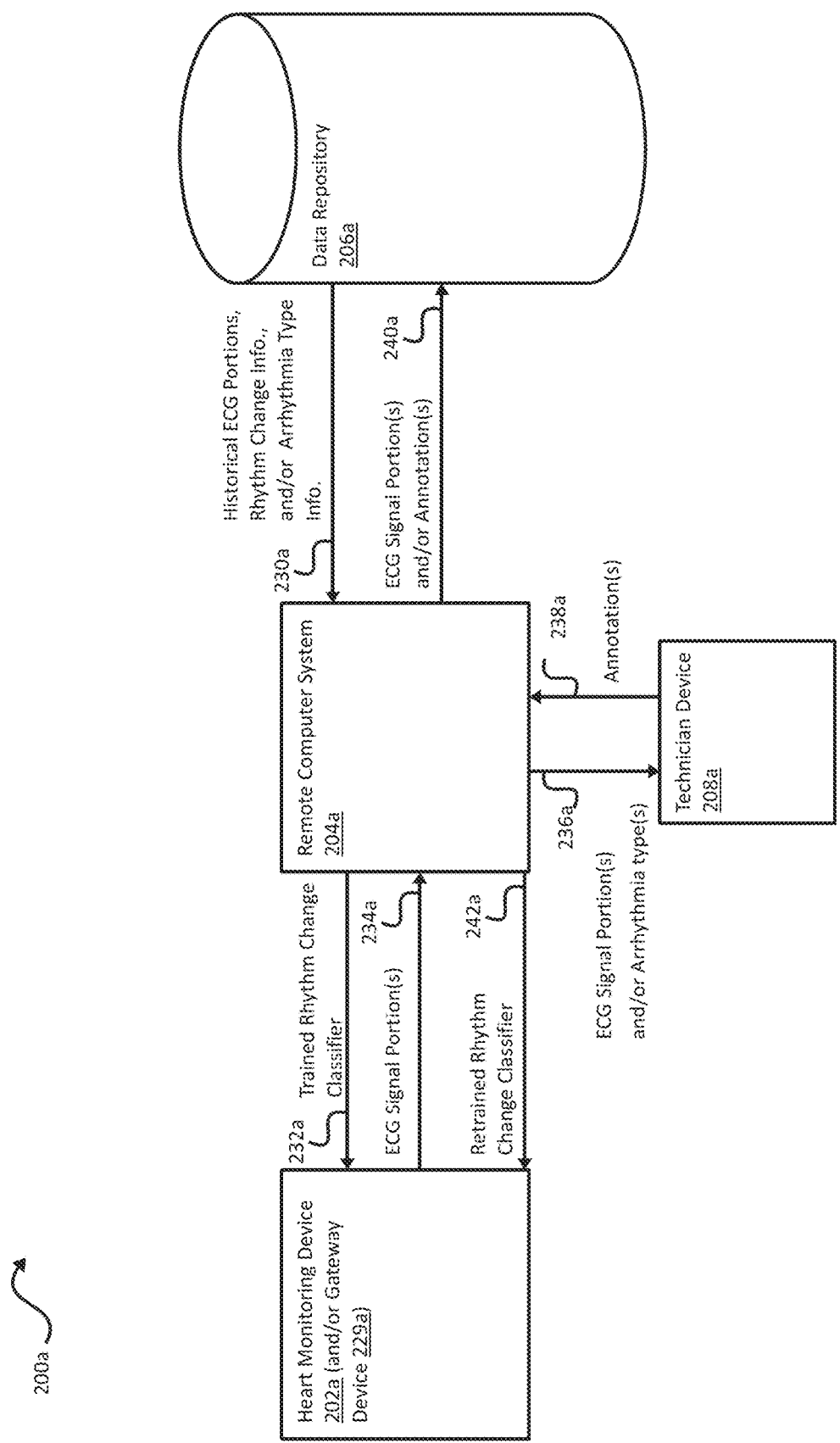
FIGS. 2A-C shows example block diagrams of system architectures for cardiac diagnosis and/or arrhythmia monitoring, according to some embodiments.

Referring now to FIG. 2A, FIG. 2A shows an example block diagram of a system architecture 200a for arrhythmia monitoring, according to some embodiments. In addition to system components, the system architecture 200a also shows data flows between the system components. As shown in FIG. 2A, system architecture 200a may include heart monitoring device 202a, remote computer system 204a, data repository 206a, technician device 208a, and/or gateway device 229a. In some embodiments, heart monitoring device 202a may be the same as or similar to heart monitoring device 102. In some embodiments, remote computer system 204a may be the same as or similar to remote computer system 104 (e.g., one or more devices of remote computer system 104). In some embodiments, data repository 206a may be the same as or similar to data repository 106 (e.g., one or more devices of data repository 106). In some embodiments, technician device 208a may be the same as or similar to technician device 108. In some embodiments, gateway device 229a may be the same as or similar to gateway device 129.

As shown in FIG. 2A, at 230a, remote computer system 204a may receive (e.g., retrieve, search for, send a request and/or query to cause data repository 206a to communicate, and/or the like) a historical collection of a plurality of ECG signal portions and information related thereto (e.g., known rhythm change information, known arrhythmia type information, and/or the like), e.g., from data repository 206a, as described herein. In some embodiments, remote computer system 204a may train at least one neural network of at least one classifier (e.g., a rhythm change classifier, an arrhythmia type classifier, and/or the like) based on the historical collection of a plurality of ECG signal portions and information related thereto (e.g., known rhythm change information, known arrhythmia type information, and/or the like, respectively), as described herein.

In some embodiments, a rhythm change classifier may include at least one neural network, as described herein. Additionally or alternatively, the at least one neural network may include at least one of a convolutional neural network, a recurrent neural network, an attention network, a fully connected neural network, any combination thereof, and/or the like. For example, the neural network(s) may include at least one convolutional neural network having a plurality of convolutional layers. In some embodiments, the convolutional neural network(s) may include between five and 40 convolutional layers (e.g., at least five convolutional layers and up to 40 convolutional layers). For example, the convolutional neural network(s) may include between seven and ten convolutional layers (e.g., at least seven convolutional layers and no more than ten convolutional layers). In some embodiments, each convolutional layer may include at least one convolutional nodes (e.g., a plurality of convolutional nodes). In some embodiments, the convolutional neural network(s) may further include an input layer and an output layer. For example, the ECG signal(s) may include a plurality of ECG signal samples. Additionally or alternatively, the input layer may include at least one node for each ECG signal sample of the plurality of ECG signal samples (or a subset thereof, e.g., associated with a predetermined time period, a buffer size of a buffer for ECG signal samples, and/or the like). Additionally or alternatively, the input layer may further include at least one input for non-ECG biometric data associated with each sensor of heart monitoring device 202a, as described herein. In some embodiments, an output of the output layer may include an indication of the time data corresponding to the rhythm change. Additionally or alternatively, an output of the output layer may include a confidence score, as described herein. In some embodiments, the neural network(s) may include a plurality of Siamese branches (e.g., each respective Siamese branch associated with a respective ECG channel), as described herein.

In some embodiments, remote computer system 204a may train the rhythm change classifier. For example, remote computer system 204a may train the rhythm change classifier by generating, with the rhythm change classifier, predicted rhythm change information (e.g., data (e.g., probability, confidence score, and/or the like) associated with a predicted rhythm change, data (e.g., probability, confidence score, and/or the like) associated with a lack of a predicted rhythm change, and/or the like) for each ECG signal portion of the historical collection of the plurality of ECG signal portions (or a first plurality thereof), determining at least one error value based on the predicted rhythm change information and the known rhythm change information, and updating the rhythm change classifier (e.g., updating the weights thereof and/or the like) based on the error value(s) (e.g., using back propagation and/or the like). In some embodiments, the error value(s) may include one of a prediction error or a contrastive loss.

In some embodiments, the historical collection of the plurality of ECG signal portions may include a first ECG signal portion associated with a first time and a second ECG signal portion associated with a second time after the first time. Additionally or alternatively, remote computer system 204a may train the rhythm change classifier by generating, with the rhythm change classifier, a predicted ECG signal portion associated with the second time based on the first ECG signal portion, determining at least one error value based on the predicted ECG signal portion and the second ECG signal portion, and updating the rhythm change classifier (e.g., updating the weights thereof and/or the like) based on the error value(s) (e.g., using back propagation and/or the like). In some embodiments, the error value(s) may include one of a prediction error or a contrastive loss.

In some embodiments, the historical collection of the plurality of ECG signal portions may include a first ECG signal portion associated with a first time and a second ECG signal portion associated with a second time. Additionally or alternatively, remote computer system 204a may train the rhythm change classifier by generating, with the rhythm change classifier, a predicted time associated with the second ECG signal portion based on the a first ECG signal portion and the second ECG signal, determining at least one error value based on the predicted time and the second time, and updating the rhythm change classifier (e.g., updating the weights thereof and/or the like) based on the error value(s) (e.g., using back propagation and/or the like). In some embodiments, the error value(s) may include one of a prediction error or a contrastive loss.

In some embodiments, there may be an insufficient number of ECG signal portions in the historical collection of the plurality of ECG signal portions with known rhythm change information to train the rhythm change classifier to perform the desired task (e.g., detect and/or identify at least one predetermined rhythm changes). Additionally or alternatively, there may be sufficient data (e.g., historical ECG signal portions and/or the like) to train the rhythm change classifier to perform a separate task (e.g., which may be related in some way to the target task). In some embodiments, the rhythm change classifier may be trained to perform the separate task (e.g., counting R-peaks, determining heart rate, and/or the like based on the ECG signal(s)). Additionally or alternatively, the rhythm change classifier may then be adapted to perform the target task. For example, in some embodiments, the rhythm change classifier may be retrained using the limited amount of ECG signal portions in the historical collection of the plurality of ECG signal portions with known rhythm change information and/or the like. Additionally or alternatively, the rhythm change classifier may be used to perform the separate task (e.g., counting R-peaks, determining heart rate, and/or the like based on the ECG signal(s)), and the output thereof may be applied to the target task. For example, the processor (e.g., of heart monitoring device 202a and/or gateway device 229a) may detect, with the rhythm change classifier, at least one of a count of peaks or a heart rate based on the at least one ECG signal. Additionally or alternatively, the processor (e.g., of heart monitoring device 202a and/or gateway device 229a) may determine the detected at least one of the count of peaks or the heart rate is above a first threshold (e.g., tachycardia onset threshold) for the patient or below a second threshold (e.g., bradycardia onset threshold) for the patient (e.g., wherein the second threshold for the patient may be less than the first threshold for the patient). Additionally or alternatively, the processor (e.g., of heart monitoring device 202a and/or gateway device 229a) may detect the predetermined rhythm change based on the at least one of the count of peaks or the heart rate being above the first threshold (e.g., tachycardia onset threshold) for the patient or below the second threshold (e.g., bradycardia onset threshold) for the patient.

In some embodiments, there may be an insufficient number of ECG signal portions associated with (e.g., sensed from and/or the like) the plurality of ECG electrodes of the heart monitoring device 202a in the historical collection of the plurality of ECG signal portions with known rhythm change information to train the rhythm change classifier for the ECG signal(s) received form the plurality of ECG electrodes of the heart monitoring device 202a. Additionally or alternatively, there may be sufficient data (e.g., historical ECG signal portions and/or the like) associated with (e.g., sensed from and/or the like) a second plurality of ECG electrodes (e.g., electrodes from an ECG device separate from the heart monitoring device 202a, such as a 12-lead ECG sensor, a separate external and/or wearable heart monitoring device, and/or the like) independent of the plurality of ECG electrodes of the heart monitoring device 202a to train the rhythm change classifier based on the second plurality of ECG electrodes. In some embodiments, the rhythm change classifier may be trained based on the ECG signal portion(s) associated with (e.g., sensed from and/or the like) the second plurality of ECG electrodes. Additionally or alternatively, the rhythm change classifier may then be adapted to detect the predetermined rhythm change(s) based on the plurality of ECG electrodes of the heart monitoring device 202a. In some embodiments, remote computer system 204a may determine (e.g., calculate and/or the like) a transform (e.g., vector projection and/or the like) of the ECG signal portion(s) associated with the second plurality of ECG electrodes to the plurality of ECG electrodes of the heart monitoring device 202a, and the transform of the ECG signal portion(s) may be used to train the rhythm change classifier as if the ECG signal portions were associated with (e.g., sensed from and/or the like) the plurality of ECG electrodes of the heart monitoring device 202a.

In some embodiments, remote computer system 204a may train an arrhythmia type classifier by predicting, with the arrhythmia type classifier, a predicted type of arrhythmia in each respective ECG signal portion of the historical collection of the plurality of ECG signal portions (or a second plurality thereof), determining at least one error value based on the predicted type of arrhythmia and the known arrhythmia type information (e.g., a respective annotations associated with a known type of arrhythmia for each respective ECG signal portion), and training the arrhythmia type classifier (e.g., updating the weights thereof and/or the like) based on the error value(s) (e.g., using back propagation and/or the like). In some embodiments, the error value(s) may include one of a prediction error or a contrastive loss.

In some embodiments, an arrhythmia type classifier may include at least one neural network (e.g., at least one second neural network), as described herein. Additionally or alternatively, the at least one (second) neural network may include at least one of a deep neural network, a convolutional neural network, a recurrent neural network, an attention network, a fully connected neural network, any combination thereof, and/or the like. For example, the neural network(s) may include at least one convolutional neural network having a plurality of convolutional layers. In some embodiments, the convolutional neural network(s) may include between five and 40 convolutional layers (e.g., at least five convolutional layers and up to 40 convolutional layers). For example, the convolutional neural network(s) may include between seven and ten convolutional layers (e.g., at least seven convolutional layers and no more than ten convolutional layers). In some embodiments, each convolutional layer may include at least one convolutional nodes (e.g., a plurality of convolutional nodes). In some embodiments, the convolutional neural network(s) may further include an input layer and an output layer. For example, the ECG signal(s) may include a plurality of ECG signal samples. Additionally or alternatively, the input layer may include at least one node for each ECG signal sample of the plurality of ECG signal samples (or a subset thereof, e.g., associated with a predetermined time period, a buffer size of a buffer for ECG signal samples, and/or the like). Additionally or alternatively, the input layer may further include at least one input for non-ECG biometric data associated with sensors (e.g., of heart monitoring device 202a and/or the like), as described herein. In some embodiments, an output of the output layer may include an indication of the time data corresponding to the arrhythmia type. Additionally or alternatively, an output of the output layer may include a confidence score, a plausibility score, and/or the like, as described herein. In some embodiments, the neural network(s) may include a plurality of Siamese branches (e.g., each respective Siamese branch associated with a respective ECG channel), as described herein.

As shown in FIG. 2A, at 232a, remote computer system 204a may communicate a trained rhythm change classifier (or a plurality of weights thereof) to heart monitoring device 202a and/or gateway device 229a, as described herein. In some embodiments, after training, a plurality of weights corresponding to the trained rhythm change classifier may be communicated to heart monitoring device 202a and/or gateway device 229a. Additionally or alternatively, a copy of the trained rhythm change classifier (or a plurality of weights thereof) may be downloaded from remote computer system 204a and/or installed on (e.g., uploaded to, written to, configured on, and/or the like) at least one non-transitory computer readable medium (e.g., e.g., a memory, a programmable circuit board, a field programmable gate array (FPGA), an integrated circuit, any combination thereof, and/or the like), which may be installed in and/or part of heart monitoring device 202a and/or gateway device 229a.

In some embodiments, heart monitoring device 202a may be an external heart monitoring device for a patient, as described herein. For example, (external) heart monitoring device 202a may include a plurality of ECG electrodes configured to sense surface ECG activity of the patient. Additionally or alternatively, (external) heart monitoring device 202a may include ECG processing circuitry configured to process the surface ECG activity of the patient to provide at least one ECG signal for the patient on at least one ECG channel.

In some embodiments, (external) heart monitoring device 202a may include a non-transitory computer-readable medium (e.g., a memory, a programmable circuit board, a field programmable gate array, an integrated circuit, any combination thereof, and/or the like) including (e.g., implementing, embodying, storing, and/or the like) the trained rhythm change classifier (which may include, e.g., at least one neural network trained based on the historical collection of a plurality of ECG signal portions with known rhythm change information), as described herein. Additionally or alternatively, (external) heart monitoring device 202a may include at least one processor operatively connected to the ECG channel(s) and/or the non-transitory computer-readable medium.

In some embodiments, gateway device 229a may include a non-transitory computer-readable medium (e.g., a memory, a programmable circuit board, a field programmable gate array, an integrated circuit, any combination thereof, and/or the like) including (e.g., implementing, embodying, storing, and/or the like) the trained rhythm change classifier (which may include, e.g., at least one neural network trained based on the historical collection of a plurality of ECG signal portions with known rhythm change information), as described herein. Additionally or alternatively, gateway device 229a may include at least one processor operatively connected to the non-transitory computer-readable medium.

In some embodiments, heart monitoring device 202a (e.g., the processor(s) thereof) may be configured to receive the ECG signal(s) via the ECG channel(s). Additionally or alternatively, heart monitoring device 202a (e.g., the processor(s) thereof) may be configured to detect with the rhythm change classifier time data corresponding to a predetermined rhythm change in the at least one ECG signal. For example, the predetermined rhythm change may be associated with an arrhythmia (e.g., a change in heart rate, atrial fibrillation, flutter, supraventricular tachycardia, ventricular tachycardia, pause, AV block, ventricular fibrillation, bigeminy, trigeminy, ventricular ectopic beats, bradycardia, tachycardia, a change in morphology of the at least one ECG signal, any combination thereof, and/or the like). Additionally or alternatively, the time data may include at least one of a start time, a time interval, any combination thereof, and/or the like. In some embodiments, heart monitoring device 202a (e.g., the processor(s) thereof) may be configured to determine based on the detected time data at least one ECG signal portion associated with the detected time data corresponding to the predetermined rhythm change in the ECG signal(s).

In some embodiments, heart monitoring device 202a (e.g., the processor(s) thereof) may be configured to receive the ECG signal(s) via the ECG channel(s). Additionally or alternatively, heart monitoring device 202a (e.g., the processor(s) thereof) may be configured to transmit the ECG signal(s) to gateway device 229a. In some embodiments, gateway device 229a (e.g., the processor(s) thereof) may be configured to detect with the rhythm change classifier time data corresponding to a predetermined rhythm change in the ECG signal(s). For example, the predetermined rhythm change may be associated with an arrhythmia (e.g., a change in heart rate, atrial fibrillation, flutter, supraventricular tachycardia, ventricular tachycardia, pause, AV block, ventricular fibrillation, bigeminy, trigeminy, ventricular ectopic beats, bradycardia, tachycardia, a change in morphology of the at least one ECG signal, any combination thereof, and/or the like), as described herein. Additionally or alternatively, the time data may include at least one of a start time, a time interval, any combination thereof, and/or the like. In some embodiments, gateway device 229a (e.g., the processor(s) thereof) may be configured to determine based on the detected time data at least one ECG signal portion associated with the detected time data corresponding to the predetermined rhythm change in the ECG signal(s).

In some embodiments, the ECG signal portion(s) may have a duration greater than or equal to 15 seconds and less than or equal to 120 seconds (e.g., based on a predetermined time interval, a buffer size of a buffer for ECG signal samples, and/or the like). For example, the ECG signal portion(s) may have a duration greater than or equal to 15 seconds and less than or equal to 60 seconds. In some embodiments, the ECG signal portion(s) may have a duration of between 15 seconds and 180 seconds. In some embodiments, the ECG signal portion(s) may have a duration of between 15 seconds and 240 seconds. In some embodiments, the ECG signal portion(s) may have a duration of between 15 seconds and 480 seconds. In some embodiments, the ECG signal portion(s) may have a duration of between 15 seconds and 1000 seconds. In some embodiments, the duration of the ECG signal portion(s) may be specified via a user input via a user interface control (e.g., of heart monitoring device 202a, gateway device 229a, and/or the like).

In some embodiments, the ECG signal(s) comprises a plurality of ECG signal samples. For example, the ECG signal sample(s) may be sampled at a rate between 10 Hz and 1000 Hz (e.g., greater than or equal to 10 Hz and less than or equal to 1000 Hz), a rate between 100 Hz and 500 Hz (e.g., greater than or equal to 100 Hz and less than or equal to 500 Hz), and/or the like.

In some embodiments, the ECG channel(s) may include a plurality of ECG channels (e.g., channels of a standard 12-lead ECG system, a subset thereof, and/or the like). Additionally or alternatively, the ECG signal(s) may include at least one respective ECG signal associated with each respective ECG channel. In some embodiments, the plurality of ECG channels may include a first ECG channel and a second ECG channel Additionally or alternatively, the ECG signal(s) may include a first respective ECG signal associated with the first ECG channel and a second respective ECG signal associated with the second ECG channel. In some embodiments, the first respective ECG signal may be substantially orthogonal to the second respective ECG signal. For example, the first ECG channel may be associated with a first electrode positioned proximate a front of the patient and a second electrode positioned proximate a back of the patient (e.g., a front-to-back (FB) channel). Additionally or alternatively, the second ECG channel may be associated with a third electrode positioned proximate a first side of the patient and a fourth electrode positioned proximate a second side of the patient (e.g., a side-to-side (SS) channel). Additionally or alternatively, the FB channel may be orthogonal to the SS channel (e.g., a first hypothetical line connecting the first electrode to the second electrode may be substantially (e.g., approximately and/or the like) orthogonal (e.g., perpendicular and/or the like) to a second hypothetical line connecting the third electrode to the fourth electrode, the second hypothetical line may have a component (e.g., vector component, vector projection, and/or the like that may be calculated and/or the like) that is orthogonal to the first hypothetical line, and/or the like).

In some embodiments, the neural network(s) of the rhythm change classifier (e.g., of heart monitoring device 202a and/or gateway device 229a) may include a plurality of Siamese branches. Additionally or alternatively, each respective Siamese branch may be associated with a respective ECG channel (e.g., of the plurality of ECG channels). In some embodiments, the neural network(s) of the rhythm change classifier may further include at least one further layer connected to the plurality of Siamese branches. In some non-limiting embodiments, each Siamese branch of the plurality of Siamese branches may include a plurality of convolutional layers. Additionally or alternatively, dimensions of each of the plurality of convolutional layers of each respective Siamese branch may be the same as the dimensions of each of the plurality of convolutional layers of each other Siamese branch (e.g., convolutional layers of all Siamese branches may have the same dimensions).

In some embodiments, heart monitoring device 202a and/or gateway device 229a (e.g., processor(s) thereof) may be further configured to detect (e.g., with the trained rhythm change classifier) the predetermined rhythm change based on the at least one ECG signal. In some embodiments, heart monitoring device 202a may further include at least one sensor and associated sensor circuitry configured to sense non-ECG biometric data of the patient (which, in some embodiments, may be communicated to gateway device 229a). Additionally or alternatively, detecting the predetermined rhythm change may be further based on the non-ECG biometric data of the patient (e.g., non-ECG biometric data of the patient may be input into the neural network(s) of the rhythm change classifier, may be combined with the output of the rhythm change classifier, and/or the like). In some embodiments, the at least one sensor may include at least one of an accelerometer, a heart sound detector, a receiver for electromagnetic (e.g., RF) waves (e.g., antenna and/or the like), any combination thereof, and/or the like. Additionally or alternatively, the non-ECG biometric data may include at least one of acceleration data, heart sound data, electromagnetic (e.g., RF) waves scattered and/or reflected from internal tissues, any combination thereof, and/or the like.

In some embodiments, detecting the predetermined rhythm change may be further based on at least one baseline ECG signal portion of the patient. For example, the baseline ECG signal portion(s) may be obtained (e.g., measured, recorded, stored, and/or the like) using high accuracy ECG measurements (e.g., from an ECG device separate from the heart monitoring device 202a, such as a 12-lead ECG sensor and/or the like) when a patient visits a clinic. Additionally or alternatively, the baseline ECG signal portion(s) may be obtained (e.g., measured, recorded, stored, and/or the like) using heart monitoring device 202a (and/or gateway device 229a) during time periods of known and/or expected rest (e.g., night hours and/or the like). Additionally or alternatively, the baseline ECG signal portion(s) may be obtained (e.g., measured, recorded, stored, and/or the like) using heart monitoring device 202a (and/or gateway device 229a) during time periods of normal sinus rhythm.

In some embodiments, detecting the predetermined rhythm change may be further based on at least one calibration measurement of the patient. For example, the calibration measurement may be based on at least one second ECG signal from second surface ECG activity sensed by a second plurality of ECG electrodes, which may be independent of the plurality of ECG electrodes of (external) heart monitoring device 202a. For example, the calibration measurement may be obtained (e.g., measured, recorded, stored, and/or the like) using high accuracy ECG measurements (e.g., from an ECG device separate from the heart monitoring device 202a, such as a 12-lead ECG sensor and/or the like) when a patient visits a clinic.

In some embodiments, detecting the predetermined rhythm change may be further based on at least one reference vector of the patient. For example, the reference vector may include a vector determined (e.g., calculated and/or the like) based on an aggregation of a plurality of past measurements (e.g., past ECG signal portions and/or the like). In some embodiments, heart monitoring device 202a (and/or gateway device 229a) may determine the reference vector with a reference-extraction neural network based on the past measurements (e.g., past ECG signal portions and/or the like).

In some embodiments, detecting the predetermined rhythm change may be further based on at least one previous ECG signal portion. For example, at least one vector may be determined (e.g., calculated and/or the like) based on an aggregation of a plurality of previous ECG signal portions (e.g., from at least one previous time period). In some embodiments, a plurality of vectors may be determined (e.g., calculated and/or the like) based on an aggregation of a plurality of previous ECG signal portions from each of a plurality of previous time periods (e.g., a previous day, a previous week, a previous month, and/or the like). In some embodiments, each vector may be determined (e.g., by heart monitoring device 202a and/or gateway device 229a) with a reference-extraction neural network based on the past measurements (e.g., past ECG signal portions and/or the like).

In some embodiments, a gateway device 229a may enable communication between heart monitoring device 202a and remote computer system 204a, as described herein. For example, remote computer system 204a may communicate the trained rhythm change classifier to gateway device 229a. Additionally or alternatively, gateway device 229a may store the trained rhythm change classifier and/or communicate the trained rhythm change classifier to heart monitoring device 202a. In some embodiments, gateway device 229a may store the trained rhythm change classifier (and/or a plurality of weights corresponding thereto). Additionally or alternatively, gateway device 229a may be configured to use the trained rhythm change classifier to perform the rhythm change classification, as described herein. For example, gateway device 229a may be configured to receive the ECG signal(s) from heart monitoring device 202a (e.g., continuously, periodically, and/or the like), process the ECG signal (s) from heart monitoring device 202a based on the trained rhythm change classifier, and/or communicate (e.g., transmit and/or the like) determined/identified ECG signal portion(s)

corresponding to the predetermined rhythm change rhythm change(s) to remote computer system 204a.

In some embodiments, the processor (e.g., of heart monitoring device 202a) may further determine (e.g., with the rhythm change classifier) a confidence score associated with the predetermined rhythm change based on the at least one ECG signal. For example, an output of at least one neural network of the rhythm change classifier may include the confidence score (e.g., a probability that the determined ECG signal portion(s) contain a predetermined rhythm change and/or the like). In some embodiments, the rhythm change classifier may include a plurality of neural networks, and each such neural network may output a prediction value associated with at least one predetermined rhythm change. Additionally or alternatively, such outputs may be combined (e.g., aggregated and/or the like) and/or the confidence score may be calculated based on such outputs.

As shown in FIG. 2A, at 234a, heart monitoring device 202a and/or gateway device 229a (e.g., the processor(s) thereof) may communicate (e.g., transmit and/or the like) the determined ECG signal portion(s) to remote computer system 204a, as described herein. Additionally or alternatively, heart monitoring device 202a and/or gateway device 229a (e.g., the processor(s) thereof) may be configured to detect and/or communicate an indication (e.g., a flag, an indicator, a confidence score, a mark, metadata, the time data, and/or the like) associated with the predetermined rhythm change detected (e.g., identified and/or the like) in the ECG signal portion(s).

In some embodiments, the processor (e.g., of heart monitoring device 202a and/or gateway device 229a) may further communicate (e.g., transmit and/or the like) at least one second ECG signal portion of the ECG signal(s) to remote computer system 204a. Additionally or alternatively, the second ECG signal portion(s) may be independent of the detected time data corresponding to the predetermined rhythm change in the ECG signal(s). In some embodiments, the processor (e.g., of heart monitoring device 202a and/or gateway device 229a) may randomly determine the second ECG signal portion(s) (e.g., randomly sample the ECG signal(s) to determine the second ECG signal portion(s)). In some embodiments, the processor (e.g., of heart monitoring device 202a and/or gateway device 229a) may determine, with the rhythm change classifier, a first confidence score associated with the predetermined rhythm change based on the ECG signal(s), and the first confidence score may be above a first threshold. Additionally or alternatively, the processor (e.g., of heart monitoring device 202a and/or gateway device 229a) may detect, with the rhythm change classifier, second time data corresponding to a potential rhythm change in the ECG signal(s) (e.g., the second time data may include at least one of a second start time, a second time interval, any combination thereof, and/or the like). Additionally or alternatively, the processor (e.g., of heart monitoring device 202a and/or gateway device 229a) may determine, with the rhythm change classifier, a second confidence score associated with the potential rhythm change based on the ECG signal(s), and the second confidence score may be below the first threshold and above a second threshold. Additionally or alternatively, the processor (e.g., of heart monitoring device 202a and/or gateway device 229a) may determine, based on the detected second time data, the second ECG signal portion(s) associated with the detected second time data corresponding to the potential rhythm change in the ECG signal(s).

In some embodiments, gateway device 229a may enable communication between heart monitoring device 202a and remote computer system 204a, as described herein. For example, transmitting the determined ECG signal portion(s) to remote computer system 204a may include heart monitoring device 202a communicating (e.g., transmitting and/or the like) the determined ECG signal portion(s) to gateway device 229a. Additionally or alternatively, gateway device 229a may be configured to receive the determined ECG signal portion(s) from heart monitoring device 202a and/or communicate the determined ECG signal portion(s) to remote server 204a.

In some embodiments, remote computing system 204a may receive the determined ECG signal portion(s) (e.g., from heart monitoring device 202a and/or gateway device 229a). Additionally or alternatively, remote computing system 204a may analyze the determined ECG signal portion(s) to classify a type of arrhythmia for the rhythm change(s) in the ECG signal(s). In some embodiments, the type of arrhythmia may include at least one of a change in heart rate, atrial fibrillation, flutter, supraventricular tachycardia, ventricular tachycardia, pause, AV block, ventricular fibrillation, bigeminy, trigeminy, ventricular ectopic beats, bradycardia, tachycardia, a change in morphology of the at least one ECG signal, any combination thereof, and/or the like.

In some embodiments, remote computer system 204a may include an arrhythmia type classifier (e.g., including at least one (second) neural network trained based on a (second) historical collection of a (second) plurality of ECG signal portions with known arrhythmia type information), as described herein. Additionally or alternatively, analyzing the at least one determined ECG signal portion may include remote computer system 204a detecting with the arrhythmia type classifier the type of arrhythmia associated with the rhythm change based on the determined ECG signal portion(s).

In some embodiments, onset of bradycardia may include a patient's heart rate dropping below a first threshold for the patient. For example, the first threshold may include a value of at least 20 beats per minute (BPM) and up to 100 BPM, a value of at least 30 BPM and up to 100 BPM, and/or the like, which may be calculated over a predetermined interval (e.g., a number of heartbeats, such as 16 beats and/or the like). For example, a default first threshold may include 40 BPM, and the first threshold may be adjusted for each individual patient (e.g., by a prescriber, treating physician, and/or the like). In some embodiments, offset of bradycardia may include a patient's heart rate rising above a second threshold for the patient. For example, the second threshold may include a value of at least 20 beats per minute (BPM) and up to 100 BPM, which may be calculated over a predetermined interval (e.g., a number of heart beats, such as 16 beats and/or the like). For example, a default second threshold may include 45 BPM, and the second threshold may be adjusted for each individual patient (e.g., by a prescriber, treating physician, and/or the like). In some embodiments, a patient must remain in bradycardia for a first selected time period before the rhythm change is reported (e.g., before the ECG signal portion(s) are classified as bradycardia, before any messages associated with the ECG signal portion(s) are communicated, and/or the like). For example, the first selected time period may include a value of at least 0 seconds and up to 600 seconds, a value of at least 15 second and up to 600 seconds, and/or the like. For example, a default first time period may include 30 seconds, and the first time period may be adjusted for each individual patient (e.g., by a prescriber, treating physician, and/or the like).

In some embodiments, onset of tachycardia may include a patient's heart rate rising above a third threshold for the patient. For example, the third threshold may include a value of at least 100 BPM and up to 250 BPM, a value of at least 100 BPM and up to 249 BPM, and/or the like, which may be calculated over a predetermined interval (e.g., a number of heartbeats, such as 16 beats and/or the like). For example, a default third threshold may include 1300 BPM, and the third threshold may be adjusted for each individual patient (e.g., by a prescriber, treating physician, and/or the like). In some embodiments, offset of tachycardia may include a patient's heart rate dropping below a fourth threshold for the patient. For example, the fourth threshold may include a value of at least 100 BPM and up to 250 BPM, a value of at least 100 BPM and up to 249 BPM, and/or the like, which may be calculated over a predetermined interval (e.g., a number of heart beats, such as 16 beats and/or the like). For example, a default fourth threshold may include 110 BPM, and the fourth threshold may be adjusted for each individual patient (e.g., by a prescriber, treating physician, and/or the like). In some embodiments, a patient must remain in tachycardia for a second selected time period before the rhythm change is reported (e.g., before the ECG signal portion(s) are classified as tachycardia, before any messages associated with the ECG signal portion(s) are communicated, and/or the like). For example, the second selected time period may include a value of at least 0 seconds and up to 600 seconds, a value of at least 15 second and up to 600 seconds, and/or the like. For example, a default second time period may include 30 seconds, and the second time period may be adjusted for each individual patient (e.g., by a prescriber, treating physician, and/or the like).

In some embodiments, onset of atrial fibrillation may include a quivering or irregular heartbeat of a patient. In some embodiments, a patient must remain in atrial fibrillation for a third selected time period before the rhythm change is reported (e.g., before the ECG signal portion(s) are classified as atrial fibrillation, before any messages associated with the ECG signal portion(s) are communicated, and/or the like). For example, the third selected time period may include a value of at least 0 minutes and up to 60 minutes and/or the like. For example, a default third time period may include 5 minutes, and the third time period may be adjusted for each individual patient (e.g., by a prescriber, treating physician, and/or the like).

In some embodiments, onset of cardiac pause may include a prolonged R-R interval that represents the interruption in ventricular depolarization. In some embodiments, a patient must remain in cardiac pause for a fourth selected time period before the rhythm change is reported (e.g., before the ECG signal portion(s) are classified as cardiac pause, before any messages associated with the ECG signal portion(s) are communicated, and/or the like). For example, the fourth selected time period may include a value of at least 1500 milliseconds (ms) and up to 15000 ms and/or the like. For example, a default fourth time period may include 3000 ms, and the fourth time period may be adjusted for each individual patient (e.g., by a prescriber, treating physician, and/or the like).

In some embodiments, onset of bradycardia rate change may include a patient's heart rate dropping at least a first predetermined value below the first threshold. In some embodiments, each time the patient's heart rate drops by at least an integer multiple of the first predetermined value, the rhythm change may be reported (e.g., the ECG signal portion(s) may be classified as bradycardia rate change, messages associated with the ECG signal portion(s) may be communicated, and/or the like). For example, the first predetermined value may include a value of at least 0 BPM and up to 100 BPM and/or the like. For example, a default first predetermined value may 5 BPM, and the first predetermined value may be adjusted for each individual patient (e.g., by a prescriber, treating physician, and/or the like).

In some embodiments, onset of tachycardia rate change may include a patient's heart rate rising at least a second predetermined value above the third threshold. In some embodiments, each time the patient's heart rate rises by at least an integer multiple of the second predetermined value, the rhythm change may be reported (e.g., the ECG signal portion(s) may be classified as tachycardia rate change, messages associated with the ECG signal portion(s) may be communicated, and/or the like). For example, the second predetermined value may include a value of at least 0 BPM and up to 250 BPM and/or the like. For example, a default first predetermined value may 10 BPM, and the second predetermined value may be adjusted for each individual patient (e.g., by a prescriber, treating physician, and/or the like).

In some embodiments, remote computer system 204a may analyze the determined ECG signal portion(s) to identify at least one arrhythmia associated with the rhythm change in the at least one ECG signal. In some embodiments, the arrhythmia may be one or more rare arrhythmias on which the remote computer system 204a may have previously been trained. Additionally or alternatively, remote computer system 204a may use any suitable signal processing technique (e.g., separate from or including the arrhythmia type classifier as described herein) to identify the rare arrhythmia(s). For example, such a small portion of the historical collection of ECG signal portions may be associated with the rare arrhythmia(s) that the arrhythmia type classifier may not be sufficiently trained to classify such rare arrhythmia(s). Additionally or alternatively, remote computer system 204a may use signal processing techniques, predetermined rules, and/or the like to identify such rare arrhythmia(s).

In some embodiments, the determined ECG signal portion(s) may include a plurality of determined ECG signal portions. Additionally or alternatively, remote computer system 204a may receive the plurality of determined ECG signal portions from heart monitoring device 202a and/or gateway device 229a, as described herein. In some embodiments, remote computer system 204a may analyze each respective determined ECG signal portion to classify a respective class for each respective determined ECG signal portion. Additionally or alternatively, the class for at least two respective determined ECG signal portions may include a first class (e.g., at least two ECG signal portions may belong to the same class/grouping). In some embodiments, analyzing each respective determined ECG signal portion may include determining (e.g., calculating and/or the like) a vector for each respective determined ECG signal portion. Additionally or alternatively, the vectors may be classified into classes (e.g., groups, clusters, and/or the like) based on similarity between the respective vectors (e.g., vector distance, clustering, and/or the like).

As shown in FIG. 2A, at 236a, remote computer system 204a may communicate (e.g., transmit and/or the like) at least one message associated with the determined ECG signal portion(s) and/or the type of arrhythmia associated with the rhythm change, as described herein. For example, the message(s) may be communicated from remote computer system 204a to technician device 208a, as described herein.

In some embodiments, remote computer system 204*a* may transmit at least one message associated with the second ECG signal portion(s) (e.g., randomly determined second ECG signal portion(s), second ECG signal portion(s) determined to have a confidence score below a first threshold and above a second threshold, and/or the like, as described herein) to technician device 208*a*.

In some embodiments, remote computer system 204*a* may transmit at least one message associated with the at least two respective determined ECG signal portions and the first class to technician device 208*a*. For example, a technician using technician device 208*a* may be able to review the at least two respective determined ECG signal portions more efficiently, rapidly, and/or the like, since similar ECG signal portions are grouped together in the same class (e.g., the first class).

As shown in FIG. 2A, at 238*a*, remote computer system 204*a* may receive annotation data associated with at least one annotation from technician device 208*a*, as described herein. For example, the annotation data may be communicated from technician device 208*a* to remote computer system 204*a*, as described herein. Additionally or alternatively, the ECG signal portion(s) associated with such annotation(s) may be communicated with the annotation data, as described herein.

In some embodiments, remote computer system 204*a* may receive (e.g., from technician device 208*a*) annotation data associated with at least one annotation for the second ECG signal portion(s) (e.g., randomly determined second ECG signal portion(s), second ECG signal portion(s) determined to have a confidence score below a first threshold and above a second threshold, and/or the like, as described herein). In some embodiments, remote computer system 204*a* may retrain the rhythm change classifier (and/or train an updated rhythm change classifier) based on the historical collection of the plurality of ECG signal portions with the known rhythm change information, the second ECG signal portion(s), and the annotation data associated therewith. In some embodiments, remote computer system 204*a* may retrain the arrhythmia type classifier based on the historical collection of the plurality of ECG signal portions with the known rhythm change information, the second ECG signal portion(s), and the annotation data associated therewith.

As shown in FIG. 2A, at 240*a*, remote computer system 204*a* may communicate (e.g., transmit, write, and/or the like) the annotation data to data repository 206*a*, as described herein. Additionally or alternatively, the ECG signal portion(s) associated with such annotation(s) may be communicated with the annotation data, as described herein.

In some embodiments, annotation data and the ECG signal portion(s) associated with such annotation(s) may be added to the historical collection of the plurality of ECG signal portions. For example, the annotation data may be stored as the known rhythm change information and/or the known arrhythmia type information for the ECG signal portion(s) associated with such annotation(s). In some embodiments, remote computer system 204*a* may retrain the rhythm change classifier (and/or train an updated rhythm change classifier) based on the historical collection of the plurality of ECG signal portions with the known rhythm change information (which may now include the ECG signal portion(s) and/or the annotation data associated therewith). In some embodiments, remote computer system 204*a* may retrain the arrhythmia type classifier based on the historical collection of the plurality of ECG signal portions with the known arrhythmia type information (which may now include the ECG signal portion(s) and/or the annotation data associated therewith).

In some embodiments, remote computer system 204*a* may add annotation data associated with at least one annotation for the second ECG signal portion(s) (e.g., randomly determined second ECG signal portion(s), second ECG signal portion(s) determined to have a confidence score below a first threshold and above a second threshold, and/or the like, as described herein) to the historical collection of the plurality of ECG signal portions in data repository 206*a*. In some embodiments, remote computer system 204*a* may retrain the rhythm change classifier (and/or train an updated rhythm change classifier) based on the historical collection of the plurality of ECG signal portions with the known rhythm change information (which may now include the second ECG signal portion(s) and/or the annotation data associated therewith). In some embodiments, remote computer system 204*a* may retrain the arrhythmia type classifier based on the historical collection of the plurality of ECG signal portions with the known arrhythmia type information (which may now include the second ECG signal portion(s) and/or the annotation data associated therewith).

As shown in FIG. 2A, at 242*a*, remote computer system 204*a* may communicate the retrained rhythm change classifier (and/or trained updated rhythm change classifier) to heart monitoring device 202*a* and/or gateway device 229*a*, as described herein. Additionally or alternatively, a copy of the retrained rhythm change classifier (and/or trained updated rhythm change classifier) may be downloaded from remote computer system 204*a* and/or installed on (e.g., uploaded to, written to, configured on, and/or the like) at least one non-transitory computer readable medium (e.g., e.g., memory, programmable circuit board, FPGA, integrated circuit, any combination thereof, and/or the like), which may be installed in and/or part of heart monitoring device 202*a* and/or gateway device 229*a*.

Figure 2B:
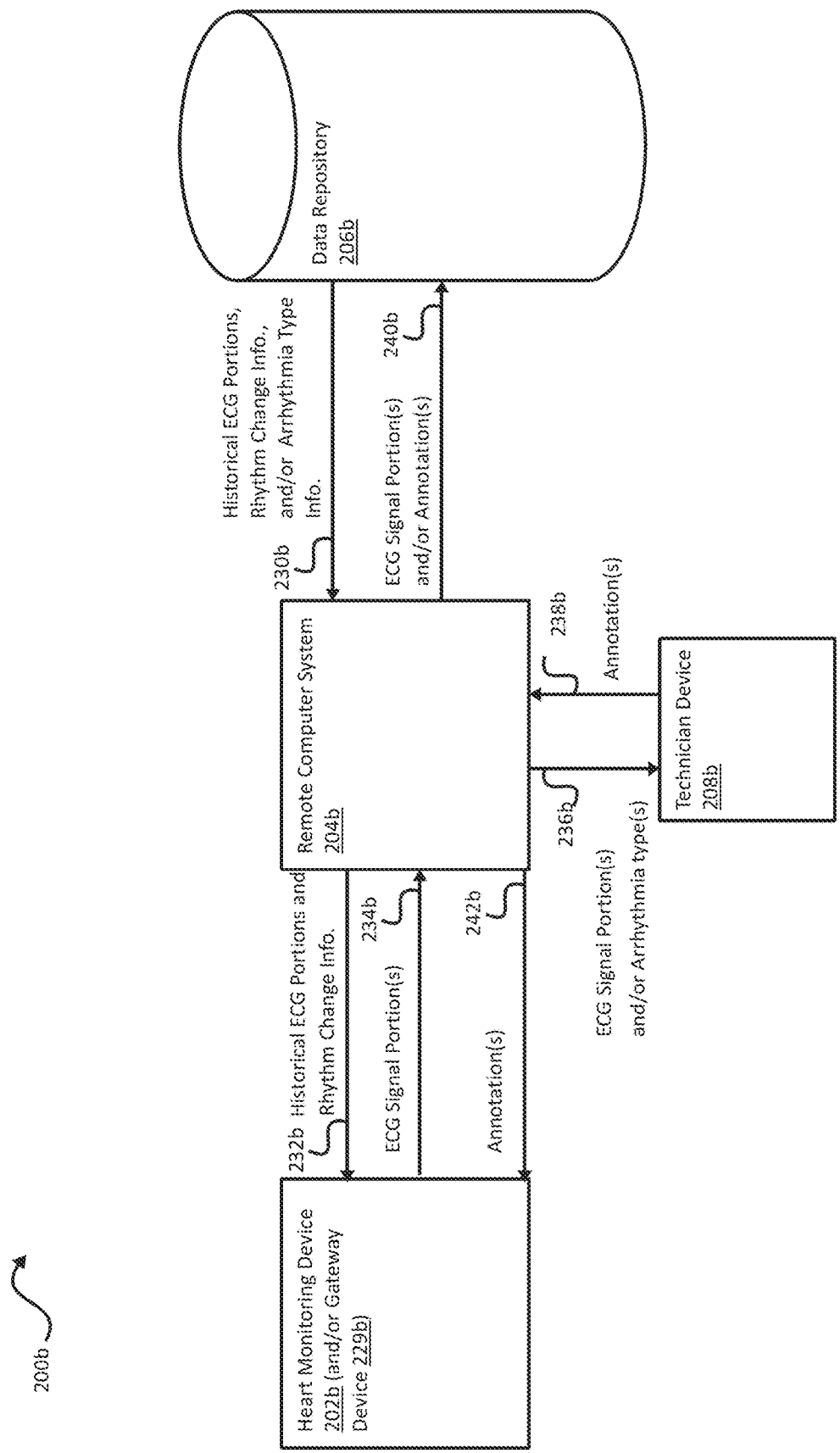

Referring now to FIG. 2B, FIG. 2B shows an example block diagram of a system architecture 200*b* for arrhythmia monitoring, according to some embodiments. In addition to system components, the system architecture 200*b* also shows data flows between the system components. As shown in FIG. 2B, system architecture 200*b* may include heart monitoring device 202*b*, remote computer system 204*b*, data repository 206*b*, technician device 208*b*, and/or gateway device 229*b*. In some embodiments, heart monitoring device 202*b* may be the same as or similar to heart monitoring device 102, heart monitoring device 202*a*, and/or the like. In some embodiments, remote computer system 204*b* may be the same as or similar to remote computer system 104 (e.g., one or more devices of remote computer system 104), remote computer system 204*a* (e.g., one or more devices of remote computer system 204*a*), and/or the like. In some embodiments, data repository 206*b* may be the same as or similar to data repository 106 (e.g., one or more devices of data repository 106), data repository 206*a* (e.g., one or more devices of data repository 206*a*), and/or the like. In some embodiments, technician device 208*b* may be the same as or similar to technician device 108, technician device 208*a*, and/or the like. In some embodiments, gateway device 229*b* may be the same as or similar to gateway device 129.

As shown in FIG. 2B, at 230*b*, remote computer system 204*b* may receive (e.g., retrieve, search for, send a request and/or query to cause data repository 206*b* to communicate, and/or the like) a historical collection of a plurality of ECG signal portions and information related thereto (e.g., known rhythm change information, known arrhythmia type information, and/or the like), e.g., from data repository 206b, as described herein. In some embodiments, remote computer system 204b may train at least one neural network of at least one classifier (e.g., an arrhythmia type classifier and/or the like) based on the historical collection of a plurality of ECG signal portions and information related thereto (e.g., known arrhythmia type information and/or the like), as described herein.

In some embodiments, an arrhythmia type classifier may include at least one neural network (e.g., at least one second neural network), as described herein. Additionally or alternatively, the at least one (second) neural network may include at least one of a deep neural network, a convolutional neural network, a recurrent neural network, an attention network, a fully connected neural network, any combination thereof, and/or the like. For example, the neural network(s) may include at least one convolutional neural network having a plurality of convolutional layers. In some embodiments, the convolutional neural network(s) may include between five and 40 convolutional layers (e.g., at least five convolutional layers and up to 40 convolutional layers). For example, the convolutional neural network(s) may include between seven and ten convolutional layers (e.g., at least seven convolutional layers and no more than ten convolutional layers). In some embodiments, each convolutional layer may include at least one convolutional nodes (e.g., a plurality of convolutional nodes). In some embodiments, the convolutional neural network(s) may further include an input layer and an output layer. For example, the ECG signal(s) may include a plurality of ECG signal samples. Additionally or alternatively, the input layer may include at least one node for each ECG signal sample of the plurality of ECG signal samples (or a subset thereof, e.g., associated with a predetermined time period, a buffer size of a buffer for ECG signal samples, and/or the like). Additionally or alternatively, the input layer may further include at least one input for non-ECG biometric data associated with sensors (e.g., of heart monitoring device 202 and/or the like), as described herein. In some embodiments, an output of the output layer may include an indication of the time data corresponding to the arrhythmia type. Additionally or alternatively, an output of the output layer may include a confidence score, a plausibility score, and/or the lie, as described herein. In some embodiments, the neural network(s) may include a plurality of Siamese branches (e.g., each respective Siamese branch associated with a respective ECG channel), as described herein.

In some embodiments, remote computer system 204b may train an arrhythmia type classifier by generating, with the arrhythmia type classifier, a predicted type of arrhythmia in each respective ECG signal portion of the historical collection of the plurality of ECG signal portions (or a second plurality thereof), determining at least one error value based on the predicted type of arrhythmia and the known arrhythmia type information (e.g., a respective annotations associated with a known type of arrhythmia for each respective ECG signal portion), and updating the arrhythmia type classifier (e.g., updating the weights thereof and/or the like) based on the error value(s) (e.g., using back propagation and/or the like). In some embodiments, the error value(s) may include one of a prediction error or a contrastive loss.

As shown in FIG. 2B, at 232b, remote computer system 204b may communicate a historical collection of a plurality of ECG signal portions and information related thereto (e.g., known rhythm change information and/or the like) to heart monitoring device 202b and/or gateway device 229b, as described herein. Additionally or alternatively, heart monitoring device 202b and/or gateway device 229b may train a rhythm change classifier, which may be implemented by at least one non-transitory computer readable medium (e.g., e.g., a memory, a programmable circuit board, a field programmable gate array (FPGA), an integrated circuit, any combination thereof, and/or the like) that may be installed in and/or part of heart monitoring device 202b and/or gateway device 229b, as described herein.

In some embodiments, heart monitoring device 202b may be an external heart monitoring device for a patient, as described herein. For example, (external) heart monitoring device 202b may include a plurality of ECG electrodes configured to sense surface ECG activity of the patient. Additionally or alternatively, (external) heart monitoring device 202b may include ECG processing circuitry configured to process the surface ECG activity of the patient to provide at least one ECG signal for the patient on at least one ECG channel.

In some embodiments, (external) heart monitoring device 202b may include a non-transitory computer-readable medium (e.g., a memory, a programmable circuit board, a field programmable gate array, an integrated circuit, any combination thereof, and/or the like) including (e.g., implementing, embodying, storing, and/or the like) the rhythm change classifier (which may include, e.g., at least one neural network), as described herein. Additionally or alternatively, (external) heart monitoring device 202b may include at least one processor operatively connected to the ECG channel(s) and the non-transitory computer-readable medium.

In some embodiments, gateway device 229b may include a non-transitory computer-readable medium (e.g., a memory, a programmable circuit board, a field programmable gate array, an integrated circuit, any combination thereof, and/or the like) including (e.g., implementing, embodying, storing, and/or the like) the rhythm change classifier (which may include, e.g., at least one neural network), as described herein. Additionally or alternatively, gateway device 229b may include at least one processor operatively connected to the non-transitory computer-readable medium.

In some embodiments, a rhythm change classifier may include at least one neural network, as described herein. Additionally or alternatively, the at least one neural network may include at least one of a convolutional neural network, a recurrent neural network, an attention network, a fully connected neural network, any combination thereof, and/or the like, as described herein. For example, the neural network(s) may include at least one convolutional neural network having a plurality of convolutional layers. In some embodiments, the convolutional neural network(s) may include between five and 40 convolutional layers (e.g., at least five convolutional layers and up to 40 convolutional layers). For example, the convolutional neural network(s) may include between seven and ten convolutional layers (e.g., at least seven convolutional layers and no more than ten convolutional layers). In some embodiments, each convolutional layer may include at least one convolutional nodes (e.g., a plurality of convolutional nodes). In some embodiments, the convolutional neural network(s) may further include an input layer and an output layer. For example, the ECG signal(s) may include a plurality of ECG signal samples. Additionally or alternatively, the input layer may include at least one node for each ECG signal sample of the plurality of ECG signal samples (or a subset thereof, e.g., associated with a predetermined time period, a buffer size of a buffer for ECG signal samples, and/or the like). Additionally or alternatively, the input layer may further include at least one input for non-ECG biometric data associated with each sensor of heart monitoring device 202b, as described herein. In some embodiments, an output of the output layer may include an indication of the time data corresponding to the rhythm change. Additionally or alternatively, an output of the output layer may include a confidence score, as described herein. In some embodiments, the neural network(s) may include a plurality of Siamese branches (e.g., each respective Siamese branch associated with a respective ECG channel), as described herein.

In some embodiments, heart monitoring device 202b and/or gateway device 229b may train the rhythm change classifier by generating, with the rhythm change classifier, predicted rhythm change information (e.g., data (e.g., probability, confidence score, and/or the like) associated with a predicted rhythm change, data (e.g., probability, confidence score, and/or the like) associated with a lack of a predicted rhythm change, and/or the like) for each ECG signal portion of the historical collection of the plurality of ECG signal portions, determining at least one error value based on the predicted rhythm change information and the known rhythm change information, and updating the rhythm change classifier (e.g., updating the weights thereof and/or the like) based on the error value(s) (e.g., using back propagation and/or the like). In some embodiments, the error value(s) may include one of a prediction error or a contrastive loss.

In some embodiments, the historical collection of the plurality of ECG signal portions may include a first ECG signal portion associated with a first time and a second ECG signal portion associated with a second time after the first time. Additionally or alternatively, heart monitoring device 202b and/or gateway device 229b may train the rhythm change classifier by generating, with the rhythm change classifier, a predicted ECG signal portion associated with the second time based on the first ECG signal portion, determining at least one error value based on the predicted ECG signal portion and the second ECG signal portion, and updating the rhythm change classifier (e.g., updating the weights thereof and/or the like) based on the error value(s) (e.g., using back propagation and/or the like). In some embodiments, the error value(s) may include one of a prediction error or a contrastive loss.

In some embodiments, the historical collection of the plurality of ECG signal portions may include a first ECG signal portion associated with a first time and a second ECG signal portion associated with a second time. Additionally or alternatively, heart monitoring device 202b and/or gateway device 229b may train the rhythm change classifier by generating, with the rhythm change classifier, a predicted time associated with the second ECG signal portion based on the a first ECG signal portion and the second ECG signal, determining at least one error value based on the predicted time and the second time, and updating the rhythm change classifier (e.g., updating the weights thereof and/or the like) based on the error value(s) (e.g., using back propagation and/or the like). In some embodiments, the error value(s) may include one of a prediction error or a contrastive loss.

In some embodiments, there may be an insufficient number of ECG signal portions in the historical collection of the plurality of ECG signal portions with known rhythm change information to train the rhythm change classifier to perform the desired task (e.g., detect and/or identify at least one predetermined rhythm changes). Additionally or alternatively, there may be sufficient data (e.g., historical ECG signal portions and/or the like) to train the rhythm change classifier to perform a separate task (e.g., which may be related in some way to the target task). In some embodiments, the rhythm change classifier may be trained to perform the separate task (e.g., counting R-peaks, determining heart rate, and/or the like based on the ECG signal(s)). Additionally or alternatively, the rhythm change classifier may then be adapted to perform the target task. For example, in some embodiments, the rhythm change classifier may be retrained using the limited amount of ECG signal portions in the historical collection of the plurality of ECG signal portions with known rhythm change information and/or the like. Additionally or alternatively, the rhythm change classifier may be used to perform the separate task (e.g., counting R-peaks, determining heart rate, and/or the like based on the ECG signal(s)), and the output thereof may be applied to the target task. For example, the processor (e.g., of heart monitoring device 202b and/or gateway device 229b) may detect, with the rhythm change classifier, at least one of a count of peaks or a heart rate based on the at least one ECG signal. Additionally or alternatively, the processor (e.g., of heart monitoring device 202b and/or gateway device 229b) may determine the detected at least one of the count of peaks or the heart rate is above a first threshold (e.g., tachycardia onset threshold) for the patient or below a second threshold (e.g., bradycardia onset threshold) for the patient (e.g., wherein the second threshold for the patient may be less than the first threshold for the patient). Additionally or alternatively, the processor (e.g., of heart monitoring device 202b and/or gateway device 229b) may detect the predetermined rhythm change based on the at least one of the count of peaks or the heart rate being above the first threshold (e.g., tachycardia onset threshold) for the patient or below the second threshold (e.g., bradycardia onset threshold) for the patient.

In some embodiments, there may be an insufficient number of ECG signal portions associated with (e.g., sensed from and/or the like) the plurality of ECG electrodes of the heart monitoring device 202b in the historical collection of the plurality of ECG signal portions with known rhythm change information to train the rhythm change classifier for the ECG signal(s) received form the plurality of ECG electrodes of the heart monitoring device 202a. Additionally or alternatively, there may be sufficient data (e.g., historical ECG signal portions and/or the like) associated with (e.g., sensed from and/or the like) a second plurality of ECG electrodes (e.g., electrodes from an ECG device separate from the heart monitoring device 202b, such as a 12-lead ECG sensor, a separate external and/or wearable heart monitoring device, and/or the like) independent of the plurality of ECG electrodes of the heart monitoring device 202a to train the rhythm change classifier based on the second plurality of ECG electrodes. In some embodiments, the rhythm change classifier may be trained based on the ECG signal portion(s) associated with (e.g., sensed from and/or the like) the second plurality of ECG electrodes. Additionally or alternatively, the rhythm change classifier may then be adapted to detect the predetermined rhythm change(s) based on the plurality of ECG electrodes of heart monitoring device 202b. In some embodiments, heart monitoring device 202b and/or gateway device 229b may determine (e.g., calculate and/or the like) a transform (e.g., vector projection and/or the like) of the ECG signal portion(s) associated with the second plurality of ECG electrodes to the plurality of ECG electrodes of heart monitoring device 202b, and the transform of the ECG signal portion(s) may be used to train the rhythm change classifier as if the ECG signal portions were associated with (e.g., sensed from and/or the like) the plurality of ECG electrodes of the heart monitoring device 202b.

In some embodiments, heart monitoring device 202b (e.g., the processor(s) thereof) may be configured to receive the ECG signal(s) via the ECG channel(s), as described herein. Additionally or alternatively, heart monitoring device 202b (e.g., the processor(s) thereof) may be configured to detect with the rhythm change classifier time data corresponding to a predetermined rhythm change in ECG signal(s), as described herein. In some embodiments, heart monitoring device 202a (e.g., the processor(s) thereof) may be configured to determine based on the detected time data at least one ECG signal portion associated with the detected time data corresponding to the predetermined rhythm change in the ECG signal(s), as described herein.

In some embodiments, heart monitoring device 202b (e.g., the processor(s) thereof) may be configured to receive the ECG signal(s) via the ECG channel(s), as described herein. Additionally or alternatively, heart monitoring device 202b (e.g., the processor(s) thereof) may be configured to transmit the ECG signal(s) to gateway device 229b. In some embodiments, gateway device 229b may be configured to detect with the rhythm change classifier time data corresponding to a predetermined rhythm change in ECG signal(s), as described herein. In some embodiments, gateway device 229b (e.g., the processor(s) thereof) may be configured to determine based on the detected time data at least one ECG signal portion associated with the detected time data corresponding to the predetermined rhythm change in the ECG signal(s), as described herein.

In some embodiments, the neural network(s) of the rhythm change classifier (e.g., of heart monitoring device 202b and/or gateway device 229b) may include a plurality of Siamese branches, as described herein.

In some embodiments, heart monitoring device 202b and/or gateway device 229b (e.g., processor(s) thereof) may be further configured to detect (e.g., with the trained rhythm change classifier) the predetermined rhythm change based on the at least one ECG signal, as described herein. In some embodiments, heart monitoring device 202b may further include at least one sensor and associated sensor circuitry configured to sense non-ECG biometric data of the patient (which, in some embodiments, may be communicated to gateway device 229b), as described herein. Additionally or alternatively, detecting the predetermined rhythm change may be further based on the non-ECG biometric data of the patient (e.g., non-ECG biometric data of the patient may be input into the neural network(s) of the rhythm change classifier, may be combined with the output of the rhythm change classifier, and/or the like), as described herein.

In some embodiments, detecting the predetermined rhythm change may be further based on at least one baseline ECG signal portion of the patient, as described herein.

In some embodiments, detecting the predetermined rhythm change may be further based on at least one calibration measurement of the patient, as described herein.

In some embodiments, detecting the predetermined rhythm change may be further based on at least one reference vector of the patient, as described herein.

In some embodiments, detecting the predetermined rhythm change may be further based on at least one previous ECG signal portion, as described herein.

In some embodiments, gateway device 229b may enable communication between heart monitoring device 202b and remote computer system 204b, as described herein.

In some embodiments, the processor (e.g., of heart monitoring device 202b and/or gateway device 229b) may further determine (e.g., with the rhythm change classifier) a confidence score associated with the predetermined rhythm change based on the at least one ECG signal, as described herein.

As shown in FIG. 2B, at 234b, heart monitoring device 202b and/or gateway device 229b (e.g., the processor(s) thereof) may communicate (e.g., transmit and/or the like) the determined ECG signal portion(s) to remote computer system 204b, as described herein. Additionally or alternatively, heart monitoring device 202b and/or gateway device 229b (e.g., the processor(s) thereof) may be configured to communicate an indication (e.g., a flag, an indicator, a confidence score, a mark, metadata, the time data, and/or the like) associated with the predetermined rhythm change detected (e.g., identified and/or the like) in the ECG signal portion(s), as described herein.

In some embodiments, the processor (e.g., of heart monitoring device 202b and/or gateway device 229b) may further communicate (e.g., transmit and/or the like) at least one second ECG signal portion of the ECG signal(s) to remote computer system 204b, as described herein. Additionally or alternatively, the second ECG signal portion(s) may be independent of the detected time data corresponding to the predetermined rhythm change in the ECG signal(s), as described herein.

In some embodiments, gateway device 229b may enable communication between heart monitoring device 202b and remote computer system 204b, as described herein.

In some embodiments, remote computing system 204b may receive the determined ECG signal portion(s) (e.g., from heart monitoring device 202b and/or gateway device 229b), as described herein. Additionally or alternatively, remote computing system 204b may analyze the determined ECG signal portion(s) to classify a type of arrhythmia for the rhythm change(s) in the ECG signal(s), as described herein. For example, remote computer system 204b may include an arrhythmia type classifier (e.g., including at least one (second) neural network trained based on a (second) historical collection of a (second) plurality of ECG signal portions with known arrhythmia type information), as described herein.

In some embodiments, remote computer system 204b may analyze the determined ECG signal portion(s) to identify at least one arrhythmia associated with the rhythm change in the at least one ECG signal, as described herein. In some embodiments, the arrhythmia may be one or more rare arrhythmias on which the remote computer system 204a may have previously been trained. Additionally or alternatively, remote computer system 204a may use any suitable signal processing technique (e.g., separate from or including the arrhythmia type classifier as described herein) to identify the rare arrhythmia(s), as described herein.

In some embodiments, the determined ECG signal portion(s) may include a plurality of determined ECG signal portions, as described herein. Additionally or alternatively, remote computer system 204b may receive the plurality of determined ECG signal portions from heart monitoring device 202b and/or gateway device 229b, as described herein. In some embodiments, remote computer system 204b may analyze each respective determined ECG signal portion to classify a respective class for each respective determined ECG signal portion, as described herein.

As shown in FIG. 2b, at 236b, remote computer system 204b may communicate (e.g., transmit and/or the like) at least one message associated with the determined ECG signal portion(s) and/or the type of arrhythmia associated with the rhythm change, as described herein. For example, the message(s) may be communicated from remote computer system 204b to technician device 208b, as described herein.

In some embodiments, remote computer system 204b may transmit at least one message associated with the second ECG signal portion(s) (e.g., randomly determined second ECG signal portion(s), second ECG signal portion(s) determined to have a confidence score below a first threshold and above a second threshold, and/or the like, as described herein) to technician device 208b, as described herein.

In some embodiments, remote computer system 204b may transmit at least one message associated with the at least two respective determined ECG signal portions and the first class to technician device 208b, as described herein.

As shown in FIG. 2B, at 238b, remote computer system 204b may receive annotation data associated with at least one annotation from technician device 208a, as described herein. For example, the annotation data may be communicated from technician device 208b to remote computer system 204b, as described herein. Additionally or alternatively, the ECG signal portion(s) associated with such annotation(s) may be communicated with the annotation data, as described herein.

In some embodiments, remote computer system 204b may receive (e.g., from technician device 208b) annotation data associated with at least one annotation for the second ECG signal portion(s) (e.g., randomly determined second ECG signal portion(s), second ECG signal portion(s) determined to have a confidence score below a first threshold and above a second threshold, and/or the like, as described herein).

In some embodiments, remote computer system 204a may retrain the arrhythmia type classifier based on the historical collection of the plurality of ECG signal portions with the known rhythm change information, the second ECG signal portion(s), and the annotation data associated therewith, as described herein.

As shown in FIG. 2B, at 240b, remote computer system 204b may communicate (e.g., transmit, write, and/or the like) the annotation data to data repository 206b, as described herein. Additionally or alternatively, the ECG signal portion(s) associated with such annotation(s) may be communicated with the annotation data, as described herein.

In some embodiments, annotation data and the ECG signal portion(s) associated with such annotation(s) may be added to the historical collection of the plurality of ECG signal portions, as described herein. In some embodiments, remote computer system 204b may retrain the arrhythmia type classifier based on the historical collection of the plurality of ECG signal portions with the known arrhythmia type information (which may now include the ECG signal portion(s) and/or the annotation data associated therewith).

In some embodiments, remote computer system 204b may add annotation data associated with at least one annotation for the second ECG signal portion(s) (e.g., randomly determined second ECG signal portion(s), second ECG signal portion(s) determined to have a confidence score below a first threshold and above a second threshold, and/or the like, as described herein) to the historical collection of the plurality of ECG signal portions in data repository 206b, as described herein. In some embodiments, remote computer system 204b may retrain the arrhythmia type classifier based on the historical collection of the plurality of ECG signal portions with the known arrhythmia type information (which may now include the second ECG signal portion(s) and/or the annotation data associated therewith), as described herein.

As shown in FIG. 2B, at 242b, remote computer system 204b may communicate (e.g., transmit and/or the like) the annotation data associated with at least one annotation for the second ECG signal portion(s) to heart monitoring device 202b and/or gateway device 229b, as described herein. Additionally or alternatively, heart monitoring device 202b and/or gateway device 229b (e.g., processor(s) thereof) may retrain the rhythm change classifier (and/or train an updated rhythm change classifier) based on the historical collection of the plurality of ECG signal portions with the known rhythm change information, the second ECG signal portion(s), and the annotation data associated therewith, as described herein.

Figure 2C:
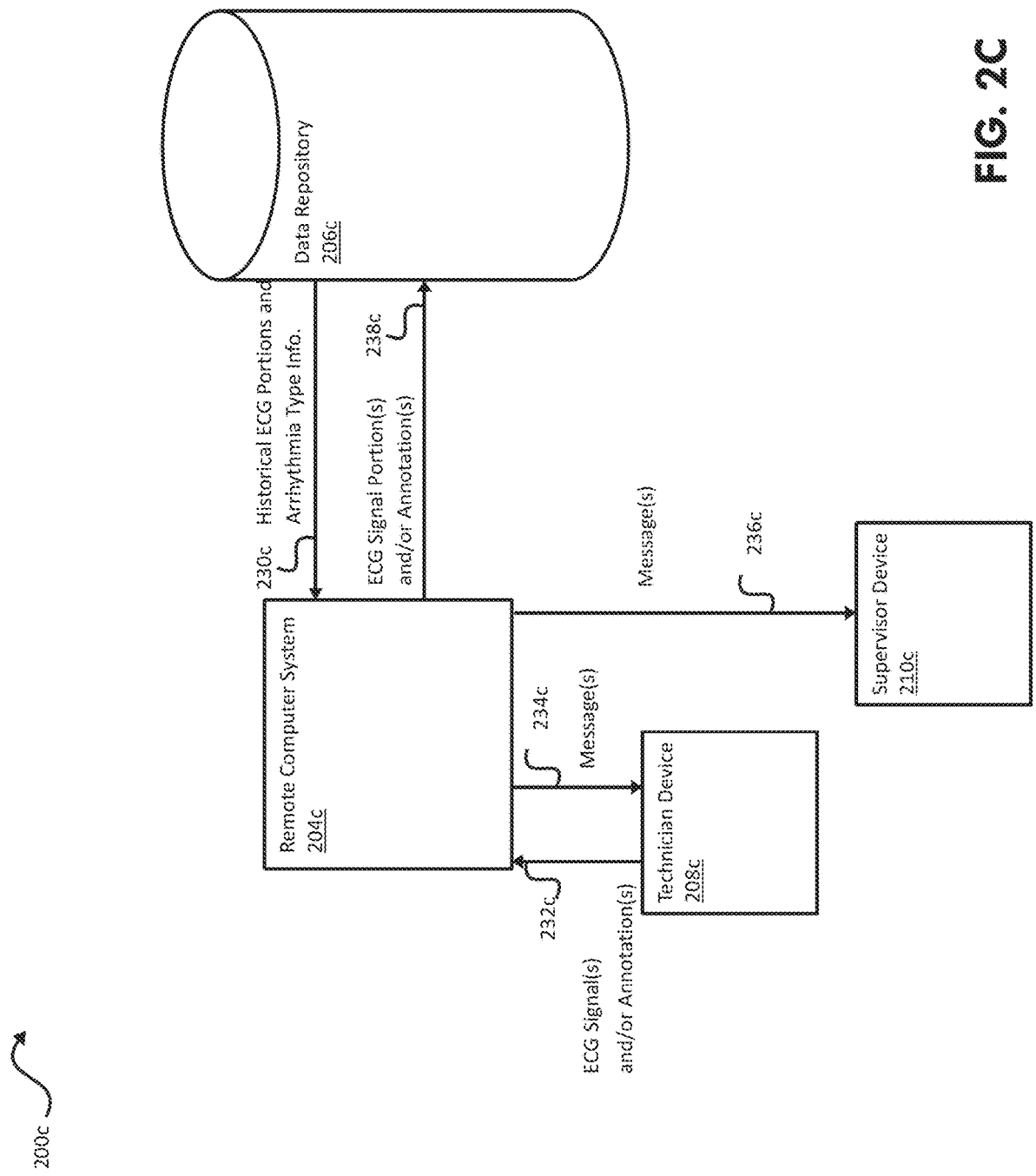

Referring now to FIG. 2C, FIG. 2C shows an example block diagram of a system architecture 200c for arrhythmia monitoring, according to some embodiments. In addition to system components, the system architecture 200c also shows data flows between the system components. As shown in FIG. 2C, system architecture 200c may include remote computer system 204c, data repository 206c, technician device 208c, and/or supervisor device 210c. In some embodiments, remote computer system 204c may be the same as or similar to remote computer system 104 (e.g., one or more devices of remote computer system 104), remote computer system 204a (e.g., one or more devices of remote computer system 204a), remote computer system 204b (e.g., one or more devices of remote computer system 204b), and/or the like. In some embodiments, data repository 206c may be the same as or similar to data repository 106 (e.g., one or more devices of data repository 106), data repository 206a (e.g., one or more devices of data repository 206a), data repository 206b (e.g., one or more devices of data repository 206b), and/or the like. In some embodiments, technician device 208c may be the same as or similar to technician device 108, technician device 208a, technician device 208b, and/or the like. In some embodiments, supervisor device 210c may be the same as or similar to supervisor device 210c and/or the like.

As shown in FIG. 2C, at 230c, remote computer system 204c may receive (e.g., retrieve, search for, send a request and/or query to cause data repository 206c to communicate, and/or the like) a historical collection of a plurality of ECG signal portions and information related thereto (e.g., known arrhythmia type information and/or the like), e.g., from data repository 206c, as described herein. In some embodiments, remote computer system 204c may train at least one neural network of at least one classifier (e.g., an arrhythmia type classifier and/or the like) based on the historical collection of a plurality of ECG signal portions and information related thereto (e.g., known arrhythmia type information and/or the like), as described herein.

In some embodiments, an arrhythmia type classifier may include at least one neural network (e.g., at least one second neural network), as described herein. Additionally or alternatively, the at least one (second) neural network may include at least one of a deep neural network, a convolutional neural network, a recurrent neural network, an attention network, a fully connected neural network, any combination thereof, and/or the like. For example, the neural network(s) may include at least one convolutional neural network having a plurality of convolutional layers. In some embodiments, the convolutional neural network(s) may include between five and 40 convolutional layers (e.g., at least five convolutional layers and up to 40 convolutional layers). For example, the convolutional neural network(s) may include between seven and ten convolutional layers (e.g., at least seven convolutional layers and no more than ten convolutional layers). In some embodiments, each convolutional layer may include at least one convolutional nodes (e.g., a plurality of convolutional nodes). In some embodiments, the convolutional neural network(s) may further include an input layer and an output layer. For example, the ECG signal(s) may include a plurality of ECG signal samples. Additionally or alternatively, the input layer may include at least one node for each ECG signal sample of the plurality of ECG signal samples (or a subset thereof, e.g., associated with a predetermined time period, a buffer size of a buffer for ECG signal samples, and/or the like). Additionally or alternatively, the input layer may further include at least one input for non-ECG biometric data associated with sensors (e.g., of heart monitoring device 102 and/or the like), as described herein. In some embodiments, an output of the output layer may include an indication of the time data corresponding to the arrhythmia type. Additionally or alternatively, an output of the output layer may include a confidence score, a plausibility score, and/or the lie, as described herein. In some embodiments, the neural network(s) may include a plurality of Siamese branches (e.g., each respective Siamese branch associated with a respective ECG channel), as described herein.

In some embodiments, remote computer system 204c may train an arrhythmia type classifier by predicting, with the arrhythmia type classifier, a predicted type of arrhythmia in each respective ECG signal portion of the historical collection of the plurality of ECG signal portions (or a second plurality thereof), determining at least one error value based on the predicted type of arrhythmia and the known arrhythmia type information (e.g., a respective annotations associated with a known type of arrhythmia for each respective ECG signal portion), and training the arrhythmia type classifier (e.g., updating the weights thereof and/or the like) based on the error value(s) (e.g., using back propagation and/or the like). In some embodiments, the error value(s) may include one of a prediction error or a contrastive loss.

In some embodiments, the known arrhythmia type information may include a plurality of annotations. For example, each annotation may be associated with a respective ECG signal portion of the plurality of ECG signal portions. In some embodiments, remote computer system 204c may train the arrhythmia type classifier based on the plurality of ECG signals and the plurality of annotations, as described herein.

In some embodiments, the plurality of annotations may be from a plurality of technicians (e.g., a plurality of technician devices 208c and/or the like). Additionally or alternatively, each annotation annotations may be associated with a respective technician of the plurality of technicians and/or a respective ECG signal portion of the plurality of ECG signal portions. In some embodiments, the arrhythmia type classifier may be trained separately for each technician. For example, for a first technician of the plurality of technicians, the arrhythmia type classifier may be trained (e.g., by remote computer system 204c) based on a subset of the plurality of ECG signals and the plurality of annotations associated with at least one other technician of the plurality of technicians different than the first technician (e.g., for the first technician, only train the arrhythmia type classifier based on annotations from other technicians).

In some embodiments, each annotation may be associated with one possible type of arrhythmia (e.g., a label associated with a possible type of arrhythmia, a text string identifying at least one possible type arrhythmia, and/or the like) of the respective ECG signal(s) and/or portion(s) thereof.

In some embodiments, there may be an insufficient number of ECG signal portions associated with (e.g., sensed from and/or the like) at least one second ECG electrode in the historical collection of the plurality of ECG signal portions with known arrhythmia type information (e.g., annotations, labels, and/or the like) to train the arrhythmia type classifier for the ECG signal(s) received from the second ECG electrode(s). Additionally or alternatively, there may be sufficient data (e.g., historical ECG signal portions and/or the like) associated with (e.g., sensed from and/or the like) at least one first ECG electrode (e.g., electrodes from an ECG device separate from the second ECG electrode(s), such as a 12-lead ECG sensor, a separate external and/or wearable heart monitoring device, and/or the like) independent of the second ECG electrode(s) to train the rhythm change classifier based on the second ECG electrode(s). In some embodiments, the known arrhythmia type information may include a plurality of annotations, each of which may be associated with a respective ECG signal portion of a first plurality of ECG signal portions associated with the first ECG electrode(s). In some embodiments, each respective ECG signal portion of a second plurality of ECG signal portions associated with the second ECG electrode(s) may correspond to a respective ECG signal portion of the first plurality of ECG signal portions. In some embodiments, remote computer system 204c may train the arrhythmia type classifier by predicting, with the arrhythmia type classifier, a predicted type of arrhythmia in each respective ECG signal portion of the second plurality of ECG signal portions, determining at least one error value based on the predicted type of arrhythmia and the respective annotation of the plurality of annotations associated with a respective ECG signal portion of the first plurality of ECG signal portions corresponding to the respective ECG signal portion of the second plurality of ECG signal portions, and training (e.g., updating the weights of and/or the like) the arrhythmia type classifier based on the at least one error value (e.g., based on back propagation and/or the like).

In some embodiments, ECG signal portions associated with multiple electrodes may be combined (e.g., by vector addition, vector projection, a transform, and/or the like) to form extrapolated ECG signal portions that may be more familiar and/or suitable for review by a human user (e.g., technician and/or the like). For example, the historical collection of the plurality of ECG signal portions may include a first plurality of ECG signal portions of at least one first ECG signal based on first surface ECG activity sensed by at least one first ECG electrode and a second plurality of ECG signal portions of at least one second ECG signal based on second surface ECG activity sensed by at least one second ECG electrode. Additionally or alternatively, the at least one second ECG electrode may be independent of the at least one first ECG electrode. In some embodiments, each ECG signal portion of the first plurality of ECG signal portions may be combined (e.g., by vector addition, vector projection, a transform, and/or the like) with a respective ECG signal portion of the second plurality of ECG signal portions to form a plurality of extrapolated ECG signal portions (e.g., by remote computer system 204c). In some embodiments, the known arrhythmia type information may include a plurality of annotations. Additionally or alternatively, each respective annotation may be associated with a respective extrapolated ECG signal portion of the plurality of extrapolated ECG signal portions.

In some embodiments, at least some of the plurality of ECG signal portions of the historical collection may be time warped (e.g., time dilated and/or the like) to form a plurality of warped ECG signal portions (e.g., by remote computer system 204c using any suitable signal processing technique for time warping, time dilation, and/or the like).

In some embodiments, at least some of the plurality of ECG signal portions of the historical collection may be at least one of filtered, inverted, any combination thereof, and/or the like (e.g., by remote computer system 204c).

In some embodiments, at least one noise signal portion may be combined with at least some of the plurality of ECG signal portions of the historical collection (e.g., by remote computer system 204c).

In some embodiments, at least some of the plurality of ECG signal portions of the historical collection may be style transferred (e.g., by remote computer system 204c). For example, remote computer system 204c may search for ECG signals that share low level features with one reference signal and high-level features with a second reference signal (e.g., the second reference signal may be associated with a rare type/class of arrhythmia and/or the like). Additionally or alternatively, the low and/or high level features may be the output of a pre-trained classification network with respective low and/or high layers.

As shown in FIG. 2C, at 232c, remote computer system 204c may receive at least one ECG signal and annotation data associated with at least one annotation for each ECG signal, as described herein.

In some embodiments, remote computer system 204c may detect, with the arrhythmia type classifier, a type of arrhythmia in the ECG signal(s) and time data associated with the detected type of arrhythmia, as described herein. For example, the time data may include at least one of a start time, a time interval, any combination thereof, and/or the like, as described herein. In some embodiments, remote computer system 204c may determine, based on the time data, at least one ECG signal portion associated with the detected type of arrhythmia in the ECG signal(s), as described herein.

In some embodiments, remote computer system 204c may determine a plausibility score for the annotation(s) based on the detected type of arrhythmia. For example, an output of at least one neural network of the arrhythmia type classifier may include a confidence score (e.g., a probability and/or the like) associated with each possible type of arrhythmia, as described herein. For example, the type of arrhythmia determined by the arrhythmia type classifier may be the type of arrhythmia with a highest confidence score (e.g., probability and/or the like). Additionally or alternatively, each annotation may be associated with one possible type of arrhythmia (e.g., a label associated with a possible type of arrhythmia, a text string identifying at least one possible type arrhythmia, and/or the like). In some embodiments, plausibility score of each annotation may be the confidence score (e.g., determined by the arrhythmia type classifier) of the possible type of arrhythmia associated with such annotation. In some embodiments, the arrhythmia type classifier may include a plurality of neural networks, and each such neural network may output a confidence score associated with at least one possible type of arrhythmia.

In some embodiments, remote computer system 204c may generate at least one message based on the at least one determined ECG signal portion and the plausibility score for the at least one annotation, as described herein. For example, the message(s) may indicate at least one of a recommendation to annotate the at least one determined ECG signal portion based on the detected type of arrhythmia, a recommendation to reevaluate the annotation data associated with the at least one determined ECG signal portion based on the plausibility score, and/or the like.

In some embodiments, remote computer system 204c may to determine the plausibility score is below a threshold. Additionally or alternatively, generating the message(s) may include remote computer system 204c generating, based on the determination that the plausibility score is below the threshold, the at least one message indicating the recommendation to reevaluate the annotation data associated with the at least one determined ECG signal portion, as described herein.

As shown in FIG. 2C, at 234c, remote computer system 204c may transmit the at least some of the message(s) associated with the at least one determined ECG signal portion to technician device 208c, as described herein.

As shown in FIG. 2C, at 236c, remote computer system 204c may transmit the at least some of the message(s) associated with the at least one determined ECG signal portion to supervisor device 210c, as described herein.

Figure 3A:
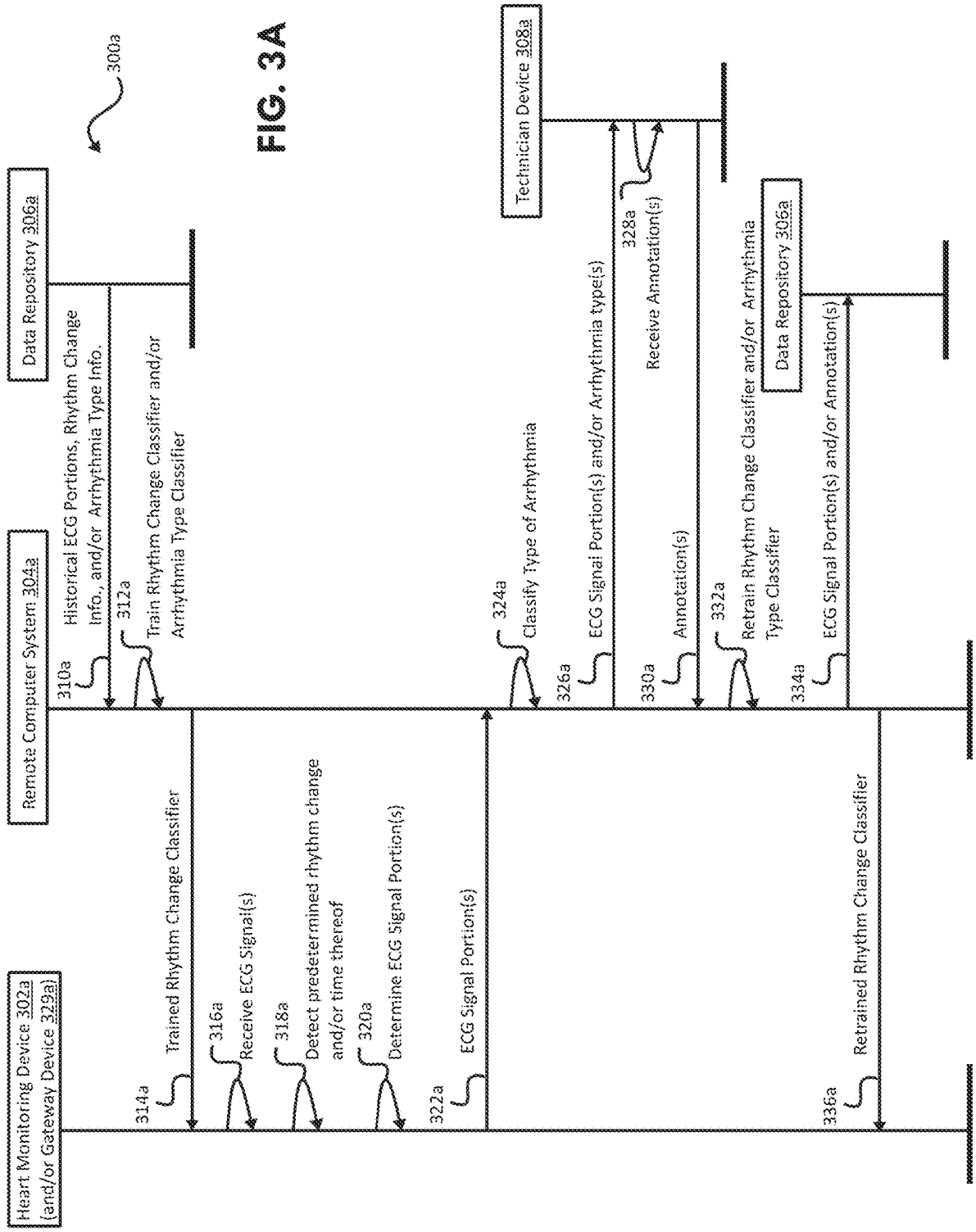

Referring now to FIG. 3A, FIG. 3A shows an example swim lane diagram of a process 300a for arrhythmia monitoring, according to some embodiments. In addition to system components, the process 300a also shows communication flows between the system components. As shown in FIG. 3A, in some embodiments, heart monitoring device 302a may be the same as or similar to heart monitoring device 102, heart monitoring devices 202a and/or 202b, and/or the like. In some embodiments, remote computer system 304a may be the same as or similar to remote computer system 104, remote computer systems 204a, 204b, and/or 204c, and/or the like. In some embodiments, data repository 306a may be the same as or similar to data repository 106, data repositories 206a, 206b, and/or 206c, and/or the like. In some embodiments, technician device 308a may be the same as or similar to technician device 108, technician devices 202a, 202b, and/or 202c, and/or the like. In some embodiments, gateway device 329a may be the same as or similar to gateway device 129, gateway devices 229a and/or 229b, and/or the like.

As shown in FIG. 3A, at 310a, remote computer system 304a may receive (e.g., retrieve, search for, send a request and/or query to cause data repository 206a to communicate, and/or the like) a historical collection of a plurality of ECG signal portions and information related thereto (e.g., known rhythm change information, known arrhythmia type information, and/or the like), e.g., from data repository 306a, as described herein.

As shown in FIG. 3A, at 310a, remote computer system 304a may train at least one neural network of at least one classifier (e.g., a rhythm change classifier, an arrhythmia type classifier, and/or the like) based on the historical collection of a plurality of ECG signal portions and information related thereto (e.g., known rhythm change information, known arrhythmia type information, and/or the like, respectively), as described herein.

In some embodiments, a rhythm change classifier may include at least one neural network, as described herein. For example, the at least one neural network may include at least one of a convolutional neural network, a recurrent neural network, an attention network, a fully connected neural network, any combination thereof, and/or the like, as described herein.

In some embodiments, remote computer system 304a may train the rhythm change classifier by predicting, with the rhythm change classifier, predicted rhythm change information (e.g., data (e.g., probability, confidence score, and/or the like) associated with a predicted rhythm change, data (e.g., probability, confidence score, and/or the like) associated with a lack of a predicted rhythm change, and/or the like) for each ECG signal portion of the historical collection of the plurality of ECG signal portions, determining at least one error value based on the predicted rhythm change information and the known rhythm change information, and training the rhythm change classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, the historical collection of the plurality of ECG signal portions may include a first ECG signal portion associated with a first time and a second ECG signal portion associated with a second time after the first time. Additionally or alternatively, remote computer system 304a may train the rhythm change classifier by predicting, with the rhythm change classifier, a predicted ECG signal portion associated with the second time based on the first ECG signal portion, determining at least one error value based on the predicted ECG signal portion and the second ECG signal portion, and training the rhythm change classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, the historical collection of the plurality of ECG signal portions may include a first ECG signal portion associated with a first time and a second ECG signal portion associated with a second time. Additionally or alternatively, remote computer system 304a may train the rhythm change classifier by predicting, with the rhythm change classifier, a predicted time associated with the second ECG signal portion based on the a first ECG signal portion and the second ECG signal, determining at least one error value based on the predicted time and the second time, and training the rhythm change classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, remote computer system 304a may train an arrhythmia type classifier by predicting, with the arrhythmia type classifier, a predicted type of arrhythmia in each respective ECG signal portion of the historical collection of the plurality of ECG signal portions (or a second plurality thereof), determining at least one error value based on the predicted type of arrhythmia and the known arrhythmia type information (e.g., a respective annotations associated with a known type of arrhythmia for each respective ECG signal portion), and training the arrhythmia type classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, there may be an insufficient number of ECG signal portions in the historical collection of the plurality of ECG signal portions with known rhythm change information to train the rhythm change classifier to perform the desired task (e.g., detect and/or identify at least one predetermined rhythm changes). Additionally or alternatively, there may be sufficient data (e.g., historical ECG signal portions and/or the like) to train the rhythm change classifier to perform a separate task (e.g., which may be related in some way to the target task). In some embodiments, the rhythm change classifier may be trained to perform the separate task (e.g., counting R-peaks, determining heart rate, and/or the like based on the ECG signal(s)). Additionally or alternatively, the rhythm change classifier may then be adapted to perform the target task, as described herein. For example, in some embodiments, the rhythm change classifier may be retrained using the limited amount of ECG signal portions in the historical collection of the plurality of ECG signal portions with known rhythm change information and/or the like, as described herein. Additionally or alternatively, the rhythm change classifier may be used to perform the separate task (e.g., counting R-peaks, determining heart rate, and/or the like based on the ECG signal(s)), and the output thereof may be applied to the target task, as described herein. For example, the processor (e.g., of heart monitoring device 302a and/or gateway device 329a) may detect, with the rhythm change classifier, at least one of a count of peaks or a heart rate based on the at least one ECG signal. Additionally or alternatively, the processor (e.g., of heart monitoring device 302a and/or gateway device 329a) may determine the detected at least one of the count of peaks or the heart rate is above a first threshold (e.g., tachycardia onset threshold) for the patient or below a second threshold (e.g., bradycardia onset threshold) for the patient (e.g., wherein the second threshold for the patient may be less than the first threshold for the patient). Additionally or alternatively, the processor (e.g., of heart monitoring device 302a and/or gateway device 329a) may detect the predetermined rhythm change based on the at least one of the count of peaks or the heart rate being above the first threshold (e.g., tachycardia onset threshold) for the patient or below the second threshold (e.g., bradycardia onset threshold) for the patient.

In some embodiments, there may be an insufficient number of ECG signal portions associated with (e.g., sensed from and/or the like) the plurality of ECG electrodes of the heart monitoring device 302a in the historical collection of the plurality of ECG signal portions with known rhythm change information to train the rhythm change classifier for the ECG signal(s) received form the plurality of ECG electrodes of the heart monitoring device 202a. Additionally or alternatively, there may be sufficient data (e.g., historical ECG signal portions and/or the like) associated with (e.g., sensed from and/or the like) a second plurality of ECG electrodes (e.g., electrodes from an ECG device separate from the heart monitoring device 302a, such as a 12-lead ECG sensor, a separate external and/or wearable heart monitoring device, and/or the like) independent of the plurality of ECG electrodes of the heart monitoring device 302a to train the rhythm change classifier based on the second plurality of ECG electrodes. In some embodiments, the rhythm change classifier may be trained based on the ECG signal portion(s) associated with (e.g., sensed from and/or the like) the second plurality of ECG electrodes, as described herein. Additionally or alternatively, the rhythm change classifier may then be adapted to detect the predetermined rhythm change(s) based on the plurality of ECG electrodes of the heart monitoring device 302a, as described herein. In some embodiments, remote computer system 204a may determine (e.g., calculate and/or the like) a transform (e.g., vector projection and/or the like) of the ECG signal portion(s) associated with the second plurality of ECG electrodes to the plurality of ECG electrodes of the heart monitoring device 302a, and the transform of the ECG signal portion(s) may be used to train the rhythm change classifier as if the ECG signal portions were associated with (e.g., sensed from and/or the like) the plurality of ECG electrodes of the heart monitoring device 302a.

In some embodiments, an arrhythmia type classifier may include at least one neural network (e.g., at least one second neural network), as described herein. Additionally or alternatively, the at least one (second) neural network may include at least one of a deep neural network, a convolutional neural network, a recurrent neural network, an attention network, a fully connected neural network, any combination thereof, and/or the like, as described herein.

As shown in FIG. 3A, at 314a, remote computer system 304a may communicate a trained rhythm change classifier (or a plurality of weights thereof) to heart monitoring device 302a and/or gateway device 329a, as described herein. In some embodiments, after training, a plurality of weights corresponding to the trained rhythm change classifier may be communicated to heart monitoring device 302a and/or gateway device 329a. Additionally or alternatively, a copy of the trained rhythm change classifier (or a plurality of weights thereof) may be downloaded from remote computer system 304a and/or installed on (e.g., uploaded to, written to, configured on, and/or the like) at least one non-transitory computer readable medium (e.g., e.g., a memory, a programmable circuit board, a field programmable gate array (FPGA), an integrated circuit, any combination thereof, and/or the like), which may be installed in and/or part of heart monitoring device 302a and/or gateway device 329a.

In some embodiments, heart monitoring device 302a may be an external heart monitoring device for a patient, as described herein. For example, (external) heart monitoring device 302a may include a plurality of ECG electrodes configured to sense surface ECG activity of the patient, as described herein. For example, (external) heart monitoring device 302a may include ECG processing circuitry configured to process the surface ECG activity of the patient to provide at least one ECG signal for the patient on at least one ECG channel.

In some embodiments, (external) heart monitoring device 302a may include a non-transitory computer-readable medium (e.g., a memory, a programmable circuit board, a field programmable gate array, an integrated circuit, any combination thereof, and/or the like) including (e.g., implementing, embodying, storing, and/or the like) the trained rhythm change classifier (which may include, e.g., at least one neural network trained based on the historical collection of a plurality of ECG signal portions with known rhythm change information), as described herein. Additionally or alternatively, (external) heart monitoring device 302a may include at least one processor operatively connected to the ECG channel(s) and the non-transitory computer-readable medium.

In some embodiments, gateway device 329a may include a non-transitory computer-readable medium (e.g., a memory, a programmable circuit board, a field programmable gate array, an integrated circuit, any combination thereof, and/or the like) including (e.g., implementing, embodying, storing, and/or the like) the trained rhythm change classifier (which may include, e.g., at least one neural network trained based on the historical collection of a plurality of ECG signal portions with known rhythm change information), as described herein. Additionally or alternatively, gateway device 329a may include at least one processor operatively connected to the non-transitory computer-readable medium.

In some embodiments, gateway device 329a may enable communication between heart monitoring device 202a and remote computer system 204a, as described herein.

As shown in FIG. 3A, at 316a, heart monitoring device 302a and/or gateway device 329a (e.g., the processor(s) thereof) may be configured to receive the ECG signal(s). In some embodiments, heart monitoring device 302a may be configured to receive the ECG signal(s) via the ECG channel(s), as described herein. Additionally or alternatively, heart monitoring device 302a may be configured to communicate (e.g., transmit) the ECG signal(s) to gateway device 329a, and/or gateway device 329a may receive the ECG signals from heart monitoring device 302a, as described herein.

As shown in FIG. 3A, at 318a, heart monitoring device 302a and/or gateway device 329a (e.g., the processor(s) thereof) may be configured to detect with the rhythm change classifier time data corresponding to a predetermined rhythm change in the at least one ECG signal, as described herein. For example, the predetermined rhythm change may be associated with an arrhythmia (e.g., a change in heart rate, atrial fibrillation, flutter, supraventricular tachycardia, ventricular tachycardia, pause, AV block, ventricular fibrillation, bigeminy, trigeminy, ventricular ectopic beats, bradycardia, tachycardia, a change in morphology of the at least one ECG signal, any combination thereof, and/or the like), as described herein. Additionally or alternatively, the time data may include at least one of a start time, a time interval, any combination thereof, and/or the like, as described herein.

As shown in FIG. 3A, at 320a, heart monitoring device 302a and/or gateway device 329a (e.g., the processor(s) thereof) may be configured to determine (e.g., based on the detected time data) at least one ECG signal portion associated with the detected time data corresponding to the predetermined rhythm change in the ECG signal(s), as described herein.

In some embodiments, the ECG channel(s) may include a plurality of ECG channels, as described herein. Additionally or alternatively, the ECG signal(s) may include at least one respective ECG signal associated with each respective ECG channel, as described herein. In some embodiments, the plurality of ECG channels may include a first ECG channel and a second ECG channel, as described herein. Additionally or alternatively, the ECG signal(s) may include a first respective ECG signal associated with the first ECG channel and a second respective ECG signal associated with the second ECG channel, as described herein. In some embodiments, the first respective ECG signal may be substantially orthogonal to the second respective ECG signal, as described herein.

In some embodiments, the neural network(s) of the rhythm change classifier (e.g., of heart monitoring device 302a and/or gateway device 329a) may include a plurality of Siamese branches, as described herein. Additionally or alternatively, each respective Siamese branch may be associated with a respective ECG channel (e.g., of the plurality of ECG channels), as described herein.

In some embodiments, heart monitoring device 302a and/or gateway device 329a (e.g., processor(s) thereof) may be further configured to detect (e.g., with the trained rhythm change classifier) the predetermined rhythm change based on the at least one ECG signal. In some embodiments, heart monitoring device 302a may further include at least one sensor and associated sensor circuitry configured to sense non-ECG biometric data of the patient (which, in some embodiments, may be communicated to gateway device 329a), as described herein. Additionally or alternatively, detecting the predetermined rhythm change may be further based on the non-ECG biometric data of the patient (e.g., non-ECG biometric data of the patient may be input into the neural network(s) of the rhythm change classifier, may be combined with the output of the rhythm change classifier, and/or the like), as described herein In some embodiments, detecting the predetermined rhythm change may be further based on at least one baseline ECG signal portion of the patient, as described herein.

In some embodiments, detecting the predetermined rhythm change may be further based on at least one calibration measurement of the patient, as described herein.

In some embodiments, detecting the predetermined rhythm change may be further based on at least one reference vector of the patient, as described herein.

In some embodiments, detecting the predetermined rhythm change may be further based on at least one previous ECG signal portion, as described herein.

In some embodiments, the processor (e.g., of heart monitoring device 302a and/or gateway device 329a) may further determine (e.g., with the rhythm change classifier) a confidence score associated with the predetermined rhythm change based on the at least one ECG signal, as described herein.

As shown in FIG. 3A, at 322a, heart monitoring device 302a and/or gateway device 329a (e.g., the processor(s) thereof) may communicate (e.g., transmit and/or the like) the determined ECG signal portion(s) to remote computer system 304a, as described herein. Additionally or alternatively, heart monitoring device 302a and/or gateway device 329a (e.g., the processor(s) thereof) may be configured to communicate an indication (e.g., a flag, an indicator, a confidence score, a mark, metadata, the time data, and/or the like) associated with the predetermined rhythm change detected (e.g., identified and/or the like) in the ECG signal portion(s).

In some embodiments, the processor (e.g., of heart monitoring device 202a and/or gateway device 329a) may further communicate (e.g., transmit and/or the like) at least one second ECG signal portion of the ECG signal(s) to remote computer system 304a, as described herein. Additionally or alternatively, the second ECG signal portion(s) may be independent of the detected time data corresponding to the predetermined rhythm change in the ECG signal(s), as described herein.

In some embodiments, gateway device 329a may enable communication between heart monitoring device 302a and remote computer system 304a, as described herein. For example, transmitting the determined ECG signal portion(s) to remote computer system 204a may include heart monitoring device 202a communicating (e.g., transmitting and/or the like) the determined ECG signal portion(s) to gateway device 329a, as described herein.

In some embodiments, remote computing system 304a may receive the determined ECG signal portion(s) (e.g., from heart monitoring device 302a and/or gateway device 329a).

As shown in FIG. 3A, at 324a, remote computing system 304a may analyze the determined ECG signal portion(s) to classify a type of arrhythmia for the rhythm change(s) in the ECG signal(s), as described herein. In some embodiments, the type of arrhythmia may include at least one of a change in heart rate, atrial fibrillation, flutter, supraventricular tachycardia, ventricular tachycardia, pause, AV block, ventricular fibrillation, bigeminy, trigeminy, ventricular ectopic beats, bradycardia, tachycardia, a change in morphology of the at least one ECG signal, any combination thereof, and/or the like, as described herein.

In some embodiments, remote computer system 304a may include an arrhythmia type classifier (e.g., including at least one (second) neural network trained based on a (second) historical collection of a (second) plurality of ECG signal portions with known arrhythmia type information), as described herein. Additionally or alternatively, analyzing the at least one determined ECG signal portion may include remote computer system 304a detecting with the arrhythmia type classifier the type of arrhythmia associated with the rhythm change based on the determined ECG signal portion(s), as described herein.

In some embodiments, remote computer system 304a may analyze the determined ECG signal portion(s) to identify at least one arrhythmia associated with the rhythm change in the at least one ECG signal, as described herein. In some embodiments, the arrhythmia may be one or more rare arrhythmias on which the remote computer system 304a may have previously been trained. Additionally or alternatively, remote computer system 304a may use any suitable signal processing technique (e.g., separate from or including the arrhythmia type classifier as described herein) to identify the rare arrhythmia(s), as described herein.

In some embodiments, the determined ECG signal portion(s) may include a plurality of determined ECG signal portions. Additionally or alternatively, remote computer system 304a may receive the plurality of determined ECG signal portions from heart monitoring device 302a and/or gateway device 329a, as described herein. In some embodiments, remote computer system 304a may analyze each respective determined ECG signal portion to classify a respective class for each respective determined ECG signal portion, as described herein. Additionally or alternatively, the class for at least two respective determined ECG signal portions may include a first class (e.g., at least two ECG signal portions may belong to the same class/grouping), as described herein.

As shown in FIG. 3A, at 326a, remote computer system 304a may communicate (e.g., transmit and/or the like) at least one message associated with the determined ECG signal portion(s) and/or the type of arrhythmia associated with the rhythm change, as described herein. For example, the message(s) may be communicated from remote computer system 304a to technician device 308a, as described herein.

In some embodiments, remote computer system 304a may transmit at least one message associated with the second ECG signal portion(s) (e.g., randomly determined second ECG signal portion(s), second ECG signal portion(s) determined to have a confidence score below a first threshold and above a second threshold, and/or the like, as described herein) to technician device 308a, as described herein.

In some embodiments, remote computer system 304a may transmit at least one message associated with the at least two respective determined ECG signal portions and the first class to technician device 308a, as described herein.

As shown in FIG. 3A, at 328a, technician device 308b may receive at least one annotation associated with the ECG signal portion(s), e.g., via input from a user (e.g., a technician and/or the like).

As shown in FIG. 3A, at 330a, remote computer system 304a may receive annotation data associated with the annotation(s) from technician device 308a, as described herein. For example, the annotation data may be communicated from technician device 308a to remote computer system 304a, as described herein. Additionally or alternatively, the ECG signal portion(s) associated with such annotation(s) may be communicated with the annotation data, as described herein.

In some embodiments, remote computer system 304*a* may receive (e.g., from technician device 308*a*) annotation data associated with annotation(s) for the second ECG signal portion(s) (e.g., randomly determined second ECG signal portion(s), second ECG signal portion(s) determined to have a confidence score below a first threshold and above a second threshold, and/or the like, as described herein), as described herein.

As shown in FIG. 3A, at 332*a*, remote computer system 304*a* may retrain the rhythm change classifier (and/or train an updated rhythm change classifier) based on the historical collection of the plurality of ECG signal portions with the known rhythm change information, the second ECG signal portion(s), and the annotation data associated therewith, as described herein. In some embodiments, remote computer system 304*a* may retrain the arrhythmia type classifier based on the historical collection of the plurality of ECG signal portions with the known rhythm change information, the second ECG signal portion(s), and the annotation data associated therewith.

As shown in FIG. 3A, at 334*a*, remote computer system 304*a* may communicate (e.g., transmit, write, and/or the like) the annotation data to data repository 306*a*, as described herein. Additionally or alternatively, the ECG signal portion(s) associated with such annotation(s) may be communicated with the annotation data, as described herein.

In some embodiments, annotation data and the ECG signal portion(s) associated with such annotation(s) may be added to the historical collection of the plurality of ECG signal portions. For example, the annotation data may be stored as the known rhythm change information and/or the known arrhythmia type information for the ECG signal portion(s) associated with such annotation(s). In some embodiments, remote computer system 304*a* may retrain the rhythm change classifier (and/or train an updated rhythm change classifier) based on the historical collection of the plurality of ECG signal portions with the known rhythm change information (which may now include the ECG signal portion(s) and/or the annotation data associated therewith). In some embodiments, remote computer system 304*a* may retrain the arrhythmia type classifier based on the historical collection of the plurality of ECG signal portions with the known arrhythmia type information (which may now include the ECG signal portion(s) and/or the annotation data associated therewith).

In some embodiments, remote computer system 304*a* may add annotation data associated with at least one annotation for the second ECG signal portion(s) (e.g., randomly determined second ECG signal portion(s), second ECG signal portion(s) determined to have a confidence score below a first threshold and above a second threshold, and/or the like, as described herein) to the historical collection of the plurality of ECG signal portions in data repository 306*a*. In some embodiments, remote computer system 304*a* may retrain the rhythm change classifier (and/or train an updated rhythm change classifier) based on the historical collection of the plurality of ECG signal portions with the known rhythm change information (which may now include the second ECG signal portion(s) and/or the annotation data associated therewith). In some embodiments, remote computer system 304*a* may retrain the arrhythmia type classifier based on the historical collection of the plurality of ECG signal portions with the known arrhythmia type information (which may now include the second ECG signal portion(s) and/or the annotation data associated therewith).

As shown in FIG. 3A, at 336*a*, remote computer system 304*a* may communicate the retrained rhythm change classifier (and/or trained updated rhythm change classifier) and/or weights thereof to heart monitoring device 302*a* and/or gateway device 329*a*, as described herein. Additionally or alternatively, a copy of the retrained rhythm change classifier (and/or trained updated rhythm change classifier) and/or weights thereof may be downloaded from remote computer system 304*a* and/or installed on (e.g., uploaded to, written to, configured on, and/or the like) at least one non-transitory computer readable medium (e.g., e.g., memory, programmable circuit board, FPGA, integrated circuit, any combination thereof, and/or the like), which may be installed in and/or part of heart monitoring device 302*a* and/or gateway device 329*a*.

Referring now to FIG. 3B, FIG. 3B shows an example swim lane diagram of a process 300*b* for arrhythmia monitoring, according to some embodiments. In addition to system components, the process 300*b* also shows communication flows between the system components. As shown in FIG. 3B, in some embodiments, heart monitoring device 302*b* may be the same as or similar to heart monitoring device 102, heart monitoring devices 202*a* and/or 202*b*, heart monitoring device 302*a*, and/or the like. In some embodiments, remote computer system 304*b* may be the same as or similar to remote computer system 104, remote computer systems 204*a*, 204*b*, and/or 204*c*, remote computer system 304*a*, and/or the like. In some embodiments, data repository 306*b* may be the same as or similar to data repository 106, data repositories 206*a*, 206*b*, and/or 206*c*, data repository 306*a*, and/or the like. In some embodiments, technician device 308*b* may be the same as or similar to technician device 108, technician devices 208*a*, 208*b*, and/or 208*c*, technician device 308*a*, and/or the like. In some embodiments, gateway device 329*b* may be the same as or similar to gateway device 129, gateway devices 229*a* and/or 229*b*, gateway device 329*a*, and/or the like.

As shown in FIG. 3B, at 310*b*, remote computer system 304*b* may receive (e.g., retrieve, search for, send a request and/or query to cause data repository 206*b* to communicate, and/or the like) a historical collection of a plurality of ECG signal portions and information related thereto (e.g., known rhythm change information, known arrhythmia type information, and/or the like), e.g., from data repository 306*b*, as described herein.

As shown in FIG. 3B, at 312*b*, remote computer system 304*b* may train at least one neural network of at least one classifier (e.g., an arrhythmia type classifier and/or the like) based on the historical collection of a plurality of ECG signal portions and information related thereto (e.g., known arrhythmia type information and/or the like), as described herein.

In some embodiments, an arrhythmia type classifier may include at least one neural network (e.g., at least one second neural network), as described herein. Additionally or alternatively, the at least one (second) neural network may include at least one of a deep neural network, a convolutional neural network, a recurrent neural network, an attention network, a fully connected neural network, any combination thereof, and/or the like, as described herein. In some embodiments, the neural network(s) may include a plurality of Siamese branches (e.g., each respective Siamese branch associated with a respective ECG channel), as described herein.

In some embodiments, remote computer system 304*b* may train an arrhythmia type classifier by predicting, with the arrhythmia type classifier, a predicted type of arrhythmia in each respective ECG signal portion of the historical collection of the plurality of ECG signal portions (or a second plurality thereof), determining at least one error value based on the predicted type of arrhythmia and the known arrhythmia type information (e.g., a respective annotations associated with a known type of arrhythmia for each respective ECG signal portion), and training the arrhythmia type classifier (e.g., updating the weights thereof and/or the like) based on the error value(s) (e.g., using back propagation and/or the like). In some embodiments, the error value(s) may include one of a prediction error or a contrastive loss.

As shown in FIG. 3B, at 314*b*, remote computer system 304*b* may communicate a historical collection of a plurality of ECG signal portions and information related thereto (e.g., known rhythm change information and/or the like) to heart monitoring device 302*b* and/or gateway device 329*b*, as described herein.

In some embodiments, gateway device 329*b* may enable communication between heart monitoring device 302*b* and remote computer system 304*b*, as described herein.

As shown in FIG. 3B, at 316*b*, heart monitoring device 302*b* and/or gateway device 329*b* may train a rhythm change classifier, which may be implemented by at least one non-transitory computer readable medium (e.g., e.g., a memory, a programmable circuit board, a field programmable gate array (FPGA), an integrated circuit, any combination thereof, and/or the like) that may be installed in and/or part of heart monitoring device 302*b* and/or gateway device 329*b*, as described herein.

In some embodiments, heart monitoring device 302*b* may be an external heart monitoring device for a patient, as described herein. For example, (external) heart monitoring device 302*b* may include a plurality of ECG electrodes configured to sense surface ECG activity of the patient. Additionally or alternatively, (external) heart monitoring device 302*b* may include ECG processing circuitry configured to process the surface ECG activity of the patient to provide at least one ECG signal for the patient on at least one ECG channel.

In some embodiments, (external) heart monitoring device 302*b* may include a non-transitory computer-readable medium (e.g., a memory, a programmable circuit board, a field programmable gate array, an integrated circuit, any combination thereof, and/or the like) including (e.g., implementing, embodying, storing, and/or the like) the rhythm change classifier (which may include, e.g., at least one neural network), as described herein. Additionally or alternatively, (external) heart monitoring device 302*b* may include at least one processor operatively connected to the ECG channel(s) and the non-transitory computer-readable medium.

In some embodiments, gateway device 329*b* may include a non-transitory computer-readable medium (e.g., a memory, a programmable circuit board, a field programmable gate array, an integrated circuit, any combination thereof, and/or the like) including (e.g., implementing, embodying, storing, and/or the like) the trained rhythm change classifier (which may include, e.g., at least one neural network trained based on the historical collection of a plurality of ECG signal portions with known rhythm change information), as described herein. Additionally or alternatively, gateway device 329*b* may include at least one processor operatively connected to the non-transitory computer-readable medium.

In some embodiments, a rhythm change classifier may include at least one neural network, as described herein. Additionally or alternatively, the at least one neural network may include at least one of a convolutional neural network, a recurrent neural network, an attention network, a fully connected neural network, any combination thereof, and/or the like, as described herein. In some embodiments, the neural network(s) may include a plurality of Siamese branches (e.g., each respective Siamese branch associated with a respective ECG channel), as described herein.

In some embodiments, heart monitoring device 302*b* and/or gateway device 329*b* may train the rhythm change classifier by predicting, with the rhythm change classifier, predicted rhythm change information (e.g., data (e.g., probability, confidence score, and/or the like) associated with a predicted rhythm change, data (e.g., probability, confidence score, and/or the like) associated with a lack of a predicted rhythm change, and/or the like) for each ECG signal portion of the historical collection of the plurality of ECG signal portions, determining at least one error value based on the predicted rhythm change information and the known rhythm change information, and training the rhythm change classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, the historical collection of the plurality of ECG signal portions may include a first ECG signal portion associated with a first time and a second ECG signal portion associated with a second time after the first time, as described herein. Additionally or alternatively, heart monitoring device 302*b* and/or gateway device 329*b* may train the rhythm change classifier by predicting, with the rhythm change classifier, a predicted ECG signal portion associated with the second time based on the first ECG signal portion, determining at least one error value based on the predicted ECG signal portion and the second ECG signal portion, and training the rhythm change classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, the historical collection of the plurality of ECG signal portions may include a first ECG signal portion associated with a first time and a second ECG signal portion associated with a second time, as described herein. Additionally or alternatively, heart monitoring device 302*b* and/or gateway device 329*b* may train the rhythm change classifier by predicting, with the rhythm change classifier, a predicted time associated with the second ECG signal portion based on the a first ECG signal portion and the second ECG signal, determining at least one error value based on the predicted time and the second time, and training the rhythm change classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, there may be an insufficient number of ECG signal portions in the historical collection of the plurality of ECG signal portions with known rhythm change information to train the rhythm change classifier to perform the desired task (e.g., detect and/or identify at least one predetermined rhythm changes), as described herein. Additionally or alternatively, there may be sufficient data (e.g., historical ECG signal portions and/or the like) to train the rhythm change classifier to perform a separate task (e.g., which may be related in some way to the target task), as described herein. In some embodiments, the rhythm change classifier may be trained to perform the separate task (e.g., counting R-peaks, determining heart rate, and/or the like based on the ECG signal(s)), as described herein. Additionally or alternatively, the rhythm change classifier may then be adapted to perform the target task, as described herein. For example, in some embodiments, the rhythm change classifier may be retrained using the limited amount of ECG signal portions in the historical collection of the plurality of ECG signal portions with known rhythm change information and/or the like, as described herein. Additionally or alternatively, the rhythm change classifier may be used to perform the separate task (e.g., counting R-peaks, determining heart rate, and/or the like based on the ECG signal(s)), and the output thereof may be applied to the target task, as described herein. For example, the processor (e.g., of heart monitoring device 302b and/or gateway device 329b) may detect, with the rhythm change classifier, at least one of a count of peaks or a heart rate based on the at least one ECG signal, as described herein. Additionally or alternatively, the processor (e.g., of heart monitoring device 302b and/or gateway device 329b) may determine the detected at least one of the count of peaks or the heart rate is above a first threshold (e.g., tachycardia onset threshold) for the patient or below a second threshold (e.g., bradycardia onset threshold) for the patient (e.g., wherein the second threshold for the patient may be less than the first threshold for the patient), as described herein.

In some embodiments, there may be an insufficient number of ECG signal portions associated with (e.g., sensed from and/or the like) the plurality of ECG electrodes of the heart monitoring device 302b in the historical collection of the plurality of ECG signal portions with known rhythm change information to train the rhythm change classifier for the ECG signal(s) received form the plurality of ECG electrodes of the heart monitoring device 302a, as described herein. Additionally or alternatively, there may be sufficient data (e.g., historical ECG signal portions and/or the like) associated with (e.g., sensed from and/or the like) a second plurality of ECG electrodes (e.g., electrodes from an ECG device separate from the heart monitoring device 302b, such as a 12-lead ECG sensor, a separate external and/or wearable heart monitoring device, and/or the like) independent of the plurality of ECG electrodes of the heart monitoring device 302a to train the rhythm change classifier based on the second plurality of ECG electrodes, as described herein. In some embodiments, the rhythm change classifier may be trained based on the ECG signal portion(s) associated with (e.g., sensed from and/or the like) the second plurality of ECG electrodes, as described herein. Additionally or alternatively, the rhythm change classifier may then be adapted to detect the predetermined rhythm change(s) based on the plurality of ECG electrodes of heart monitoring device 202b, as described herein. In some embodiments, heart monitoring device 202b and/or gateway device 329b may determine (e.g., calculate and/or the like) a transform (e.g., vector projection and/or the like) of the ECG signal portion(s) associated with the second plurality of ECG electrodes to the plurality of ECG electrodes of heart monitoring device 302b, and the transform of the ECG signal portion(s) may be used to train the rhythm change classifier as if the ECG signal portions were associated with (e.g., sensed from and/or the like) the plurality of ECG electrodes of the heart monitoring device 302b, as described herein.

As shown in FIG. 3B, at 318b, heart monitoring device 302b and/or gateway device 329b (e.g., the processor(s) thereof) may be configured to receive the ECG signal(s). In some embodiments, heart monitoring device 302a may be configured to receive the ECG signal(s) via the ECG channel(s), as described herein. Additionally or alternatively, heart monitoring device 302a may be configured to communicate (e.g., transmit) the ECG signal(s) to gateway device 329a, and/or gateway device 329a may receive the ECG signals from heart monitoring device 302a, as described herein.

As shown in FIG. 3B, at 320b, heart monitoring device 302b and/or gateway device 329b (e.g., the processor(s) thereof) may be configured to detect with the rhythm change classifier time data corresponding to a predetermined rhythm change in ECG signal(s), as described herein.

In some embodiments, the neural network(s) of the rhythm change classifier (e.g., of heart monitoring device 302b and/or gateway device 329b) may include a plurality of Siamese branches, as described herein.

In some embodiments, heart monitoring device 302b and/or gateway device 329b (e.g., processor(s) thereof) may be further configured to detect (e.g., with the trained rhythm change classifier) the predetermined rhythm change based on the at least one ECG signal, as described herein. In some embodiments, heart monitoring device 302b may further include at least one sensor and associated sensor circuitry configured to sense non-ECG biometric data of the patient (which, in some embodiments, may be communicated to gateway device 329b), as described herein. Additionally or alternatively, detecting the predetermined rhythm change may be further based on the non-ECG biometric data of the patient (e.g., non-ECG biometric data of the patient may be input into the neural network(s) of the rhythm change classifier, may be combined with the output of the rhythm change classifier, and/or the like), as described herein.

In some embodiments, detecting the predetermined rhythm change may be further based on at least one baseline ECG signal portion of the patient, as described herein.

In some embodiments, detecting the predetermined rhythm change may be further based on at least one calibration measurement of the patient, as described herein.

In some embodiments, detecting the predetermined rhythm change may be further based on at least one reference vector of the patient, as described herein.

In some embodiments, detecting the predetermined rhythm change may be further based on at least one previous ECG signal portion, as described herein.

In some embodiments, the processor (e.g., of heart monitoring device 302b and/or gateway device 329b) may further determine (e.g., with the rhythm change classifier) a confidence score associated with the predetermined rhythm change based on the at least one ECG signal, as described herein.

As shown in FIG. 3B, at 322b, heart monitoring device 302a and/or gateway device 329b (e.g., the processor(s) thereof) may be configured to determine based on the detected time data at least one ECG signal portion associated with the detected time data corresponding to the predetermined rhythm change in the ECG signal(s), as described herein.

As shown in FIG. 3B, at 324b, heart monitoring device 302b and/or gateway device 329b (e.g., the processor(s) thereof) may communicate (e.g., transmit and/or the like) the determined ECG signal portion(s) to remote computer system 304b, as described herein. Additionally or alternatively, heart monitoring device 302b and/or gateway device 329b (e.g., the processor(s) thereof) may be configured to communicate an indication (e.g., a flag, an indicator, a confidence score, a mark, metadata, the time data, and/or the like) associated with the predetermined rhythm change detected (e.g., identified and/or the like) in the ECG signal portion(s), as described herein.

In some embodiments, the processor (e.g., of heart monitoring device 302b and/or gateway device 329b) may further communicate (e.g., transmit and/or the like) at least one second ECG signal portion of the ECG signal(s) to remote computer system 304b, as described herein. Additionally or alternatively, the second ECG signal portion(s) may be independent of the detected time data corresponding to the predetermined rhythm change in the ECG signal(s), as described herein.

In some embodiments, gateway device 329b may enable communication between heart monitoring device 302b and remote computer system 304b, as described herein.

In some embodiments, remote computing system 304b may receive the determined ECG signal portion(s) (e.g., from heart monitoring device 302b and/or gateway device 329b), as described herein.

As shown in FIG. 3B, at 326b, remote computing system 304b may analyze the determined ECG signal portion(s) to classify a type of arrhythmia for the rhythm change(s) in the ECG signal(s), as described herein. For example, remote computer system 304b may include an arrhythmia type classifier (e.g., including at least one (second) neural network trained based on a (second) historical collection of a (second) plurality of ECG signal portions with known arrhythmia type information), as described herein.

In some embodiments, remote computer system 304b may analyze the determined ECG signal portion(s) to identify at least one arrhythmia associated with the rhythm change in the at least one ECG signal, as described herein. In some embodiments, the arrhythmia may be one or more rare arrhythmias on which the remote computer system 204a may have previously been trained. Additionally or alternatively, remote computer system 204a may use any suitable signal processing technique (e.g., separate from or including the arrhythmia type classifier as described herein) to identify the rare arrhythmia(s), as described herein.

In some embodiments, the determined ECG signal portion(s) may include a plurality of determined ECG signal portions, as described herein. Additionally or alternatively, remote computer system 304b may receive the plurality of determined ECG signal portions from heart monitoring device 302b and/or gateway device 329b, as described herein. In some embodiments, remote computer system 304b may analyze each respective determined ECG signal portion to classify a respective class for each respective determined ECG signal portion, as described herein.

As shown in FIG. 3B, at 328b, remote computer system 304b may communicate (e.g., transmit and/or the like) at least one message associated with the determined ECG signal portion(s) and/or the type of arrhythmia associated with the rhythm change, as described herein. For example, the message(s) may be communicated from remote computer system 304b to technician device 308b, as described herein.

In some embodiments, remote computer system 304b may transmit at least one message associated with the second ECG signal portion(s) (e.g., randomly determined second ECG signal portion(s), second ECG signal portion(s) determined to have a confidence score below a first threshold and above a second threshold, and/or the like, as described herein) to technician device 308b, as described herein.

In some embodiments, remote computer system 304b may transmit at least one message associated with the at least two respective determined ECG signal portions and the first class to technician device 308b, as described herein.

As shown in FIG. 3B, at 330b, technician device 308b may receive at least one annotation associated with the ECG signal portion(s), e.g., via input from a user (e.g., a technician and/or the like).

As shown in FIG. 3B, at 332b, remote computer system 304b may receive annotation data associated with at least one annotation from technician device 308a, as described herein. For example, the annotation data may be communicated from technician device 308b to remote computer system 304b, as described herein. Additionally or alternatively, the ECG signal portion(s) associated with such annotation(s) may be communicated with the annotation data, as described herein.

In some embodiments, remote computer system 304b may receive (e.g., from technician device 308b) annotation data associated with at least one annotation for the second ECG signal portion(s) (e.g., randomly determined second ECG signal portion(s), second ECG signal portion(s) determined to have a confidence score below a first threshold and above a second threshold, and/or the like, as described herein).

As shown in FIG. 3B, at 334b, remote computer system 304a may retrain the arrhythmia type classifier based on the historical collection of the plurality of ECG signal portions with the known rhythm change information, the second ECG signal portion(s), and the annotation data associated therewith, as described herein.

As shown in FIG. 3B, at 336b, remote computer system 304b may communicate (e.g., transmit, write, and/or the like) the annotation data to data repository 306b, as described herein. Additionally or alternatively, the ECG signal portion(s) associated with such annotation(s) may be communicated with the annotation data, as described herein.

In some embodiments, annotation data and the ECG signal portion(s) associated with such annotation(s) may be added to the historical collection of the plurality of ECG signal portions, as described herein. In some embodiments, remote computer system 304b may retrain the arrhythmia type classifier based on the historical collection of the plurality of ECG signal portions with the known arrhythmia type information (which may now include the ECG signal portion(s) and/or the annotation data associated therewith).

In some embodiments, remote computer system 304b may add annotation data associated with at least one annotation for the second ECG signal portion(s) (e.g., randomly determined second ECG signal portion(s), second ECG signal portion(s) determined to have a confidence score below a first threshold and above a second threshold, and/or the like, as described herein) to the historical collection of the plurality of ECG signal portions in data repository 306b, as described herein. In some embodiments, remote computer system 304b may retrain the arrhythmia type classifier based on the historical collection of the plurality of ECG signal portions with the known arrhythmia type information (which may now include the second ECG signal portion(s) and/or the annotation data associated therewith), as described herein.

As shown in FIG. 3B, at 338b, remote computer system 304b may communicate (e.g., transmit and/or the like) the annotation data associated with at least one annotation for the second ECG signal portion(s) to heart monitoring device 302*b* and/or gateway device 329*b*, as described herein. Additionally or alternatively, heart monitoring device 302*b* and/or gateway device 329*b* (e.g., processor(s) thereof) may retrain the rhythm change classifier (and/or train an updated rhythm change classifier) based on the historical collection of the plurality of ECG signal portions with the known rhythm change information, the second ECG signal portion(s), and the annotation data associated therewith, as described herein.

Referring now to FIG. 3C, FIG. 3C shows an example swim lane diagram of a process 300*c* for arrhythmia monitoring, according to some embodiments. In addition to system components, the process 300*c* also shows communication flows between the system components. As shown in FIG. 3C, in some embodiments, remote computer system 304*c* may be the same as or similar to remote computer system 104, remote computer systems 204*a*, 204*b*, and/or 204*c*, remote computer systems 304*a* and/or 304*b*, and/or the like. In some embodiments, data repository 306*c* may be the same as or similar to data repository 106, data repositories 206*a*, 206*b*, and/or 206*c*, data repositories 306*a* and/or 306*b*, and/or the like. In some embodiments, technician device 308*c* may be the same as or similar to technician device 108, technician devices 208*a*, 208*b*, and/or 208*c*, technician devices 308*a* and/or 308*b*, and/or the like. In some embodiments, supervisor device 310*c* may be the same as or similar to supervisor device 110, supervisor device 210*c*, and/or the like.

As shown in FIG. 3C, at 312*c*, remote computer system 304*c* may receive (e.g., retrieve, search for, send a request and/or query to cause data repository 206*c* to communicate, and/or the like) a historical collection of a plurality of ECG signal portions and information related thereto (e.g., known arrhythmia type information and/or the like), e.g., from data repository 306*c*, as described herein.

As shown in FIG. 3C, at 314*c*, remote computer system 304*c* may train at least one neural network of at least one classifier (e.g., an arrhythmia type classifier and/or the like) based on the historical collection of a plurality of ECG signal portions and information related thereto (e.g., known arrhythmia type information and/or the like), as described herein.

In some embodiments, an arrhythmia type classifier may include at least one neural network (e.g., at least one second neural network), as described herein. Additionally or alternatively, the at least one (second) neural network may include at least one of a deep neural network, a convolutional neural network, a recurrent neural network, an attention network, a fully connected neural network, any combination thereof, and/or the like, as described herein. In some embodiments, the neural network(s) may include a plurality of Siamese branches (e.g., each respective Siamese branch associated with a respective ECG channel), as described herein.

In some embodiments, remote computer system 304*c* may train an arrhythmia type classifier by predicting, with the arrhythmia type classifier, a predicted type of arrhythmia in each respective ECG signal portion of the historical collection of the plurality of ECG signal portions (or a second plurality thereof), determining at least one error value based on the predicted type of arrhythmia and the known arrhythmia type information (e.g., a respective annotations associated with a known type of arrhythmia for each respective ECG signal portion), and training the arrhythmia type classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, the known arrhythmia type information may include a plurality of annotations, as described herein. For example, each annotation may be associated with a respective ECG signal portion of the plurality of ECG signal portions, as described herein. In some embodiments, remote computer system 304*c* may train the arrhythmia type classifier based on the plurality of ECG signals and the plurality of annotations, as described herein.

In some embodiments, the plurality of annotations may be from a plurality of technicians (e.g., a plurality of technician devices 308*c* and/or the like), as described herein. Additionally or alternatively, each annotation annotations may be associated with a respective technician of the plurality of technicians and/or a respective ECG signal portion of the plurality of ECG signal portions, as described herein. In some embodiments, the arrhythmia type classifier may be trained separately for each technician, as described herein. For example, for a first technician of the plurality of technicians, the arrhythmia type classifier may be trained (e.g., by remote computer system 304*c*) based on a subset of the plurality of ECG signals and the plurality of annotations associated with at least one other technician of the plurality of technicians different than the first technician, as described herein.

In some embodiments, each annotation may be associated with one possible type of arrhythmia (e.g., a label associated with a possible type of arrhythmia, a text string identifying at least one possible type arrhythmia, and/or the like) of the respective ECG signal(s) and/or portion(s) thereof, as described herein.

In some embodiments, there may be an insufficient number of ECG signal portions associated with (e.g., sensed from and/or the like) at least one second ECG electrode in the historical collection of the plurality of ECG signal portions with known arrhythmia type information (e.g., annotations, labels, and/or the like) to train the arrhythmia type classifier for the ECG signal(s) received from the second ECG electrode(s), as described herein. Additionally or alternatively, there may be sufficient data (e.g., historical ECG signal portions and/or the like) associated with (e.g., sensed from and/or the like) at least one first ECG electrode (e.g., electrodes from an ECG device separate from the second ECG electrode(s), such as a 12-lead ECG sensor, a separate external and/or wearable heart monitoring device, and/or the like) independent of the second ECG electrode(s) to train the rhythm change classifier based on the second ECG electrode(s), as described herein. In some embodiments, the known arrhythmia type information may include a plurality of annotations, each of which may be associated with a respective ECG signal portion of a first plurality of ECG signal portions associated with the first ECG electrode(s), as described herein. In some embodiments, each respective ECG signal portion of a second plurality of ECG signal portions associated with the second ECG electrode(s) may correspond to a respective ECG signal portion of the first plurality of ECG signal portions, as described herein. In some embodiments, remote computer system 304*c* may train the arrhythmia type classifier by predicting, with the arrhythmia type classifier, a predicted type of arrhythmia in each respective ECG signal portion of the second plurality of ECG signal portions, determining at least one error value based on the predicted type of arrhythmia and the respective annotation of the plurality of annotations associated with a respective ECG signal portion of the first plurality of ECG signal portions corresponding to the respective ECG signal portion of the second plurality of ECG signal portions, and training (e.g., updating the weights of and/or the like) the arrhythmia type classifier based on the at least one error value (e.g., based on back propagation and/or the like), as described herein.

In some embodiments, ECG signal portions associated with multiple electrodes may be combined (e.g., by vector addition, vector projection, a transform, and/or the like) to form extrapolated ECG signal portions that may be more familiar and/or suitable for review by a human user (e.g., technician and/or the like), as described herein. For example, the historical collection of the plurality of ECG signal portions may include a first plurality of ECG signal portions of at least one first ECG signal based on first surface ECG activity sensed by at least one first ECG electrode and a second plurality of ECG signal portions of at least one second ECG signal based on second surface ECG activity sensed by at least one second ECG electrode, as described herein. In some embodiments, each ECG signal portion of the first plurality of ECG signal portions may be combined (e.g., by vector addition, vector projection, a transform, and/or the like) with a respective ECG signal portion of the second plurality of ECG signal portions to form a plurality of extrapolated ECG signal portions (e.g., by remote computer system 304c), as described herein. In some embodiments, the known arrhythmia type information may include a plurality of annotations, as described herein. Additionally or alternatively, each respective annotation may be associated with a respective extrapolated ECG signal portion of the plurality of extrapolated ECG signal portions, as described herein.

In some embodiments, at least some of the plurality of ECG signal portions of the historical collection may be time warped (e.g., time dilated and/or the like) to form a plurality of warped ECG signal portions (e.g., by remote computer system 304c using any suitable signal processing technique for time warping, time dilation, and/or the like), as described herein.

In some embodiments, at least some of the plurality of ECG signal portions of the historical collection may be at least one of filtered, inverted, any combination thereof, and/or the like (e.g., by remote computer system 304c), as described herein.

In some embodiments, at least one noise signal portion may be combined with at least some of the plurality of ECG signal portions of the historical collection (e.g., by remote computer system 304c), as described herein.

In some embodiments, at least some of the plurality of ECG signal portions of the historical collection may be style transferred (e.g., by remote computer system 304c), as described herein.

As shown in FIG. 3C, at 316c, remote computer system 304c may receive at least one ECG signal and annotation data associated with at least one annotation for each ECG signal, as described herein.

As shown in FIG. 3C, at 318c, remote computer system 304c may detect, with the arrhythmia type classifier, a type of arrhythmia in the ECG signal(s) and time data associated with the detected type of arrhythmia, as described herein. For example, the time data may include at least one of a start time, a time interval, any combination thereof, and/or the like, as described herein. In some embodiments, remote computer system 304c may determine, based on the time data, at least one ECG signal portion associated with the detected type of arrhythmia in the ECG signal(s), as described herein.

In some embodiments, remote computer system 304c may determine a plausibility score for the annotation(s) based on the detected type of arrhythmia. For example, an output of at least one neural network of the arrhythmia type classifier may include a confidence score (e.g., a probability and/or the like) associated with each possible type of arrhythmia, as described herein. For example, the type of arrhythmia determined by the arrhythmia type classifier may be the type of arrhythmia with a highest confidence score (e.g., probability and/or the like). Additionally or alternatively, each annotation may be associated with one possible type of arrhythmia (e.g., a label associated with a possible type of arrhythmia, a text string identifying at least one possible type arrhythmia, and/or the like). In some embodiments, plausibility score of each annotation may be the confidence score (e.g., determined by the arrhythmia type classifier) of the possible type of arrhythmia associated with such annotation. In some embodiments, the arrhythmia type classifier may include a plurality of neural networks, and each such neural network may output a confidence score associated with at least one possible type of arrhythmia.

As shown in FIG. 3C, at 320c, remote computer system 304c may generate at least one message based on the at least one determined ECG signal portion and the plausibility score for the at least one annotation, as described herein. For example, the message(s) may indicate at least one of a recommendation to annotate the at least one determined ECG signal portion based on the detected type of arrhythmia, a recommendation to reevaluate the annotation data associated with the at least one determined ECG signal portion based on the plausibility score, and/or the like.

In some embodiments, remote computer system 304c may to determine the plausibility score is below a threshold. Additionally or alternatively, generating the message(s) may include remote computer system 304c generating, based on the determination that the plausibility score is below the threshold, the at least one message indicating the recommendation to reevaluate the annotation data associated with the at least one determined ECG signal portion, as described herein.

As shown in FIG. 3C, at 322c, remote computer system 304c may transmit the at least some of the message(s) associated with the at least one determined ECG signal portion to technician device 308c, as described herein.

As shown in FIG. 3C, at 324c, remote computer system 204c may transmit the at least some of the message(s) associated with the at least one determined ECG signal portion to supervisor device 310c, as described herein.

Referring now to FIG. 4A, FIG. 4A shows an example flow chart of a process 400a for arrhythmia monitoring, according to some embodiments. In some embodiments, one or more of the steps of process 400a may be performed (e.g., completely, partially, and/or the like) by heart monitoring device 102. In some non-limiting embodiments, one or more of the steps of process 400a may be performed (e.g., completely, partially, and/or the like) by another system, another device, another group of systems, or another group of devices, separate from or including heart monitoring device 102, such as remote computer system 104, data repository 106, technician device 108, gateway device 129, and/or the like.

As shown in FIG. 4A, at step 402a, a rhythm change classifier may be received and/or installed. For example, heart monitoring device 102 and/or gateway device 129 may receive (e.g., from remote computer system 104, data repository 106, and/or the like) and/or have installed thereon (e.g., in a non-transitory computer readable medium of heart monitoring device 102 and/or gateway device 129) a rhythm change classifier (and/or a plurality of weights thereof), as described herein. For example, the rhythm change classifier may include at least one neural network trained based on a historical collection of a plurality of ECG signal portions with known rhythm change information, as described herein.

In some embodiments, remote computer system 104 may train the rhythm change classifier, as described herein. Additionally or alternatively, remote computer system 104 may communicate the trained rhythm change classifier to heart monitoring device 102 and/or gateway device 129, as described herein.

In some embodiments, gateway device 129 may enable communication between heart monitoring device 102 and remote computer system 104, as described herein.

As shown in FIG. 4A, at step 404a, at least one ECG signal may be received. For example, heart monitoring device 102 and/or gateway device 129 (e.g., the processor(s) thereof) may receive at least one ECG signal. In some embodiments, heart monitoring device 102 may be configured to receive the ECG signal(s) via at least one ECG channel, as described herein. Additionally or alternatively, heart monitoring device 102 may be configured to communicate (e.g., transmit) the ECG signal(s) to gateway device 129, and/or gateway device 129 may receive the ECG signals from heart monitoring device 102, as described herein.

As shown in FIG. 4A, at step 406a, at least one of predetermined rhythm change and/or a time thereof may be detected. For example, heart monitoring device 102 and/or gateway device 129 (e.g., the processor(s) thereof) may detect, with the rhythm change classifier, time data corresponding to a predetermined rhythm change in the at least one ECG signal, as described herein. Additionally or alternatively, heart monitoring device 102 and/or gateway device 129 (e.g., the processor(s) thereof) may detect, with the rhythm change classifier, the predetermined rhythm change based on the at least one ECG signal, as described herein.

In some embodiments, heart monitoring device 102 and/or gateway device 129 (e.g., processor(s) thereof) may detect (e.g., with the trained rhythm change classifier) the predetermined rhythm change based on the at least one ECG signal. In some embodiments, heart monitoring device 102 may further include at least one sensor and associated sensor circuitry configured to sense non-ECG biometric data of the patient (which, in some embodiments, may be communicated to gateway device 129), as described herein. Additionally or alternatively, detecting the predetermined rhythm change may be further based on the non-ECG biometric data of the patient (e.g., non-ECG biometric data of the patient may be input into the neural network(s) of the rhythm change classifier, may be combined with the output of the rhythm change classifier, and/or the like), as described herein In some embodiments, detecting the predetermined rhythm change may be further based on at least one baseline ECG signal portion of the patient, as described herein.

In some embodiments, detecting the predetermined rhythm change may be further based on at least one calibration measurement of the patient, as described herein.

In some embodiments, detecting the predetermined rhythm change may be further based on at least one reference vector of the patient, as described herein.

In some embodiments, detecting the predetermined rhythm change may be further based on at least one previous ECG signal portion, as described herein.

In some embodiments, the heart monitoring device 102 and/or gateway device 129 (e.g., processor(s) thereof) may further determine (e.g., with the rhythm change classifier) a confidence score associated with the predetermined rhythm change based on the at least one ECG signal, as described herein.

As shown in FIG. 4A, at step 408a, at least one ECG signal portion may be determined (e.g., based on the detected time data, the detected predetermined rhythm change, and/or the like. For example, heart monitoring device 102 and/or gateway device 129 (e.g., the processor(s) thereof) may determine (e.g., based on the detected time data) at least one ECG signal portion associated with the detected time data corresponding to the predetermined rhythm change in the ECG signal(s), as described herein.

As shown in FIG. 4A, at step 410a, the ECG signal portion(s) may be transmitted. For example, heart monitoring device 102 and/or gateway device 129 may communicate (e.g., transmit and/or the like) the determined ECG signal portion(s) to remote computer system 104, as described herein. Additionally or alternatively, heart monitoring device 102 and/or gateway device 129 (e.g., the processor(s) thereof) may communicate an indication (e.g., a flag, an indicator, a confidence score, a mark, metadata, the time data, and/or the like) associated with the predetermined rhythm change detected (e.g., identified and/or the like) in the ECG signal portion(s).

In some embodiments, heart monitoring device 102 and/or gateway device 129 (e.g., the processor(s) thereof) may further communicate (e.g., transmit and/or the like) at least one second ECG signal portion of the ECG signal(s) to remote computer system 104, as described herein. Additionally or alternatively, the second ECG signal portion(s) may be independent of the detected time data corresponding to the predetermined rhythm change in the ECG signal(s), as described herein.

In some embodiments, gateway device 129 may enable communication between heart monitoring device 102 and remote computer system 104, as described herein.

In some embodiments, remote computing system 104 may receive the determined ECG signal portion(s) (e.g., from heart monitoring device 102 and/or gateway device 129).

As shown in FIG. 4A, at step 412a, a retrained (e.g., updated and/or the like) rhythm change classifier may be received. For example, heart monitoring device 102 and/or gateway device 129 may receive the retrained (e.g., updated and/or the like) rhythm change classifier from remote computer system 104.

In some embodiments, remote computing system 104 may analyze the determined ECG signal portion(s) to classify a type of arrhythmia for the rhythm change(s) in the ECG signal(s), as described herein. For example, remote computer system 204a may include an arrhythmia type classifier (e.g., including at least one (second) neural network trained based on a (second) historical collection of a (second) plurality of ECG signal portions with known arrhythmia type information), as described herein.

In some embodiments, remote computer system 104 may communicate (e.g., transmit and/or the like) at least one message associated with the determined ECG signal portion(s) and/or the type of arrhythmia associated with the rhythm change, as described herein. For example, the message(s) may be communicated from remote computer system 104 to technician device 108, as described herein.

In some embodiments, remote computer system 104 may transmit at least one message associated with the second ECG signal portion(s) (e.g., randomly determined second ECG signal portion(s), second ECG signal portion(s) determined to have a confidence score below a first threshold and above a second threshold, and/or the like, as described herein) to technician device 108, as described herein.

In some embodiments, technician device 108 may receive at least one annotation associated with the ECG signal portion(s), e.g., via input from a user (e.g., a technician and/or the like). Additionally or alternatively, remote computer system 104 may receive annotation data associated with the annotation(s) from technician device 108, as described herein.

In some embodiments, remote computer system 104 may retrain the rhythm change classifier (and/or train an updated rhythm change classifier) based on the historical collection of the plurality of ECG signal portions with the known rhythm change information, the second ECG signal portion(s), and the annotation data associated therewith, as described herein (e.g., before and/or after adding the second ECG signal portion(s) and the annotation data associated therewith to the historical collection, as described herein).

In some embodiments, remote computer system 104 may communicate the retrained rhythm change classifier (and/or trained updated rhythm change classifier) to heart monitoring device 102 and/or gateway device 129, as described herein. Additionally or alternatively, a copy of the retrained rhythm change classifier (and/or trained updated rhythm change classifier) may be downloaded from remote computer system 104 and/or installed on (e.g., uploaded to, written to, configured on, and/or the like) at least one non-transitory computer readable medium (e.g., e.g., memory, programmable circuit board, FPGA, integrated circuit, any combination thereof, and/or the like), which may be installed in and/or part of heart monitoring device 102 and/or gateway device 129.

In some non-limiting embodiments, process 400a may include repeating at least some steps (e.g., steps 404a-410a, 404a-412a, and/or the like). For example, at least some such steps may be repeated continuously, periodically, and/or the like. For example, ECG signal(s) may be received (404a) continuously. Additionally or alternatively, received ECG signals may be analyzed using the rhythm change classifier continuously. For example, predetermined rhythm changes and/or time data associated therewith may be detected (406a) as often as rhythm changes occur in the ECG signal(s). Additionally or alternatively, the ECG signal portion(s) may be determined (408a) and/or transmitted (410a) as often as rhythm changes and/or time data associated therewith may be detected. For example, the rhythm change classifier may be retrained (412a) periodically, continuously, and/or the like.

Referring now to FIG. 4B, FIG. 4B shows an example flow chart of a process 400b for arrhythmia monitoring, according to some embodiments. In some embodiments, one or more of the steps of process 400b may be performed (e.g., completely, partially, and/or the like) by heart monitoring device 102. In some non-limiting embodiments, one or more of the steps of process 400b may be performed (e.g., completely, partially, and/or the like) by another system, another device, another group of systems, or another group of devices, separate from or including heart monitoring device 102, such as remote computer system 104, data repository 106, technician device 108, gateway device 129, and/or the like.

As shown in FIG. 4B, at step 402b, a historical collection of a plurality of ECG signal portions and information related thereto (e.g., known rhythm change information and/or the like) may be received. For example, heart monitoring device 102 and/or gateway device 129 may receive the historical collection of a plurality of ECG signal portions and/or information related thereto from remote computer system 104, data repository 106, and/or the like, as described herein.

As shown in FIG. 4B, at step 404b, remote computer system a rhythm change classifier may be trained. For example, heart monitoring device 102 and/or gateway device 129 may train the rhythm change classifier, which may be implemented by at least one non-transitory computer readable medium (e.g., e.g., a memory, a programmable circuit board, a field programmable gate array (FPGA), an integrated circuit, any combination thereof, and/or the like) that may be installed in and/or part of heart monitoring device 102 and/or gateway device 129, as described herein.

In some embodiments, heart monitoring device 102 may be an external heart monitoring device for a patient, as described herein.

In some embodiments, a rhythm change classifier may include at least one neural network, as described herein. Additionally or alternatively, the at least one neural network may include at least one of a convolutional neural network, a recurrent neural network, an attention network, a fully connected neural network, any combination thereof, and/or the like, as described herein. In some embodiments, the neural network(s) may include a plurality of Siamese branches (e.g., each respective Siamese branch associated with a respective ECG channel), as described herein.

In some embodiments, heart monitoring device 102 and/or gateway device 129 may train the rhythm change classifier by generating, with the rhythm change classifier, predicted rhythm change information (e.g., data (e.g., probability, confidence score, and/or the like) associated with a predicted rhythm change, data (e.g., probability, confidence score, and/or the like) associated with a lack of a predicted rhythm change, and/or the like) for each ECG signal portion of the historical collection of the plurality of ECG signal portions, determining at least one error value based on the predicted rhythm change information and the known rhythm change information, and updating the rhythm change classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, the historical collection of the plurality of ECG signal portions may include a first ECG signal portion associated with a first time and a second ECG signal portion associated with a second time after the first time, as described herein. Additionally or alternatively, heart monitoring device 102 and/or gateway device 129 may train the rhythm change classifier by predicting, with the rhythm change classifier, a predicted ECG signal portion associated with the second time based on the first ECG signal portion, determining at least one error value based on the predicted ECG signal portion and the second ECG signal portion, and training the rhythm change classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, the historical collection of the plurality of ECG signal portions may include a first ECG signal portion associated with a first time and a second ECG signal portion associated with a second time, as described herein. Additionally or alternatively, heart monitoring device 102 and/or gateway device 129 may train the rhythm change classifier by predicting, with the rhythm change classifier, a predicted time associated with the second ECG signal portion based on the a first ECG signal portion and the second ECG signal, determining at least one error value based on the predicted time and the second time, and training the rhythm change classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, there may be an insufficient number of ECG signal portions in the historical collection of the plurality of ECG signal portions with known rhythm change information to train the rhythm change classifier to perform the desired task (e.g., detect and/or identify at least one predetermined rhythm changes), as described herein. Additionally or alternatively, there may be sufficient data (e.g., historical ECG signal portions and/or the like) to train the rhythm change classifier to perform a separate task (e.g., which may be related in some way to the target task), as described herein. In some embodiments, the rhythm change classifier may be trained to perform the separate task (e.g., counting R-peaks, determining heart rate, and/or the like based on the ECG signal(s)), as described herein. Additionally or alternatively, the rhythm change classifier may then be adapted to perform the target task, as described herein. For example, in some embodiments, the rhythm change classifier may be retrained using the limited amount of ECG signal portions in the historical collection of the plurality of ECG signal portions with known rhythm change information and/or the like, as described herein. Additionally or alternatively, the rhythm change classifier may be used to perform the separate task (e.g., counting R-peaks, determining heart rate, and/or the like based on the ECG signal(s)), and the output thereof may be applied to the target task, as described herein. For example, the processor (e.g., of heart monitoring device 102 and/or gateway device 129) may detect, with the rhythm change classifier, at least one of a count of peaks or a heart rate based on the at least one ECG signal, as described herein. Additionally or alternatively, the processor (e.g., of heart monitoring device 102 and/or gateway device 129) may determine the detected at least one of the count of peaks or the heart rate is above a first threshold (e.g., tachycardia onset threshold) for the patient or below a second threshold (e.g., bradycardia onset threshold) for the patient (e.g., wherein the second threshold for the patient may be less than the first threshold for the patient), as described herein.

In some embodiments, there may be an insufficient number of ECG signal portions associated with (e.g., sensed from and/or the like) the plurality of ECG electrodes of the heart monitoring device 102 in the historical collection of the plurality of ECG signal portions with known rhythm change information to train the rhythm change classifier for the ECG signal(s) received form the plurality of ECG electrodes of the heart monitoring device 302a, as described herein. Additionally or alternatively, there may be sufficient data (e.g., historical ECG signal portions and/or the like) associated with (e.g., sensed from and/or the like) a second plurality of ECG electrodes (e.g., electrodes from an ECG device separate from the heart monitoring device 102, such as a 12-lead ECG sensor, a separate external and/or wearable heart monitoring device, and/or the like) independent of the plurality of ECG electrodes of the heart monitoring device 102 to train the rhythm change classifier based on the second plurality of ECG electrodes, as described herein. In some embodiments, the rhythm change classifier may be trained based on the ECG signal portion(s) associated with (e.g., sensed from and/or the like) the second plurality of ECG electrodes, as described herein. Additionally or alternatively, the rhythm change classifier may then be adapted to detect the predetermined rhythm change(s) based on the plurality of ECG electrodes of heart monitoring device 102, as described herein. In some embodiments, heart monitoring device 102 and/or gateway device 129 may determine (e.g., calculate and/or the like) a transform (e.g., vector projection and/or the like) of the ECG signal portion(s) associated with the second plurality of ECG electrodes to the plurality of ECG electrodes of heart monitoring device 102, and the transform of the ECG signal portion(s) may be used to train the rhythm change classifier as if the ECG signal portions were associated with (e.g., sensed from and/or the like) the plurality of ECG electrodes of the heart monitoring device 102, as described herein.

As shown in FIG. 4B, at step 406b, at least one ECG signal may be received, as described herein. For example, heart monitoring device 102 and/or gateway device 129 (e.g., the processor(s) thereof) may be configured to receive the ECG signal(s). In some embodiments, heart monitoring device 102 may be configured to receive the ECG signal(s) via the ECG channel(s), as described herein. Additionally or alternatively, heart monitoring device 102 may be configured to communicate (e.g., transmit) the ECG signal(s) to gateway device 129, and/or gateway device 129 may receive the ECG signals from heart monitoring device 102, as described herein.

As shown in FIG. 4B, at step 408b, at least one of predetermined rhythm change and/or a time thereof may be detected. For example, heart monitoring device 102 and/or gateway device 129 (e.g., the processor(s) thereof) may detect, with the rhythm change classifier, time data corresponding to a predetermined rhythm change in the at least one ECG signal, as described herein. Additionally or alternatively, heart monitoring device 102 and/or gateway device 129 (e.g., the processor(s) thereof) may detect, with the rhythm change classifier, the predetermined rhythm change based on the at least one ECG signal, as described herein.

In some embodiments, heart monitoring device 102 and/or gateway device 129 (e.g., processor(s) thereof) may detect (e.g., with the trained rhythm change classifier) the predetermined rhythm change based on the at least one ECG signal. In some embodiments, heart monitoring device 102 may further include at least one sensor and associated sensor circuitry configured to sense non-ECG biometric data of the patient (which, in some embodiments, may be communicated to gateway device 129), as described herein.

Additionally or alternatively, detecting the predetermined rhythm change may be further based on the non-ECG biometric data of the patient (e.g., non-ECG biometric data of the patient may be input into the neural network(s) of the rhythm change classifier, may be combined with the output of the rhythm change classifier, and/or the like), as described herein In some embodiments, detecting the predetermined rhythm change may be further based on at least one baseline ECG signal portion of the patient, as described herein.

In some embodiments, detecting the predetermined rhythm change may be further based on at least one calibration measurement of the patient, as described herein.

In some embodiments, detecting the predetermined rhythm change may be further based on at least one reference vector of the patient, as described herein.

In some embodiments, detecting the predetermined rhythm change may be further based on at least one previous ECG signal portion, as described herein.

In some embodiments, the heart monitoring device 102 and/or gateway device 129 (e.g., processor(s) thereof) may further determine (e.g., with the rhythm change classifier) a confidence score associated with the predetermined rhythm change based on the at least one ECG signal, as described herein.

As shown in FIG. 4B, at 410b, at least one ECG signal portion may be determined (e.g., based on the detected time data, the detected predetermined rhythm change, and/or the like. For example, heart monitoring device 102 and/or gateway device 129 (e.g., the processor(s) thereof) may determine (e.g., based on the detected time data) at least one ECG signal portion associated with the detected time data corresponding to the predetermined rhythm change in the ECG signal(s), as described herein.

As shown in FIG. 4B, at step 412b, the ECG signal portion(s) may be transmitted. For example, heart monitoring device 102 and/or gateway device 129 may communicate (e.g., transmit and/or the like) the determined ECG signal portion(s) to remote computer system 104, as described herein. Additionally or alternatively, heart monitoring device 102 and/or gateway device 129 (e.g., the processor(s) thereof) may communicate an indication (e.g., a flag, an indicator, a confidence score, a mark, metadata, the time data, and/or the like) associated with the predetermined rhythm change detected (e.g., identified and/or the like) in the ECG signal portion(s).

In some embodiments, heart monitoring device 102 and/or gateway device 129 (e.g., the processor(s) thereof) may further communicate (e.g., transmit and/or the like) at least one second ECG signal portion of the ECG signal(s) to remote computer system 104, as described herein. Additionally or alternatively, the second ECG signal portion(s) may be independent of the detected time data corresponding to the predetermined rhythm change in the ECG signal(s), as described herein.

In some embodiments, gateway device 129 may enable communication between heart monitoring device 102 and remote computer system 104, as described herein.

In some embodiments, remote computing system 104 may receive the determined ECG signal portion(s) (e.g., from heart monitoring device 102 and/or gateway device 129).

As shown in FIG. 4B, at step 414b, the second ECG signal portion(s) and/or annotation data associated with at least one annotation for the second ECG signal portion(s) may be received, as described herein. For example, heart monitoring device 102 and/or gateway device 129 may receive the second ECG signal portion(s) and/or annotation data associated with at least one annotation for the second ECG signal portion(s) from remote computer system 104, as described herein.

In some embodiments, remote computing system 104 may analyze the determined ECG signal portion(s) to classify a type of arrhythmia for the rhythm change(s) in the ECG signal(s), as described herein. For example, remote computer system 204a may include an arrhythmia type classifier (e.g., including at least one (second) neural network trained based on a (second) historical collection of a (second) plurality of ECG signal portions with known arrhythmia type information), as described herein.

In some embodiments, remote computer system 104 may communicate (e.g., transmit and/or the like) at least one message associated with the determined ECG signal portion(s) and/or the type of arrhythmia associated with the rhythm change, as described herein. For example, the message(s) may be communicated from remote computer system 104 to technician device 108, as described herein.

In some embodiments, remote computer system 104 may transmit at least one message associated with the second ECG signal portion(s) (e.g., randomly determined second ECG signal portion(s), second ECG signal portion(s) determined to have a confidence score below a first threshold and above a second threshold, and/or the like, as described herein) to technician device 108, as described herein.

In some embodiments, technician device 108 may receive at least one annotation associated with the ECG signal portion(s), e.g., via input from a user (e.g., a technician and/or the like). Additionally or alternatively, remote computer system 104 may receive annotation data associated with the annotation(s) from technician device 108, as described herein.

In some embodiments, remote computer system 104 may communicate the second ECG signal portion(s) and/or annotation data associated with at least one annotation for the second ECG signal portion(s) to heart monitoring device 102 and/or gateway device 129, as described herein.

As shown in FIG. 4B, at step 416b, the rhythm change classifier may be retrained. For example, heart monitoring device 102 and/or gateway device 129 may retrain the rhythm change classifier (and/or train an updated rhythm change classifier) based on the historical collection of the plurality of ECG signal portions with the known rhythm change information, the second ECG signal portion(s), and the annotation data associated therewith, as described herein.

In some non-limiting embodiments, process 400b may include repeating at least some steps (e.g., steps 406b-412b, 406b-416b, and/or the like). For example, at least some such steps may be repeated continuously, periodically, and/or the like. For example, ECG signal(s) may be received (406b) continuously. Additionally or alternatively, received ECG signals may be analyzed using the rhythm change classifier continuously. For example, predetermined rhythm changes and/or time data associated therewith may be detected (408b) as often as rhythm changes occur in the ECG signal(s). Additionally or alternatively, the ECG signal portion(s) may be determined (410b) and/or transmitted (412b) as often as rhythm changes and/or time data associated therewith may be detected. For example, the annotation(s) (and/or ECG signal portion(s) associated therewith) may be received (414b) and/or the rhythm change classifier may be retrained (416b) periodically, continuously, and/or the like.

Figure 4C:
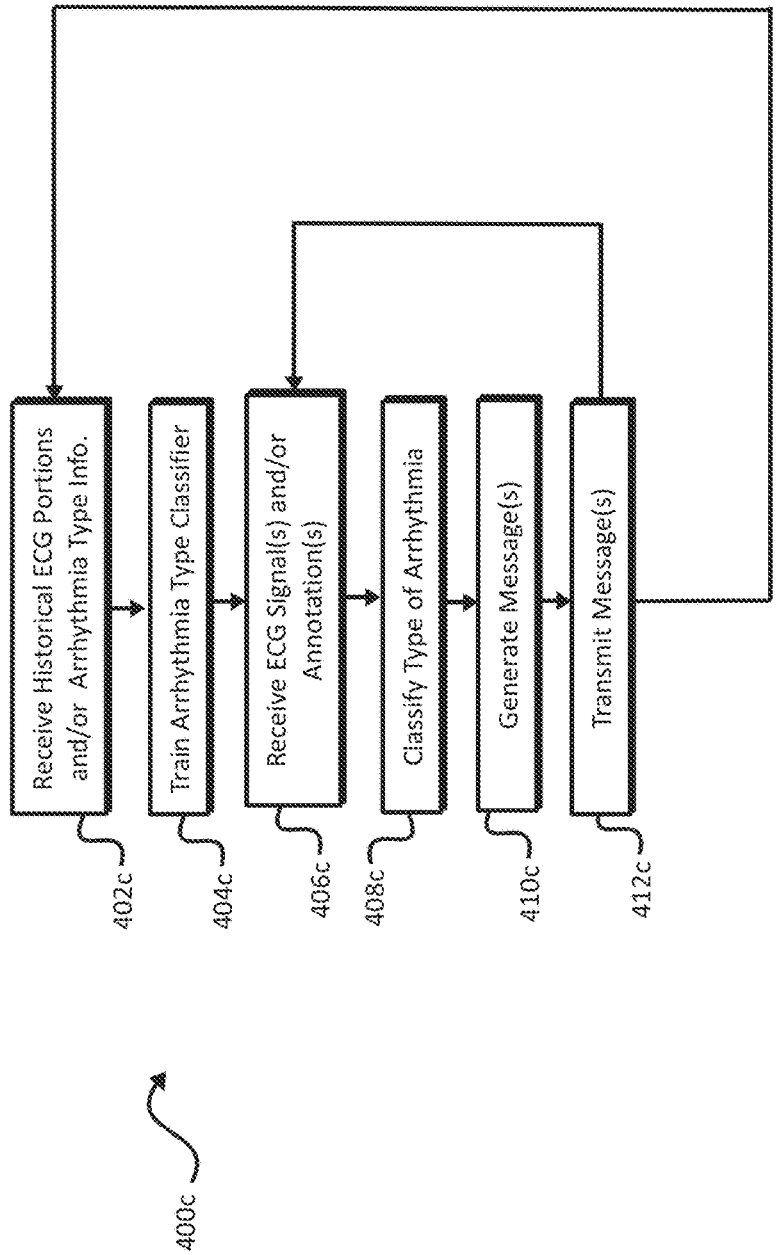

Referring now to FIG. 4C, FIG. 4C shows an example flow chart of a process 400c for arrhythmia monitoring, according to some embodiments. In some embodiments, one or more of the steps of process 400c may be performed (e.g., completely, partially, and/or the like) by remote server 104. In some non-limiting embodiments, one or more of the steps of process 400c may be performed (e.g., completely, partially, and/or the like) by another system, another device, another group of systems, or another group of devices, separate from or including remote server 104, such as heart monitoring device 102, data repository 106, technician device 108, gateway 129, and/or the like.

As shown in FIG. 4C, at step 402*a*, a historical collection of a plurality of ECG signal portions and information related thereto (e.g., known arrhythmia type information and/or the like) may be received. For example, remote computer system 104 may receive (e.g., retrieve, search for, send a request and/or query to cause data repository 106 to communicate, and/or the like) a historical collection of a plurality of ECG signal portions and information related thereto (e.g., known arrhythmia type information and/or the like), e.g., from data repository 106, as described herein.

As shown in FIG. 4C, at step 404*c*, an arrhythmia type classifier may be trained, as described herein. For example, remote computer system 104 may train at least one neural network of at least one classifier (e.g., an arrhythmia type classifier and/or the like) based on the historical collection of a plurality of ECG signal portions and information related thereto (e.g., known arrhythmia type information and/or the like), as described herein.

In some embodiments, an arrhythmia type classifier may include at least one neural network (e.g., at least one second neural network), as described herein. Additionally or alternatively, the at least one (second) neural network may include at least one of a deep neural network, a convolutional neural network, a recurrent neural network, an attention network, a fully connected neural network, any combination thereof, and/or the like, as described herein. In some embodiments, the neural network(s) may include a plurality of Siamese branches (e.g., each respective Siamese branch associated with a respective ECG channel), as described herein.

In some embodiments, remote computer system 104 may train an arrhythmia type classifier by predicting, with the arrhythmia type classifier, a predicted type of arrhythmia in each respective ECG signal portion of the historical collection of the plurality of ECG signal portions (or a second plurality thereof), determining at least one error value based on the predicted type of arrhythmia and the known arrhythmia type information (e.g., a respective annotations associated with a known type of arrhythmia for each respective ECG signal portion), and training the arrhythmia type classifier (e.g., updating the weights thereof and/or the like) based on the error value(s) (e.g., using back propagation and/or the like), as described herein. In some embodiments, the error value(s) may include one of a prediction error or a contrastive loss, as described herein.

In some embodiments, the known arrhythmia type information may include a plurality of annotations, as described herein. For example, each annotation may be associated with a respective ECG signal portion of the plurality of ECG signal portions, as described herein. In some embodiments, remote computer system 104 may train the arrhythmia type classifier based on the plurality of ECG signals and the plurality of annotations, as described herein.

In some embodiments, the plurality of annotations may be from a plurality of technicians (e.g., a plurality of technician devices 108 and/or the like), as described herein. Additionally or alternatively, each annotation annotations may be associated with a respective technician of the plurality of technicians and/or a respective ECG signal portion of the plurality of ECG signal portions, as described herein. In some embodiments, the arrhythmia type classifier may be trained separately for each technician, as described herein. For example, for a first technician of the plurality of technicians, the arrhythmia type classifier may be trained (e.g., by remote computer system 104) based on a subset of the plurality of ECG signals and the plurality of annotations associated with at least one other technician of the plurality of technicians different than the first technician, as described herein.

In some embodiments, each annotation may be associated with one possible type of arrhythmia (e.g., a label associated with a possible type of arrhythmia, a text string identifying at least one possible type arrhythmia, and/or the like) of the respective ECG signal(s) and/or portion(s) thereof, as described herein.

In some embodiments, there may be an insufficient number of ECG signal portions associated with (e.g., sensed from and/or the like) at least one second ECG electrode in the historical collection of the plurality of ECG signal portions with known arrhythmia type information (e.g., annotations, labels, and/or the like) to train the arrhythmia type classifier for the ECG signal(s) received from the second ECG electrode(s), as described herein. Additionally or alternatively, there may be sufficient data (e.g., historical ECG signal portions and/or the like) associated with (e.g., sensed from and/or the like) at least one first ECG electrode (e.g., electrodes from an ECG device separate from the second ECG electrode(s), such as a 12-lead ECG sensor, a separate external and/or wearable heart monitoring device, and/or the like) independent of the second ECG electrode(s) to train the rhythm change classifier based on the second ECG electrode(s), as described herein. In some embodiments, the known arrhythmia type information may include a plurality of annotations, each of which may be associated with a respective ECG signal portion of a first plurality of ECG signal portions associated with the first ECG electrode(s), as described herein. In some embodiments, each respective ECG signal portion of a second plurality of ECG signal portions associated with the second ECG electrode(s) may correspond to a respective ECG signal portion of the first plurality of ECG signal portions, as described herein. In some embodiments, remote computer system 104 may train the arrhythmia type classifier by predicting, with the arrhythmia type classifier, a predicted type of arrhythmia in each respective ECG signal portion of the second plurality of ECG signal portions, determining at least one error value based on the predicted type of arrhythmia and the respective annotation of the plurality of annotations associated with a respective ECG signal portion of the first plurality of ECG signal portions corresponding to the respective ECG signal portion of the second plurality of ECG signal portions, and training (e.g., updating the weights of and/or the like) the arrhythmia type classifier based on the at least one error value (e.g., based on back propagation and/or the like), as described herein.

In some embodiments, ECG signal portions associated with multiple electrodes may be combined (e.g., by vector addition, vector projection, a transform, and/or the like) to form extrapolated ECG signal portions that may be more familiar and/or suitable for review by a human user (e.g., technician and/or the like), as described herein. For example, the historical collection of the plurality of ECG signal portions may include a first plurality of ECG signal portions of at least one first ECG signal based on first surface ECG activity sensed by at least one first ECG electrode and a second plurality of ECG signal portions of at least one second ECG signal based on second surface ECG activity sensed by at least one second ECG electrode, as described herein. In some embodiments, each ECG signal portion of the first plurality of ECG signal portions may be combined (e.g., by vector addition, vector projection, a transform, and/or the like) with a respective ECG signal portion of the second plurality of ECG signal portions to form a plurality of extrapolated ECG signal portions (e.g., by remote computer system 104), as described herein. In some embodiments, the known arrhythmia type information may include a plurality of annotations, as described herein. Additionally or alternatively, each respective annotation may be associated with a respective extrapolated ECG signal portion of the plurality of extrapolated ECG signal portions, as described herein.

In some embodiments, at least some of the plurality of ECG signal portions of the historical collection may be time warped (e.g., time dilated and/or the like) to form a plurality of warped ECG signal portions (e.g., by remote computer system 104 using any suitable signal processing technique for time warping, time dilation, and/or the like), as described herein.

In some embodiments, at least some of the plurality of ECG signal portions of the historical collection may be at least one of filtered, inverted, any combination thereof, and/or the like (e.g., by remote computer system 104), as described herein.

In some embodiments, at least one noise signal portion may be combined with at least some of the plurality of ECG signal portions of the historical collection (e.g., by remote computer system 104), as described herein.

In some embodiments, at least some of the plurality of ECG signal portions of the historical collection may be style transferred (e.g., by remote computer system 104), as described herein.

As shown in FIG. 4C, at step 406c, at least one ECG signal and annotation data associated with at least one annotation for each ECG signal may be received. For example remote computer system 104 may receive at least one ECG signal and annotation data associated with at least one annotation for each ECG signal (e.g., from technician device 108), as described herein.

As shown in FIG. 4C, at step 408c, a type of arrhythmia may be detected (e.g., classified), as described herein. For example, remote computer system 104 may detect, with the arrhythmia type classifier, a type of arrhythmia in the ECG signal(s) and time data associated with the detected type of arrhythmia, as described herein. For example, the time data may include at least one of a start time, a time interval, any combination thereof, and/or the like, as described herein. In some embodiments, remote computer system 104 may determine, based on the time data, at least one ECG signal portion associated with the detected type of arrhythmia in the ECG signal(s), as described herein.

In some embodiments, remote computer system 104 may determine a plausibility score for the annotation(s) based on the detected type of arrhythmia. For example, an output of at least one neural network of the arrhythmia type classifier may include a confidence score (e.g., a probability and/or the like) associated with each possible type of arrhythmia, as described herein. For example, the type of arrhythmia determined by the arrhythmia type classifier may be the type of arrhythmia with a highest confidence score (e.g., probability and/or the like). Additionally or alternatively, each annotation may be associated with one possible type of arrhythmia (e.g., a label associated with a possible type of arrhythmia, a text string identifying at least one possible type arrhythmia, and/or the like). In some embodiments, plausibility score of each annotation may be the confidence score (e.g., determined by the arrhythmia type classifier) of the possible type of arrhythmia associated with such annotation. In some embodiments, the arrhythmia type classifier may include a plurality of neural networks, and each such neural network may output a confidence score associated with at least one possible type of arrhythmia.

As shown in FIG. 4C, at step 410c, at least one message may be generated (e.g., based on the determined ECG signal portion, the plausibility score, and/or the like). For example, remote computer system 104 may generate at least one message based on the at least one determined ECG signal portion and the plausibility score for the at least one annotation, as described herein. For example, the message(s) may indicate at least one of a recommendation to annotate the at least one determined ECG signal portion based on the detected type of arrhythmia, a recommendation to reevaluate the annotation data associated with the at least one determined ECG signal portion based on the plausibility score, and/or the like.

In some embodiments, remote computer system 104 may to determine the plausibility score is below a threshold. Additionally or alternatively, generating the message(s) may include remote computer system 104 generating, based on the determination that the plausibility score is below the threshold, the at least one message indicating the recommendation to reevaluate the annotation data associated with the at least one determined ECG signal portion, as described herein.

As shown in FIG. 4C, at step 412c, the message(s) may be transmitted. For example, remote computer system 104 may transmit at least some of the message(s) associated with the at least one determined ECG signal portion to technician device 108, as described herein. Additionally or alternatively, remote computer system 104 may transmit at least some of the message(s) associated with the at least one determined ECG signal portion to supervisor device 110, as described herein.

In some non-limiting embodiments, process 400c may include repeating at least some steps (e.g., steps 406c-412c, 402c-412c, and/or the like). For example, at least some such steps may be repeated continuously, periodically, and/or the like. For example, ECG signal(s) and/or annotation(s) associated therewith may be received (406c) continuously, as often as the technician(s) provide such annotation(s), periodically and/or the like. Additionally or alternatively, the type of arrhythmia may be classified (408c) and/or the message(s) may be generated (410c) and/or transmitted (412c) continuously, as often as ECG signal(s) and/or annotation(s) are received, periodically, and/or the like. For example, the historical collection of ECG signal portions may be updated (e.g., new ECG signal portion(s) and/or known arrhythmia type information may be added and/or the like) continuously, periodically, and/or the like. Additionally or alternatively, the arrhythmia type classifier may be (re-) trained (404c) continuously, as often as the historical collection of ECG signal portions is updated, periodically and/or the like.

Figure 5A:
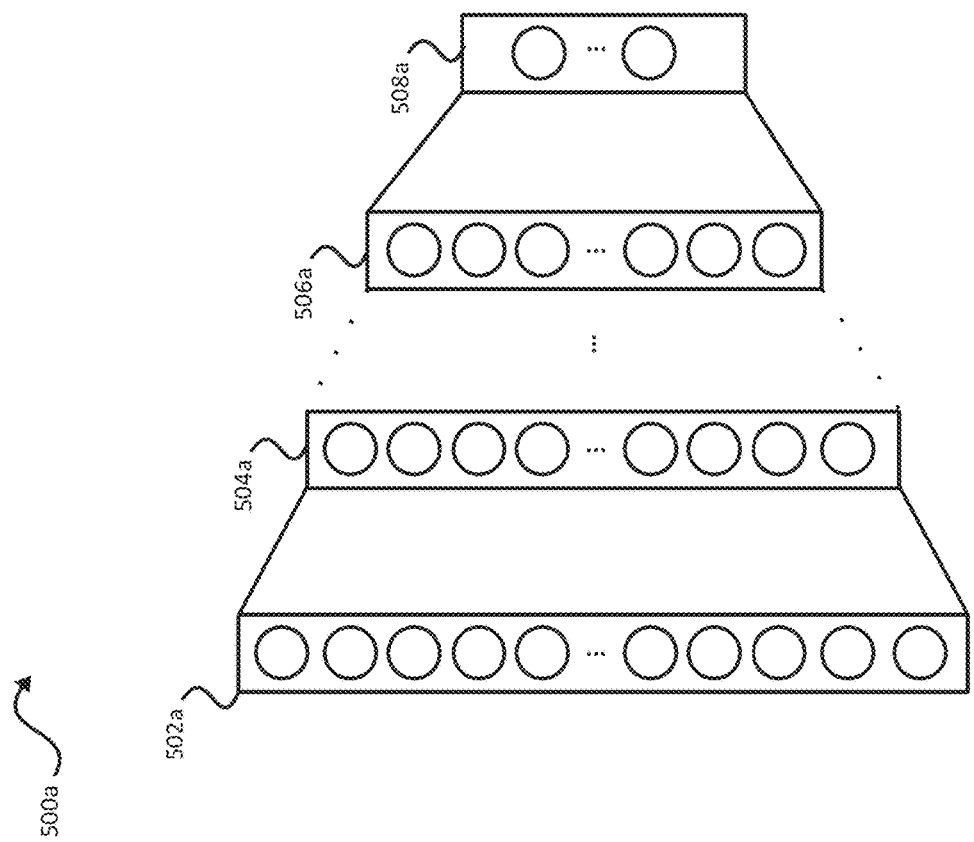
FIG. 5A shows an example diagram of a neural network of an exemplary rhythm change classifier, according to some embodiments.

Referring now to FIG. 5A, FIG. 5A shows an example diagram of a neural network 500a of an exemplary rhythm change classifier. As shown in FIG. 5A, neural network 500a may include at least one input layer 502a, as described herein. Additionally or alternatively, neural network 500a may include at least one output layer 508a, as described herein. In some embodiments, neural network 500a may include at least one hidden layer (e.g., first hidden layer 504a, last hidden layer 506a, and/or the like), as described herein. In some embodiments, the hidden layer(s) (e.g., first hidden layer 504a, last hidden layer 506a, and/or the like) may include a plurality of convolutional layers, as described herein.

Figure 5B:
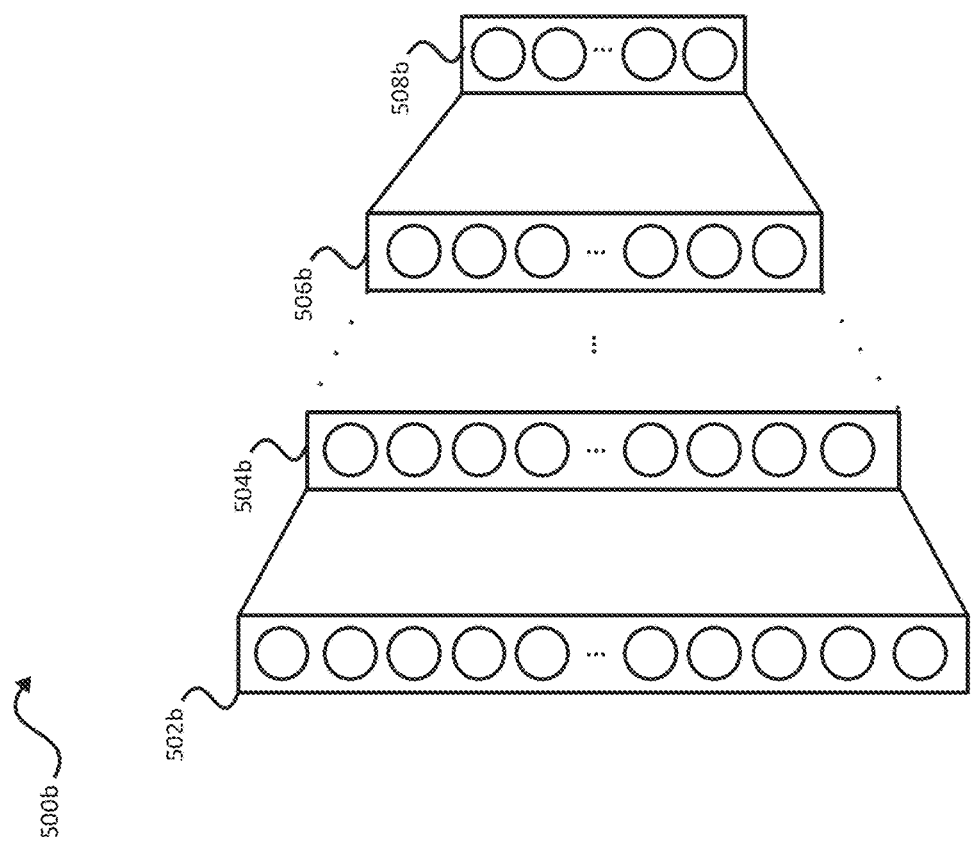
FIG. 5B shows an example diagram of a neural network of an arrhythmia type classifier, according to some embodiments.

Referring now to FIG. 5B, FIG. 5B shows an example diagram of a neural network 500b of an exemplary arrhythmia type classifier. As shown in FIG. 5B, neural network 500b may include at least one input layer 502b, as described herein. Additionally or alternatively, neural network 500b may include at least one output layer 508b, as described herein. In some embodiments, neural network 500b may include at least one hidden layer (e.g., first hidden layer 504b, last hidden layer 506b, and/or the like), as described herein. In some embodiments, the hidden layer(s) (e.g., first hidden layer 504b, last hidden layer 506b, and/or the like) may include a plurality of convolutional layers, as described herein.

Figure 6A:
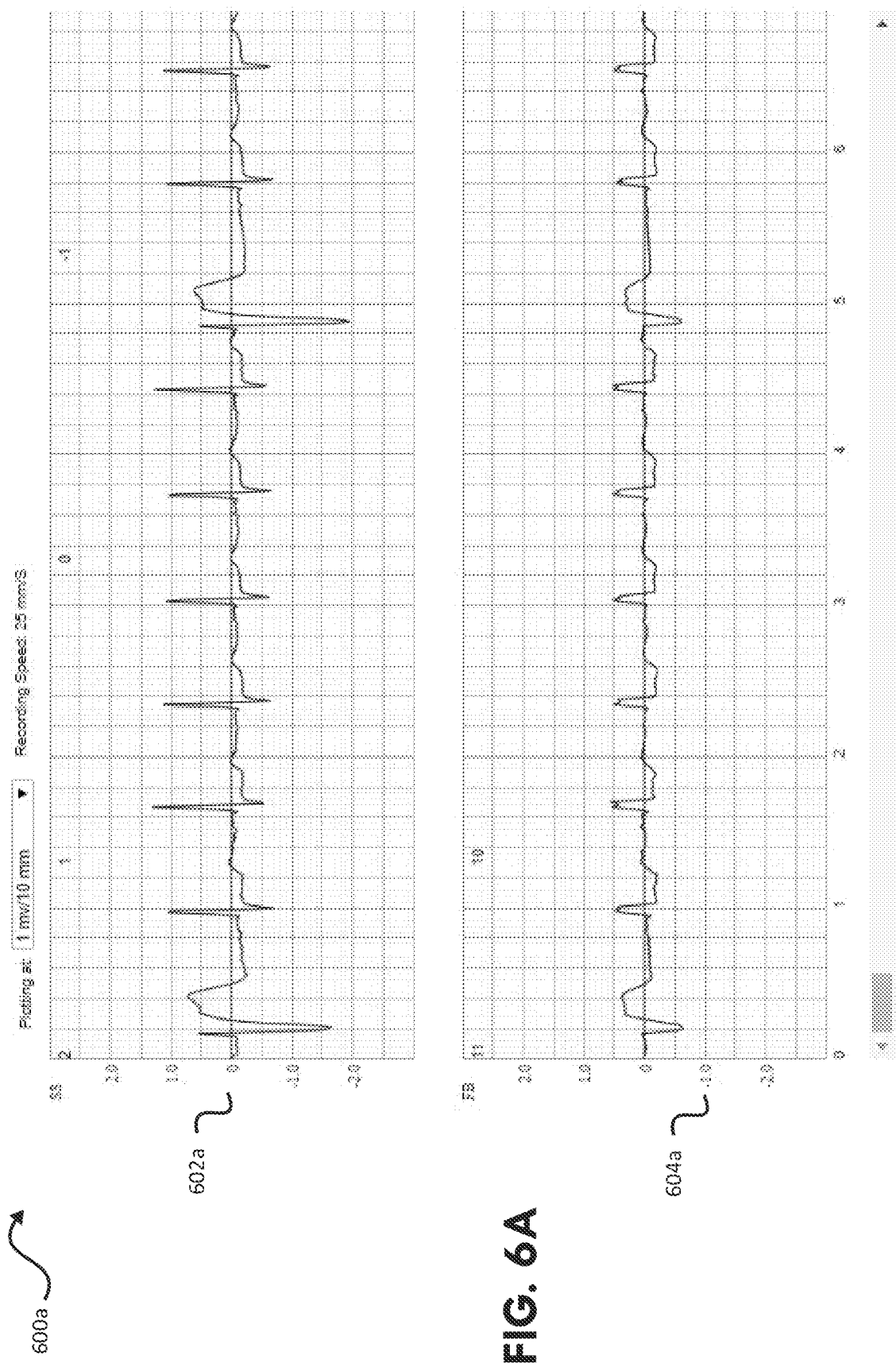
FIGS. 6A-E show example ECG signal portions, according to some embodiments.

Referring now to FIGS. 6A-E, FIGS. 6A-E show example ECG signal portions. As shown in FIG. 6A, first ECG signal portion 600a may include portions of first ECG signal from a first channel 602a and second ECG signal from a second channel 604a. In some embodiments, first ECG signal portion 600a may show normal sinus rhythm (NSR) on both channels.

Figure 6B:
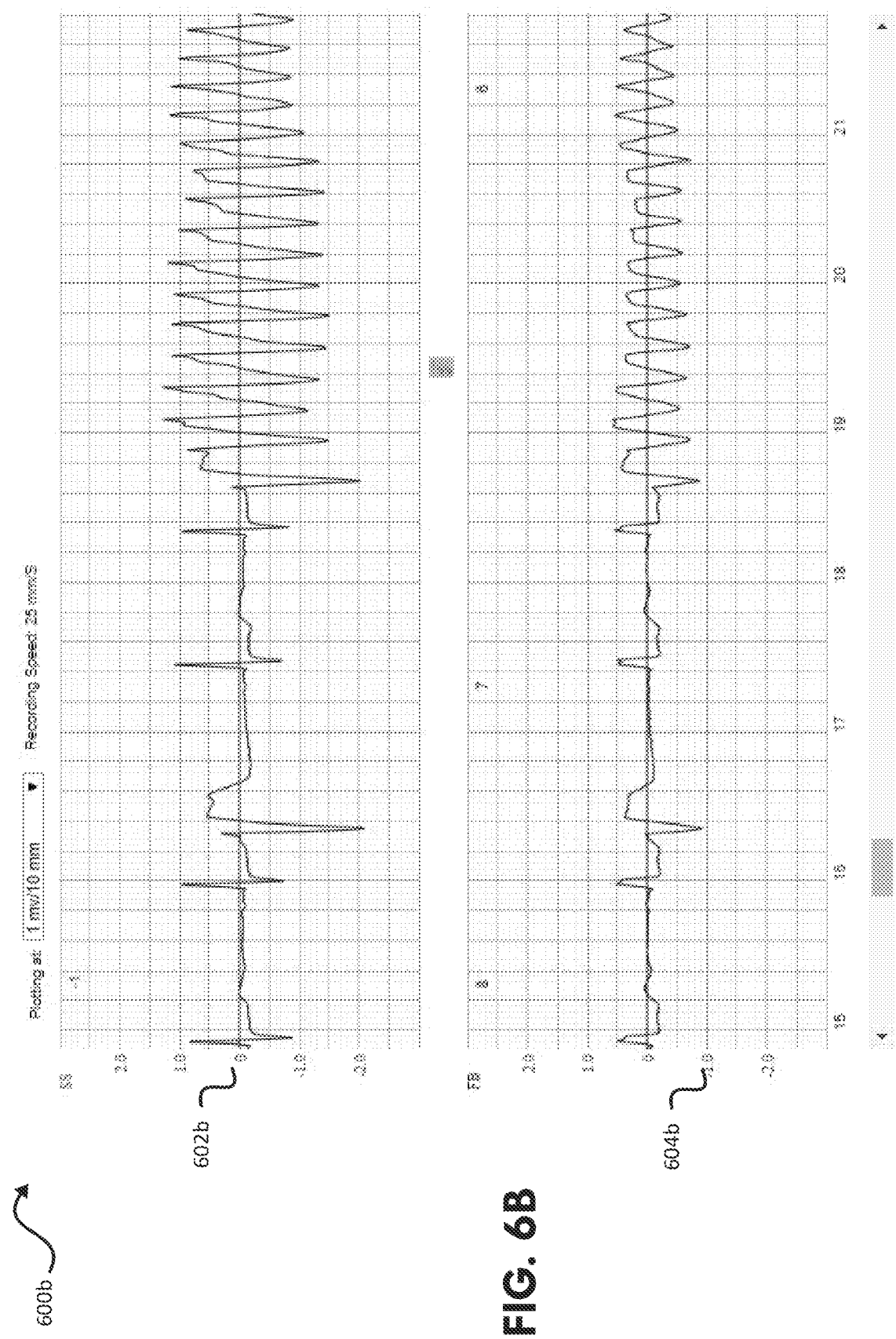

As shown in FIG. 6B, second ECG signal portion 600b may include portions of first ECG signal from a first channel 602b and second ECG signal from a second channel 604b. In some embodiments, second ECG signal portion 600b may show a rhythm change between 18 and 19 seconds on both channels.

Figure 6C:
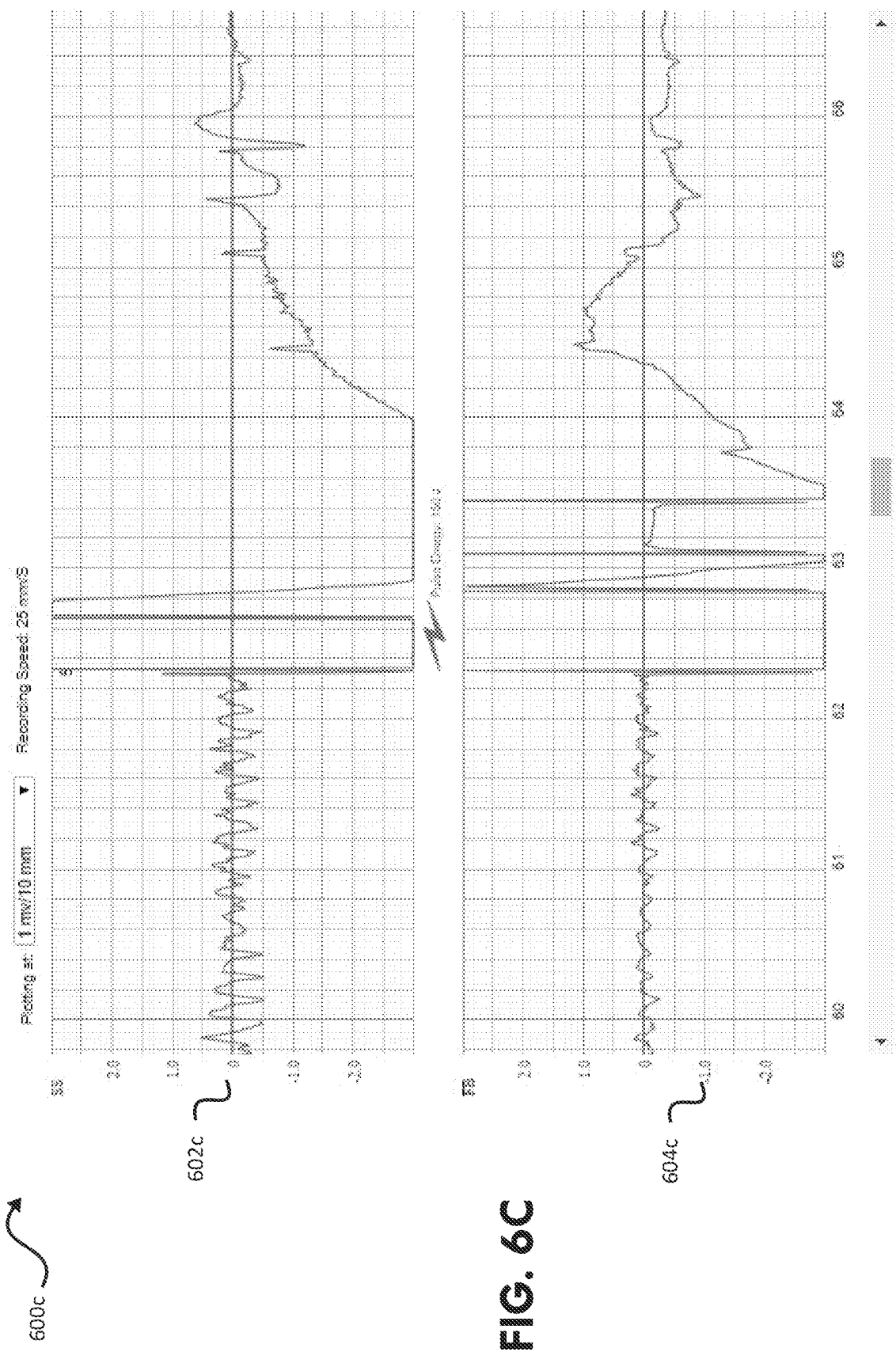

As shown in FIG. 6C, third ECG signal portion 600c may include portions of first ECG signal from a first channel 602c and second ECG signal from a second channel 604c. In some embodiments, third ECG signal portion 600c may show a therapeutic treatment (e.g., therapeutic shock of 150 J) between 62 and 63 seconds on both channels.

Figure 6D:
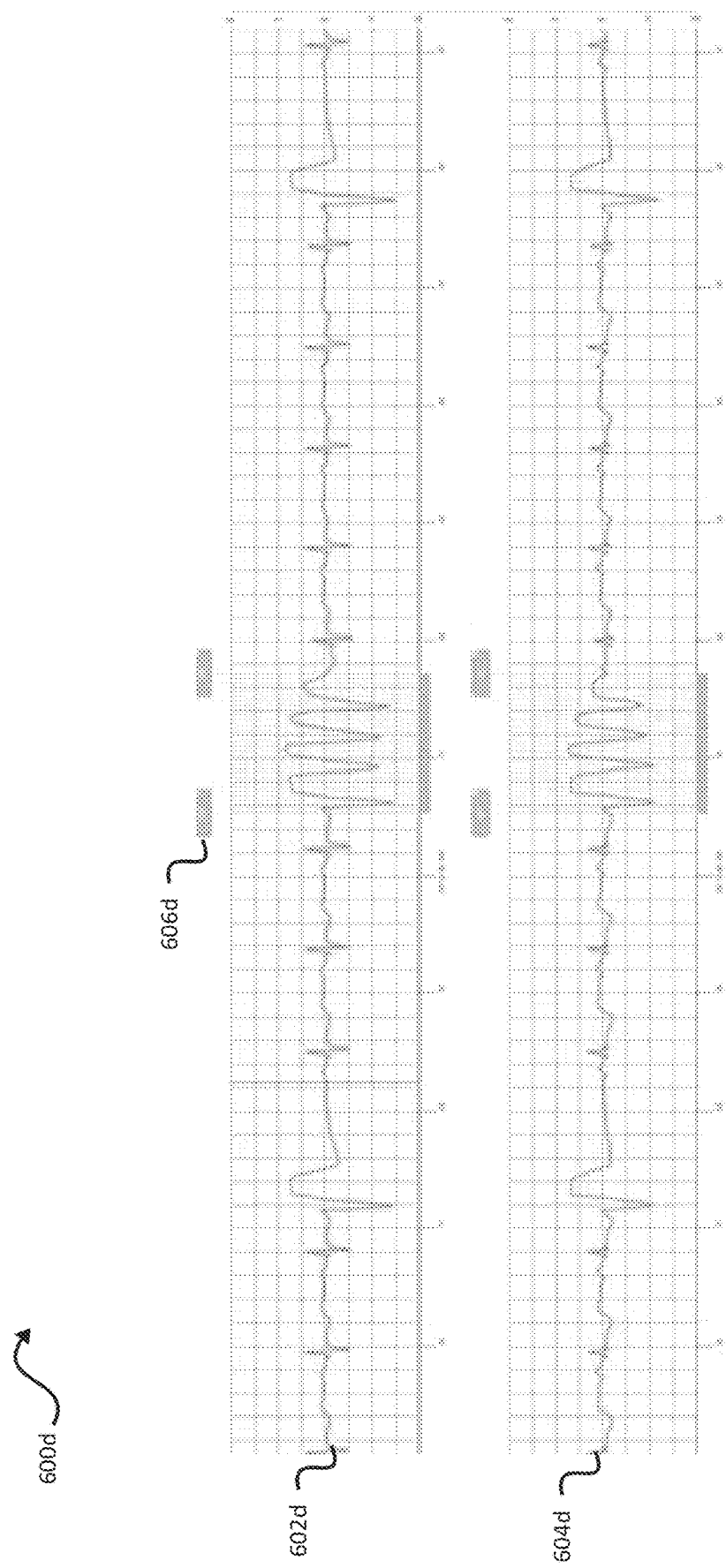

As shown in FIG. 6D, fourth ECG signal portion 600d may include portions of first ECG signal from a first channel 602d and second ECG signal from a second channel 604d. In some embodiments, fourth ECG signal portion 600d may show a rhythm change in the highlighted time period 606d on both channels.

Figure 6E:
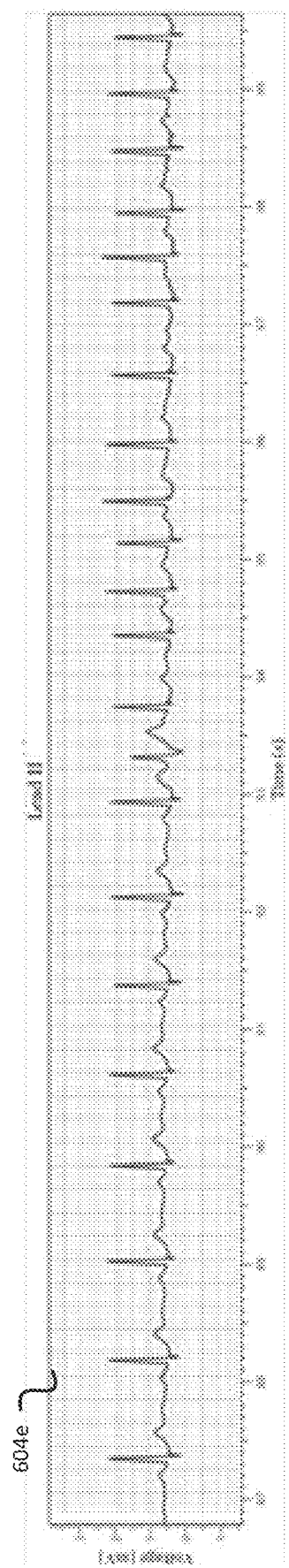

As shown in FIG. 6E, fifth ECG signal portion 600e may include a portion of an ECG signal from a channel 604e. In some embodiments, fifth ECG signal portion 600e may show a rhythm change between 93 and 94 seconds.

Figure 7:
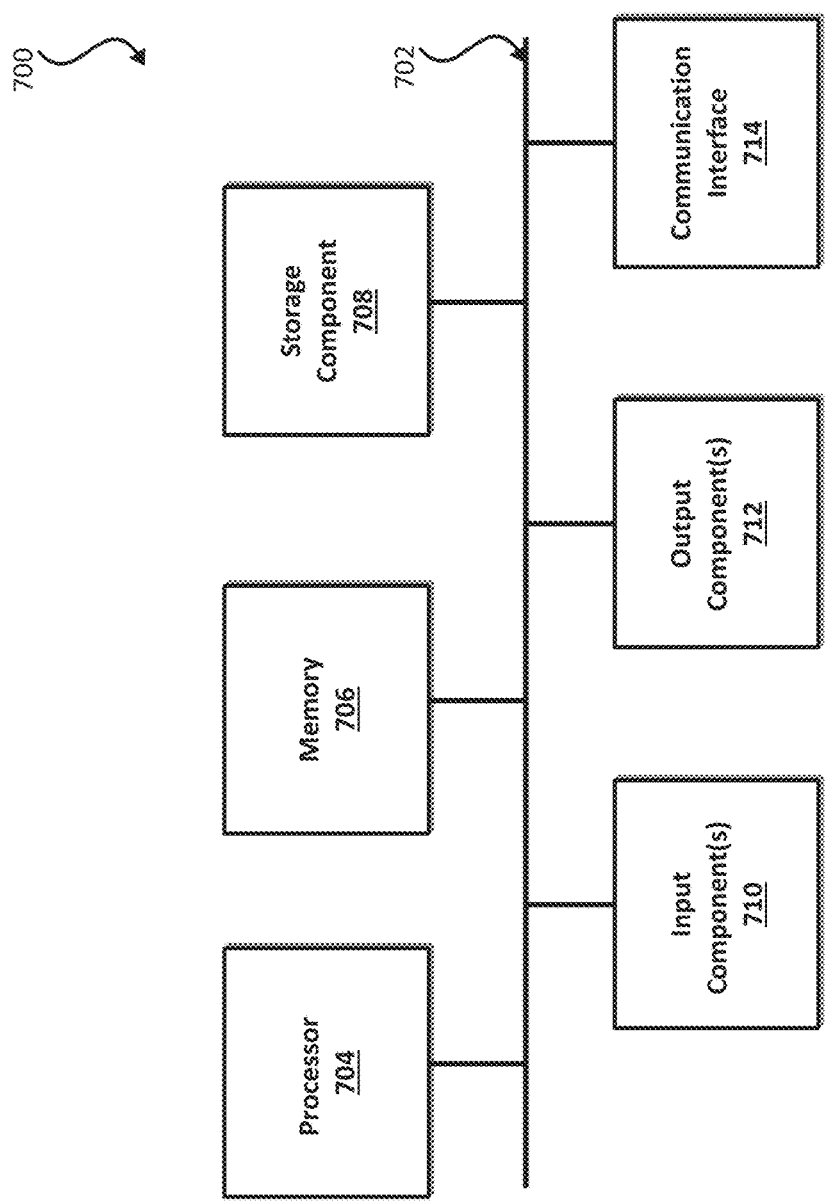
FIG. 7 shows an example block diagram of components of one or more computing devices on which the processes described herein can be implemented, according to some embodiments.

Referring now to FIG. 7, FIG. 7 is a diagram of example components of a device 700. Device 700 may correspond to one or more devices of heart monitoring device 102, remote computer system 104, data repository 106, technician device 108, supervisor device 110, and/or gateway device 129. In some non-limiting embodiments, heart monitoring device 102, remote computer system 104, data repository 106, technician device 108, supervisor device 110, and/or gateway device 129 may include at least one device 700 and/or at least one component of device 700. As shown in FIG. 7, device 700 may include bus 702, processor 704, memory 706, storage component 708, input component 710, output component 712, and communication interface 714.

Bus 702 may include a component that permits communication among the components of device 700. In some non-limiting embodiments, processor 704 may be implemented in hardware, firmware, or a combination of hardware and software. For example, processor 704 may include a processor (e.g., a central processing unit (CPU), a graphics processing unit (GPU), an accelerated processing unit (APU), and/or the like), a microprocessor, a digital signal processor (DSP), and/or any processing component (e.g., a field-programmable gate array (FPGA), an application-specific integrated circuit (ASIC), and/or the like), and/or the like, which can be programmed to perform a function. Memory 706 may include random access memory (RAM), read only memory (ROM), and/or another type of dynamic or static storage device (e.g., flash memory, magnetic memory, optical memory, and/or the like) that stores information and/or instructions for use by processor 704.

Storage component 708 may store information and/or software related to the operation and use of device 700. For example, storage component 708 may include a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, and/or another type of computer-readable medium, along with a corresponding drive.

Input component 710 may include a component that permits device 700 to receive information, such as via user input (e.g., a touch screen display, a keyboard, a keypad, a mouse, a button, a switch, a microphone, a camera, and/or the like). Additionally or alternatively, input component 710 may include a sensor for sensing information (e.g., a global positioning system (GPS) component, an accelerometer, a gyroscope, an actuator, and/or the like). Output component 712 may include a component that provides output information from device 700 (e.g., a display, a speaker, one or more light-emitting diodes (LEDs), and/or the like).

Communication interface 714 may include a transceiver-like component (e.g., a transceiver, a receiver and transmitter that are separate, and/or the like) that enables device 700 to communicate with other devices, such as via a wired connection, a wireless connection, or a combination of wired and wireless connections. Communication interface 714 may permit device 700 to receive information from another device and/or provide information to another device. For example, communication interface 714 may include an Ethernet interface, an optical interface, a coaxial interface, an infrared interface, a radio frequency (RF) interface, a universal serial bus (USB) interface, a Wi-Fi® interface, a Bluetooth® interface, a Zigbee® interface, a cellular network interface, and/or the like.

Device 700 may perform one or more processes described herein. Device 700 may perform these processes based on processor 704 executing software instructions stored by a computer-readable medium, such as memory 706 and/or storage component 708. A computer-readable medium (e.g., a non-transitory computer-readable medium) is defined herein as a non-transitory memory device. A non-transitory memory device includes memory space located inside of a single physical storage device or memory space spread across multiple physical storage devices.

Software instructions may be read into memory 706 and/or storage component 708 from another computer-readable medium or from another device via communication interface 714. When executed, software instructions stored in memory 706 and/or storage component 708 may cause processor 704 to perform one or more processes described herein. Additionally or alternatively, hardwired circuitry may be used in place of or in combination with software instructions to perform one or more processes described herein. Thus, embodiments described herein are not limited to any specific combination of hardware circuitry and software.

The number and arrangement of components shown in FIG. 7 are provided as an example. In some non-limiting embodiments, device 700 may include additional components, fewer components, different components, or differently arranged components than those shown in FIG. 7. Additionally or alternatively, a set of components (e.g., one or more components) of device 700 may perform one or more functions described as being performed by another set of components of device 700.

Figure 8:
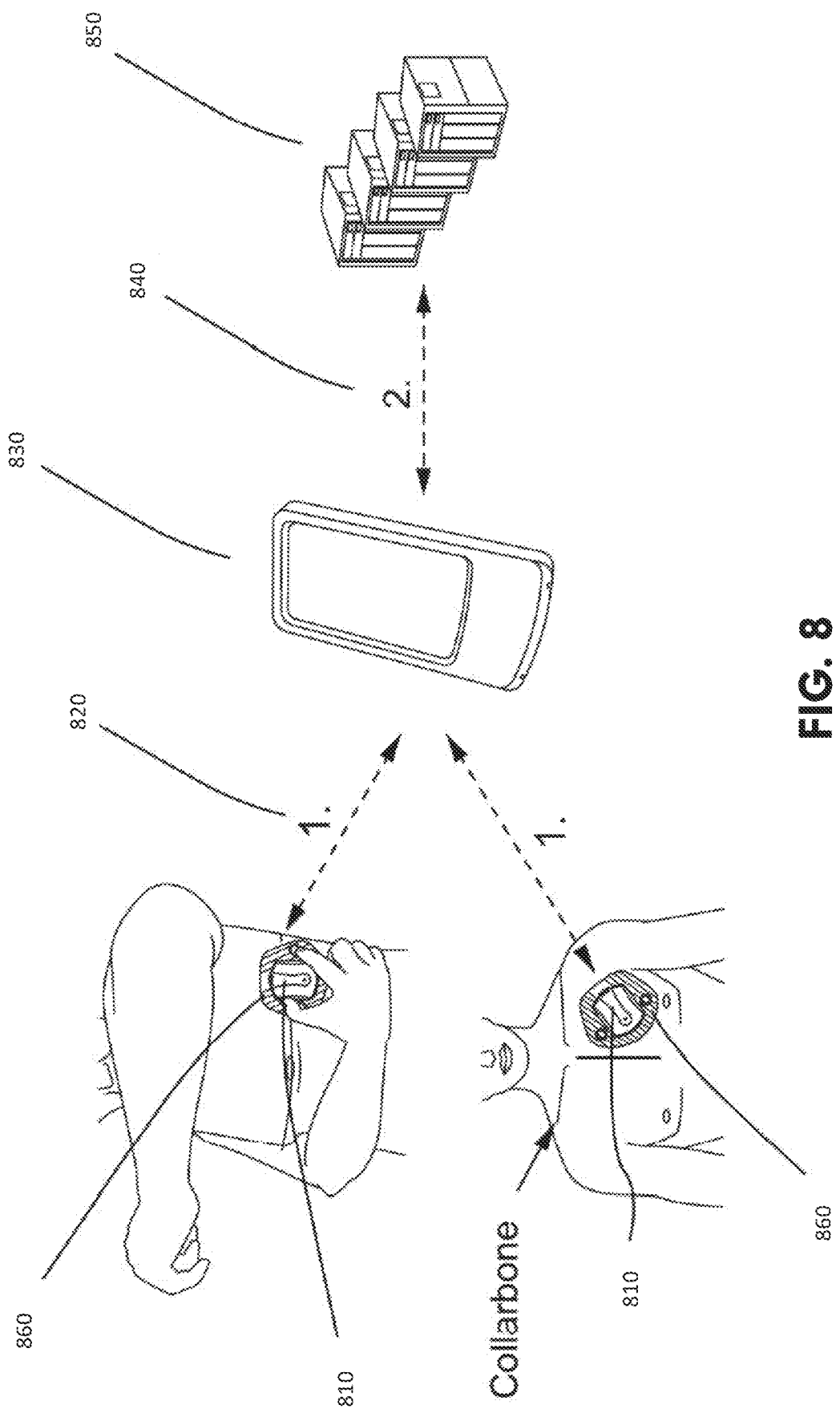
FIG. 8 shows an example schematic illustration of measurement and transmission of physiological data acquired via body-worn sensor(s) (e.g., external heart monitoring device(s)) disclosed herein, according to some embodiments.

Referring now to FIG. 8, FIG. 8 shows an exemplary heart monitoring device, e.g., an arrhythmia and fluid monitoring system that includes a physiological monitoring device 810, hereinafter referred to as "sensor(s)", and a wearable patch 860 configured to place the sensor(s) on, or in the vicinity of, a surface of a body (e.g., a patient). Further, the system may include a portable data transmission device (gateway) 830 that is capable of continuously transmitting data acquired by the sensor(s) 810 to a remote computer system (e.g., one or more servers 850) for processing and/or analysis. Thus, for example, the gateway device 830 may transmit to the server 850 data received from the sensor(s) 810 with little or no delay or latency. To this end, in the context of data transmission between the device(s) 810 and server(s) 850, "continuously" for the present disclosure includes continuous (without interruption), or near continuous, i.e., within one minute after completion of a measurement by and/or an occurrence of an event on the device. Continuity may also be achieved by repetitive successive bursts of transmission, e.g., high-speed transmission. Similarly, the term "immediate," according to the present disclosure, includes as occurring or done at once, or near immediate i.e., within one minute after the completion of a measurement by and/or an occurrence of an event occurring on the device.

Further, in the context of physiological data acquisition by the device(s) 810, "continuously" also includes uninterrupted collection of sensor data, such as ECG data and/or accelerometer data, with clinical continuity. In this case, short interruptions in data acquisition of up to 1-second several times an hour or longer interruptions of a few minutes several times a day may be tolerated and can still be seen as "continuous". As to latency as a result of such a continuous scheme as described herein, this relates to the overall budget of response time which can amount to between about 5 to about 15 minutes overall response time (e.g., time from when an event onset is detected to when a notification regarding the event is issued). As such, transmission/acquisition latency would therefore be in the order of minutes.

Further, the wearable devices described herein are configured for long-term and/or extended use or wear by, or attachment or connection to a patient. For example, devices as described herein may be capable of being used or worn by, or attached or connected to a patient, without substantial interruption, for example, up to 24 hours or beyond (e.g., weeks, months, or even years). In some implementations, such devices may be removed for a period of time before use, wear, attachment, or connection to the patient is resumed, e.g., to change batteries, carry out technical service, update the device software or firmware, and/or to take a shower or engage in other activities, without departing from the scope of the examples described herein.

In some embodiments, the transmission of data/signals 820 between the sensor(s) 810 and the gateway device 830 may be a one way (e.g., from the sensor(s) 810 to the gateway device 830) or the transmission may be bi-directional. Similarly, the transmission of data/signals 840 between the gateway device 830 and the server 850 may be one way (e.g., from the gateway device 830 to the server 850) or bi-directional. The system may also include a charger (not shown) for powering the electronics of the system.

In some embodiments, the sensor(s) 810 is configured to monitor, record and transmit to the gateway device 830 physiological data about the wearer of the sensor(s) 810 continuously. In particular, the sensor(s) 810 may not interrupt monitoring and/or recording additional data while transmitting already acquired data to the gateway device 830. Put another way, in some embodiments, both the monitoring/recording and the transmission processes occur at the same time or at least nearly at the same time.

As an another example, if the sensor(s) 810 does suspend monitoring and/or recording additional data while it is transmitting already acquired data to the gateway device 830, the sensor(s) 810 may then resume monitoring and/or recording additional data prior to all the already acquired data being transmitted to the gateway device 830. In other words, the interruption period for monitoring and/or recording may be less in comparison to the time it takes to transmit the already acquired data (e.g., between about 0% to about 80%, about 0% to about 60%, about 0% to about 40%, about 0% to about 20%, about 0% to about 10%, about 0% to about 5%, including values and subranges therebetween), facilitating the near-continuous monitoring and/or recording of additional data during transmission of already acquired physiological data. For example in one specific scenario, when a measurement time duration is around 2 minutes, any period of suspension or interruption in the monitoring and/or recording of subsequent measurement data may range from a just few milliseconds to about a minute. Example reasons for such suspension or interruption of data may include allowing for the completion of certain data integrity and/or other on-line tests of previously acquired data as described in further detail below. If the previous measurement data has problems, the sensor(s) 810 can notify the patient and/or remote technician of the problems so that appropriate adjustments can be made.

In some embodiments, the bandwidth of the link 820 between the sensor 810 and the gateway device 830 may be larger, and in some instances significantly larger, than the bandwidth of the acquired data to be transmitted via the link 820 (e.g., burst transmission). Such embodiments ameliorate issues that may arise during link interruptions, periods of reduced/absent reception, etc. In some embodiments, when transmission is resumed after interruption, the resumption may be in the form of last-in-first-out (LIFO). The gateway device 830 can be configured to operate in a store and forward mode where the data received from the sensor 810 is first stored in an onboard memory of the gateway device and then forwarded to the external server. For example, such a mode can be useful where the link with the server may be temporarily unavailable. In some embodiments, the gateway device 830 can function as a pipe line and pass through data from the sensor 810 immediately to the server. In further examples, the data from the sensor may be compressed using data compression techniques to reduce memory requirements as well as transmission times and power consumptions.

In some embodiments, the sensor(s) 810 may be configured to monitor, record and transmit some data in a continuous or near-continuous manner as discussed above, while monitoring, recording and transmitting some other data in a non-continuous manner (e.g., periodically, no-periodically, etc.). For example, the sensor(s) 810 may be configured to record and transmit ECG data continuously or nearly continuously while radio-frequency (RF) based measurements and/or transmissions may be periodic. For example, ECG data may be transmitted to the gateway device 830 (and subsequently the server 850) continuously or near-continuously as additional ECG data is being recorded, while RF-based measurements may be transmitted once the measuring process is completed.

Monitoring and/or recording of physiological data by the sensor(s) 810 may be periodic, and in some embodiments, may be accomplished as scheduled (i.e., periodically) without delay or latency during the transmission of already acquired data to the gateway device 830. For example, the sensor(s) 810 may acquire physiological data from the patient (i.e., the wearer of the sensor(s) 810) in a periodic manner and transmit the data to the gateway device 830 in a continuous manner as described above.

The sensor(s) 810 may be configured to transmit the acquired data to the servers 850 instead of, or in addition to, transmitting the data to the gateway device 830. The sensor(s) 810 may also be configured to store some or all of the acquired physiological data. In some embodiments, the transmission of data from the sensor(s) 810 to the gateway device 830 may be accomplished wirelessly (e.g., Bluetooth®, etc.) and/or via a wired connection, e.g., 820. The transmission of data from the gateway device 830 to the server 850 may also be accomplished wirelessly (e.g., Bluetooth®-to-TCP/IP access point communication, Wi-Fi®, cellular, etc.) and/or via a wired connection, e.g., 840.

As mentioned above, in some embodiments, the transmission of data and/or signals occurs via two links 820, 840, the links between the sensor(s) 810 and the gateway device 830 (e.g., Bluetooth® link) and between the gateway device 830 and the server 850 (e.g., Wifi®, cellular). The Bluetooth® link can be a connection bus for sensor(s) 810 and server 850 communication, used for passing commands, information on status of the microprocessor of the sensor(s) 810, measurement data, etc. In some embodiments, the microprocessor of the sensor(s) 810 may initiate communication with the server 850 (and/or the gateway device 830), and once connection is established, the server 850 may be configured to initiate some or all other communications. In some embodiments, the gateway device 830 may be configured to conserve the power available to the sensor(s) 810, device 830 and/or servers 850. For example, one or both links 820, 840 may enter power saving mode (e.g., sleep mode, off-state, etc.) when the connections between the respective devices/server are not available. As another example, the transmission of data may also be at least temporarily interrupted when the link quality (e.g., available bandwidth) is insufficient for at least a satisfactory transmission of the data. In such embodiments, the gateway device 830 may serve as a master device in its relationship to one or both of the sensor(s) 810 and the server 850.

In some embodiments, the gateway device 830 may be considered as a simple pipe, the sensor-gateway device-server path may be defined as a single link, i.e., the link performance may depend on the bottleneck between the sensor-gateway device and gateway device-server links. In some embodiments, at least the main bottleneck may be the gateway device-server link, since the gateway device is carried by the patient in close proximity to the device, while the gateway device-server link (e.g., cellular or WiFi® coverage) is expected to be variable. In some embodiments, a "best effort delivery" quality-of-service may be sufficient for the Bluetooth link and/or the TCP/IP link, since the transmitted data is processed (with some latency, for example) and is used for displaying notifications (for example, instead of being presented online to a monitoring center). In some embodiments, a single gateway device 830 may be configured to serve a plurality of sensors, i.e., the plurality of sensors may be connected to a single gateway device 830 via respective links. In some embodiments, there may be a plurality of gateway devices serving one or more sensor(s), i.e., each sensor of one or more sensors may be connected to a plurality of gateway devices via respective links.

In some embodiments, the transmission links 820, 840 may be configured to withstand co-existence interference from similar devices in the vicinity and from other devices using the same RF band (e.g., Bluetooth®, Cellular, WiFi®). Standard Bluetooth® protocol and/or standard TCP/IP protocols, as well as the addition of cyclic redundancy check to the transmitted data may be used to address any issue of interference. Further, to preserve the security of wireless signals and data, in some embodiments, data transfer between the sensor and the server may be done using a proprietary protocol. For example, TCP/IP link may use SSL protocol to maintain security, and the Bluetooth® link may be encrypted. As another example, UDP/HTTP may also be used for secure transmission of data. In some embodiments, only raw binary data may be sent, without any patient identification.

Examples of the types of physiological data that the arrhythmia and fluid monitoring sensor(s) 810 is configured to monitor and/or acquire from a patient wearing the sensor(s) 810 include one or more of electrocardiogram (ECG) data, thoracic impedance, heart rate, respiration rate, physical activity (e.g., movement) and patient posture. In some embodiments, the physiological data may be acquired and/or transmitted to the gateway device 830 or the server 850 by the sensor(s) 810 in a manner that is continuous, periodic or as instructed by received signals (e.g., as instructed by signal received from the gateway device 830 and/or the server 850). For example, the wearer of the sensor or another party (e.g., a health professional) may activate the sensor(s) 810 and the sensor may start monitoring and/or recording any one of the above-noted physiological parameters automatically without further input from the wearer or the party. The sensor(s) 810, or the arrhythmia and fluid monitoring system in general, may request further input (e.g., selection of a setting identifying the physiological parameter to be measured) before initiating the monitoring and/or recording of physiological data. In any case, once the monitoring and/or recording starts, the sensor(s) 810 may transmit the acquired data to the gateway device 830 and/or the server 850 in an at least a continuous manner as described above, for example.

In some embodiments, one or more of the above-noted physiological parameters may be measured periodically, and the sensor(s) 810 may transmit the measurements to the gateway device 830 in an at least a continuous manner as acquired. For example, the periodic measurements may proceed as scheduled and the transmission to the gateway device 830 may occur with little or no delay or latency after data is acquired.

In some embodiments, the sensor(s) 810, or the arrhythmia and fluid monitoring system in general, may be configured to operate some, but not all, of the available features discussed above. For example, the sensors 810 may be configured to monitor and/or acquire one or more of ECG data, thoracic impedance, heart rate, respiration rate, physical activity (e.g., movement), patient posture, etc., but not the others. For instance, the sensors may be configured to monitor and/or acquire data such as ECG data, but not respiration rate, physical activity (e.g., movement), patient posture. Such embodiments may be effected, for example, by including controls in the sensors and/or the system that separately control components of the sensors/system responsible for the features. For example, the arrhythmia and fluid monitoring system may include controls (e.g., power buttons) that separately control the accelerometer and the ECG components of the sensor. By switching on the accelerometer power control and switching off the ECG power control, in some embodiments, one may allow the monitoring and/or acquiring of data related to respiration rate, physical activity, and patient posture while deactivating the monitoring and/or acquiring of ECG data.

In some embodiments, an adhesive patch 860 may be used to attach the sensor(s) 810 to a surface of the body of a patient. FIGS. 9A-E show the sensor 970 disclosed herein, a patch 910 configured to attach the sensor 970 to a patient's body or at least hold the sensor 970 in proximity to skin of the body, and an illustration of a method of attaching the sensor 970 to the patch 910, according to some embodiments. The patch 910 may include a patch frame 930 (e.g., plastic frame) delineating the boundary of the region of the patch 910 that is configured for housing the sensor 970. The patch 910 may be disposable (e.g., single- or few-use patches), and may be made of biocompatible, non-woven material. In some embodiments, the sensor 970 may be designed for long-term usage. In such embodiments, the connection between the patch 910 and the sensor 970 may be configured to be reversible, i.e., the sensor 970 may be configured to be removably attached to the patch 910. For example, the sensor 970 may include components such as snap-in clips 940 that are configured to secure the sensor 970 to the patch 910 (e.g., the patch frame 930) upon attachment (and released the sensor 970 from the patch when separation is desired). The sensor 970 may also include positioning tabs 960 that facilitate the attachment process between the sensor 970 and the patch 910. In some embodiments, the patch may be designed to maintain attachment to skin of a patient for several days (e.g., in the range from about 4 days to about 10 days, from about 5 days to about 7 days, etc.).

In some embodiments, the patch 910 may include additional components that facilitate or aid with the monitoring and/or recording or acquiring of physiological data by the sensor 970. For example, the patch may include conductive elements such as one or more ECG electrodes 920 (e.g., a single lead, two leads, etc.) that can be used when recording ECG data from the surface (e.g., skin contacted directly or through a covering) of a patient's body. The electrodes may be coupled to the sensor 970 by dedicated wiring within the patch. In some embodiments, the ECG may have a sampling rate in then range from about 950 Hz to about 500 Hz, from about 300 Hz to about 450 Hz, from about 350 Hz to about 400 Hz, including values and subranges therebetween. In some embodiments, the ECG signal may be sampled after band-pass filtering by a 12 bit ADC. During normal operation, data may be transferred to the server "as-is" and can then be used by the server algorithms for analysis. In some embodiments, an internal algorithm allows for real-time evaluation of the ECG signal quality upon each attachment of the device to the patient ("attachment test").

Figure 9E:
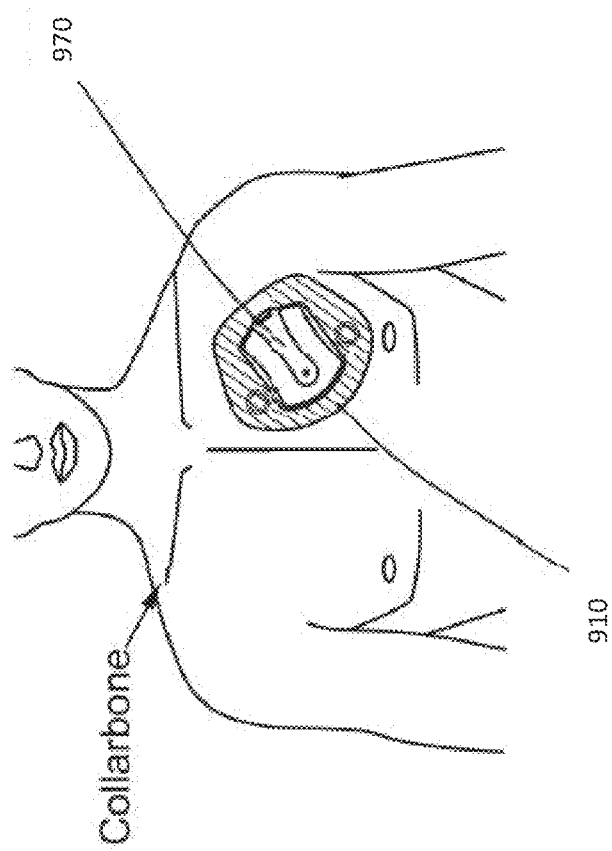
Figure 9D:
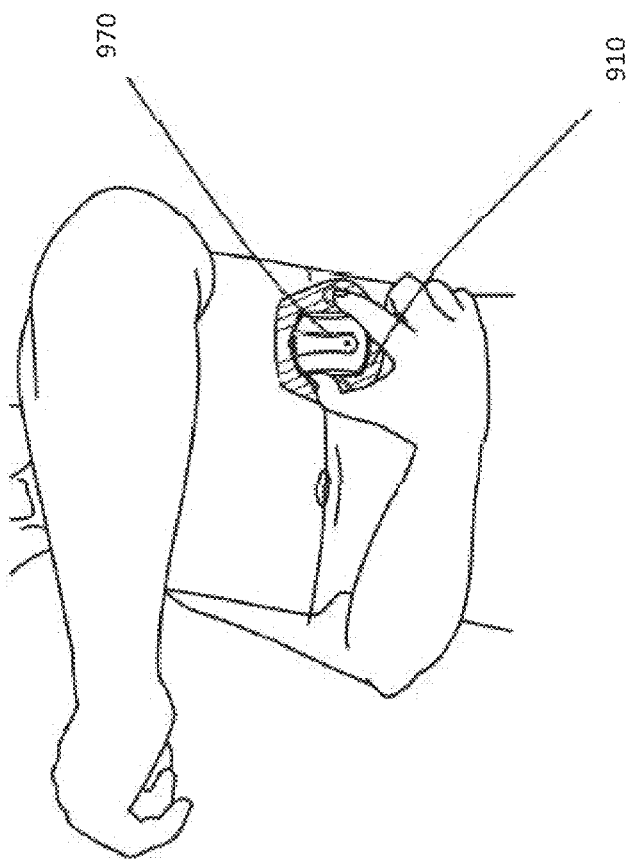

Examples of locations on surface of a patient body at which a patch may be placed are shown in FIGS. 9D-E, where a patch 1020 housing sensor 1010 is shown as placed at on the side (below armpit, for example) (FIG. 9D) and upper chest (FIG. 9E) of the torso of a patient. It is to be noted that the patch may be placed on any part of the surface of a patient's body that allows for efficient monitoring and recording of a physiological data (e.g., area of skin that allows for uniform attachment of the patch 1020 to the skin). For example, one may place the patch 1020 under an armpit at the nipple level for performing lung fluid level measurements. With respect to ECG measurements, the ECG signal at this location may be represented as the difference between standard V5 and V6 leads of an ECG.

Figure 10B:
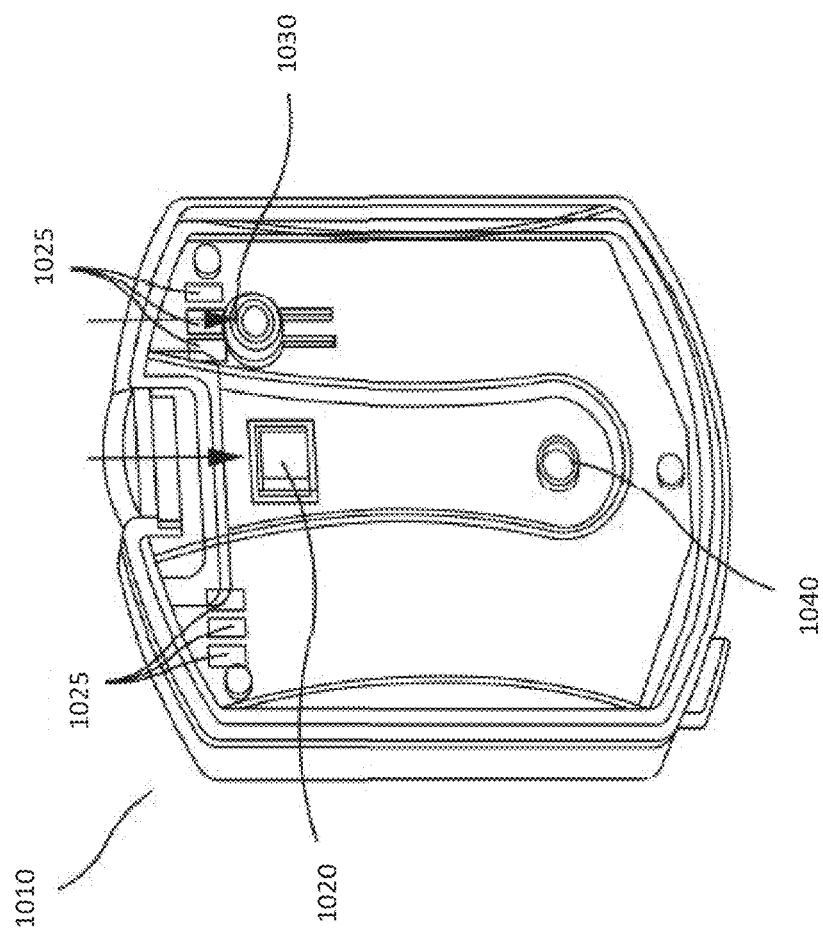
FIGS. 10A-C show example front, back and exploded views, respectively, of the sensor(s) (e.g., of external heart monitoring device(s)) disclosed herein, according to some embodiments.
Figure 10A:
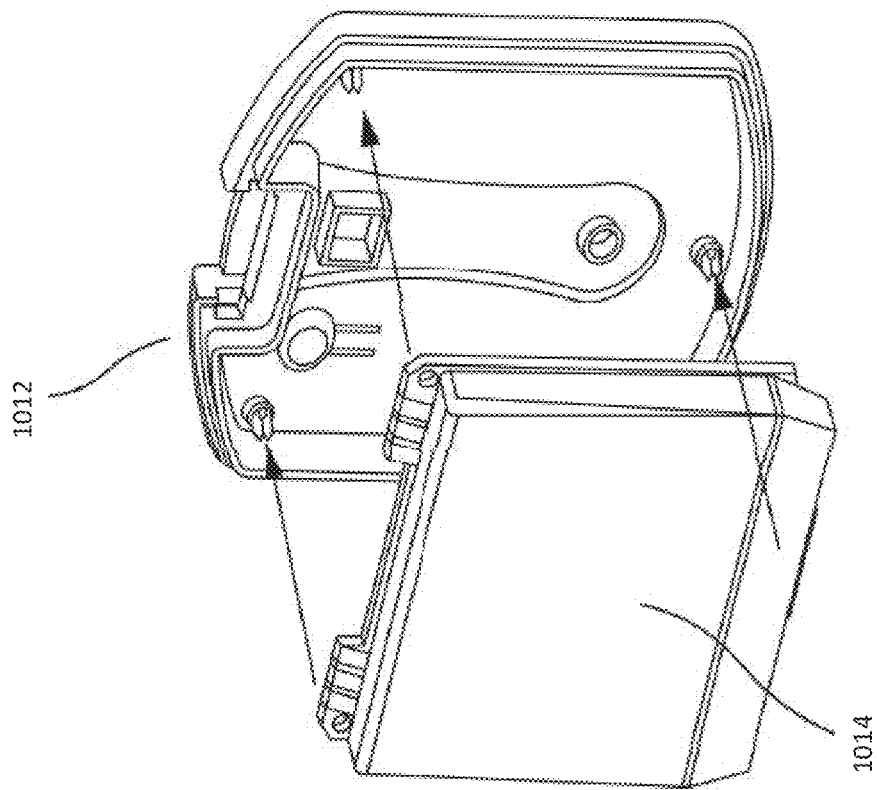
Figure 10C:
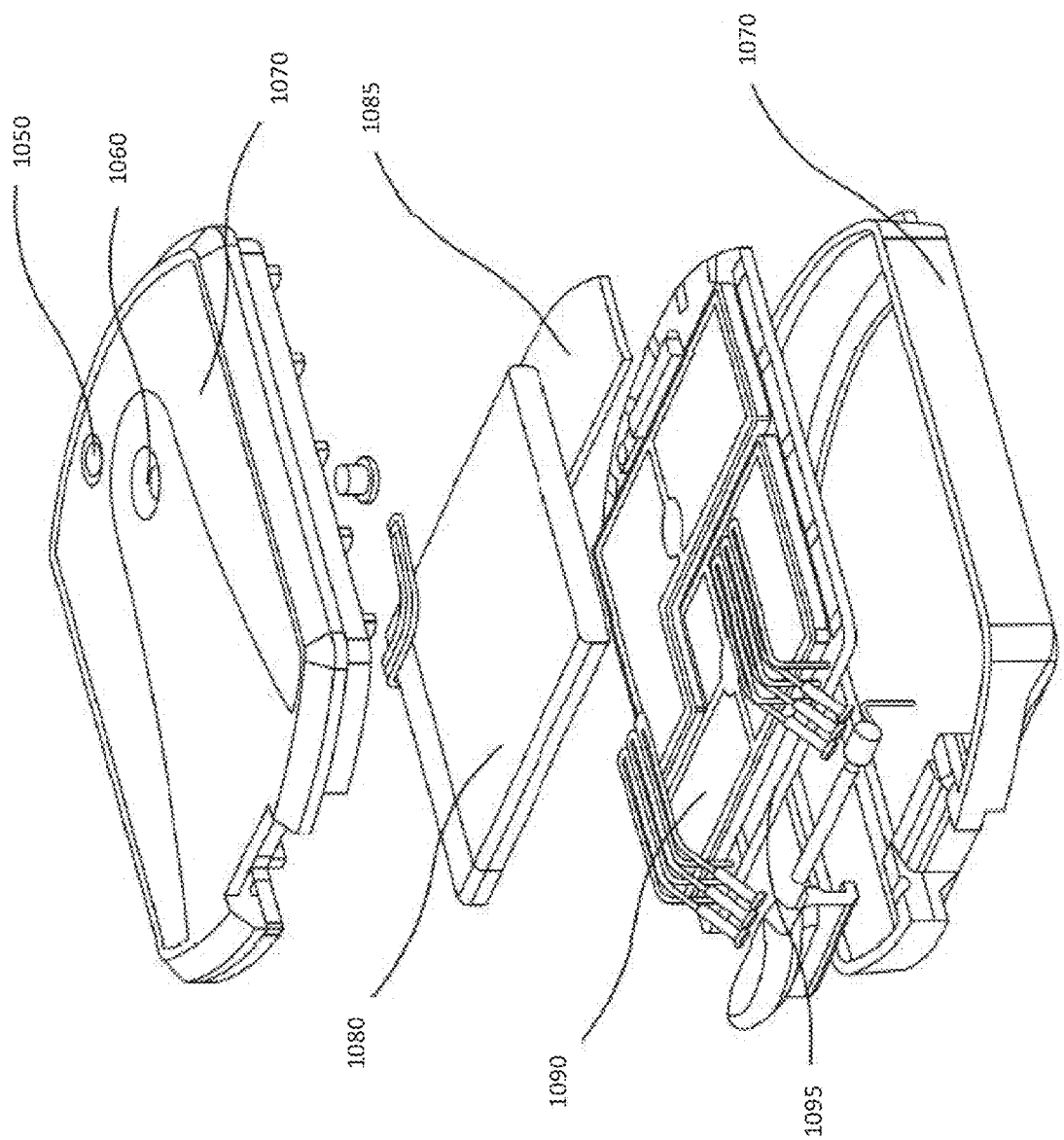

With reference to FIGS. 10A-C, in some embodiments, front, back and exploded views, respectively, of the sensor(s) disclosed herein are shown. FIG. 10A shows the front 1012 and back 1014 covers of the sensor 1010 (labelled as top and bottom covers 1070 in FIG. 10C). In some embodiments, such covers may couple to each other to seal the electrical components of the sensor from the surrounding environment (e.g., electrical sealing). In such embodiments, metallic tabs 1025 may protrude outside the covers to provide electrical connection for situations such as performing ECG measurements, charging power source and/or the like.

FIG. 10B shows that the sensor 1010 may include one or more indicators that identify the status of the sensor 1010 to the user of the sensor 1010. Examples of such indicators include but are not limited to light indicator 1040 (e.g., a light emitting diode (LED) indicator) and sound indicators 1020. In some embodiments, the indicators 1020, 1040 provide feedback on the status of the sensor 1010 and components thereof, such as the charging and/or power level of the power source of the sensor 1010 (e.g., a battery), the attachment level of the sensor 1010 to the patch 910, the attachment level of the patch 910 to the surface of the body to which the patch 910 is attached, etc. As another example, the sensor may respond by blinking (e.g., via the light indicator 1040) or buzzing (e.g., via the sound indicator 1020) in response to an engagement by a patient to indicate possible symptoms.

In some embodiments, FIG. 10C provides an exploded view of the sensor 1010 depicting at least some of the components of the sensor. For example, the sensor 1010 may comprise a power source such as a battery 1080, a light indicator 1060, a button 1050 for facilitating the interaction of a patient, a healthcare provider, and/or a technician with the sensor, a wireless communications circuit 1085, a radio frequency shield 1090 (such as a metallic cover, e.g., to prevent interferences with the ECG processing and other digital circuitry), a digital circuitry board 1095, and/or the like. FIG. 10C shows a Bluetooth unit as an example of a wireless communications circuit 1085, although in addition to or alternatively to the Bluetooth unit, other modules facilitating other types of communications (examples of which including WiFi®, cellular, etc.) may be included in the sensor 1010.

In some embodiments, the sensor 1010 may also include input interfaces such as buttons for interfacing with a user. For example, the sensor may include a button 1030 that allows a patient or a health care professional to activate or deactivate the sensor 1010. Such input interfaces may be configured to avoid or at least minimize unintended interactions with a user. For example, a button may be sized and shaped to avoid accidental activation (e.g., the button may be configured to require activation by being pushed in with an external object). This button may be used to reset the sensor as well as pair the sensor to the gateway device and initiate communication. In some embodiments, the input interface of the sensor may include a touch screen configured to receive input from a user and/or provide information back to the user. For example, the input may allow the user to set the sensor in an "airplane mode," i.e., for example by deactivating any wireless communication (e.g., Wi-Fi, Bluetooth, etc.) with external devices and/or servers. For example, the button can be implemented as a magnetic switch, e.g., an embedded magnetic switch, instead of a physical button. Such an implementation can be useful for designing the housing of the device and avoid exposing button components to the environment.

Figure 11A:
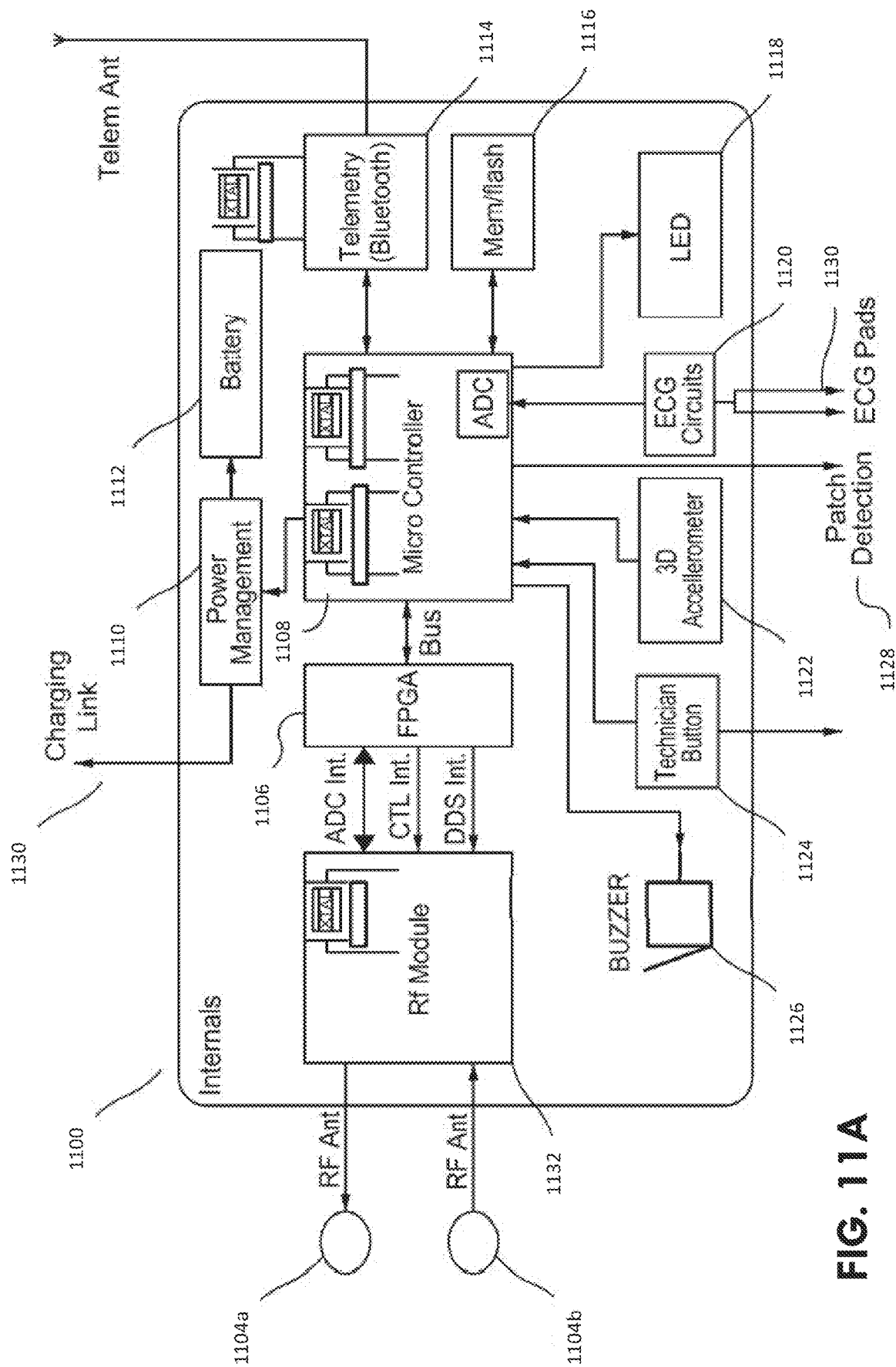
FIG. 11A shows an example illustration of device electronics architecture for measurements and transmission of patient physiological data (e.g., biometric data), according to some embodiments.

In some embodiments, as described above, the disclosed sensor is configured to monitor and/or acquire data on physiological parameters including but not limited to electrocardiogram (ECG) data, thoracic impedance, heart rate, respiration rate, physical activity, posture and/or the like. To that effect, the sensor and/or the patch housing the sensor may include components that facilitate or undertake the monitoring and/or recording of at least some of these parameters. For example, as noted above, the patch housing the sensor may include ECG electrodes coupled to the sensors to facilitate the monitoring and/or acquiring of ECG data. As shown in FIG. 11A, which shows an example embodiment of device electronics architecture for measurements and transmission of patient physiological data, the sensor includes EGG processing circuitry configured to couple to the ECG electrodes embedded in the patch housing the sensor itself. The ECG processing circuitry is configured to, for example, perform filtering, amplification, and/or removal of noise, low frequency variations in the signal, and other signal artifacts.

As another example, the sensor may include radio frequency (RF) antenna for directing electromagnetic waves into a body of a patient and receiving waves that are scattered and/or reflected from internal tissues. Further, the sensor may include RF circuitry or module configured to process the received waves so as to determine some properties of the tissues that are on the path of the transmitted and/or scattered/reflected waves. For example, the antenna may direct RF waves towards a lung of a patient and the RF circuitry may analyze the scattered/reflected waves to perform an RF-based measurement of the lung fluid level of the patient. FIG. 11A shows an example embodiment of a sensor comprising RF antennas, an RF module and circuits for controlling the module (e.g., field-programmable gate array (FPGA) circuits).

With reference to FIG. 11A, in some embodiments, the sensor 1100 includes external interfaces such as but not limited to RF antennas (e.g., bi-static) 1104a, 1104b for transmitting & receiving RF signals, a button or switch 1124 for activating or deactivating the sensor 1100, an LED 1118 and a buzzer 1126 for providing light and audio feedback to a user of the sensor 1100, a battery charging link 1130 coupled to a power management module 1110 for charging an onboard power source such as a battery 1112, and ECG pads 1130 for recording synchronization signal. In some embodiments, the sensor 1100 may also include a wireless link (e.g., Bluetooth®) (not shown) to provide an external server access to the sensor 1100 so as to exert at least some control on the sensor 1100.

Internally, in some embodiments, the sensor 1100 may include a microprocessor 1108 (which may be alternatively referred to as a micro-controller) that includes instructions thereon specifying how measurements (RF, ECG, accelerometer, etc.) are taken and the obtained data are transmitted, how to relay the status of the sensor 1100, how/when the sensor 1100 can enter the plurality of sleep levels, and/or the like. In some embodiments, the instructions may also specify the conditions for performing certain types of measurements. For example, the instructions may specify that the accelerometer may not commence measurements (for physical activity, and patient posture, for example) unless the user of the sensor is at rest or maintaining a certain posture. As another example, the instructions may identify the conditions that may have to be fulfilled before ECG measurements can commence, such conditions including at least sufficient attachment level between the sensor and the surface on the body to which the sensor 1100 is attached. In some embodiments, the microprocessor 1108 may have internal and external non-volatile memory banks that can be used for keeping measurement directory and data, scheduler information, and/or a log of actions and errors. This non-volatile memory allows saving power via a total power-down while retaining data and status information.

Figure 11B:
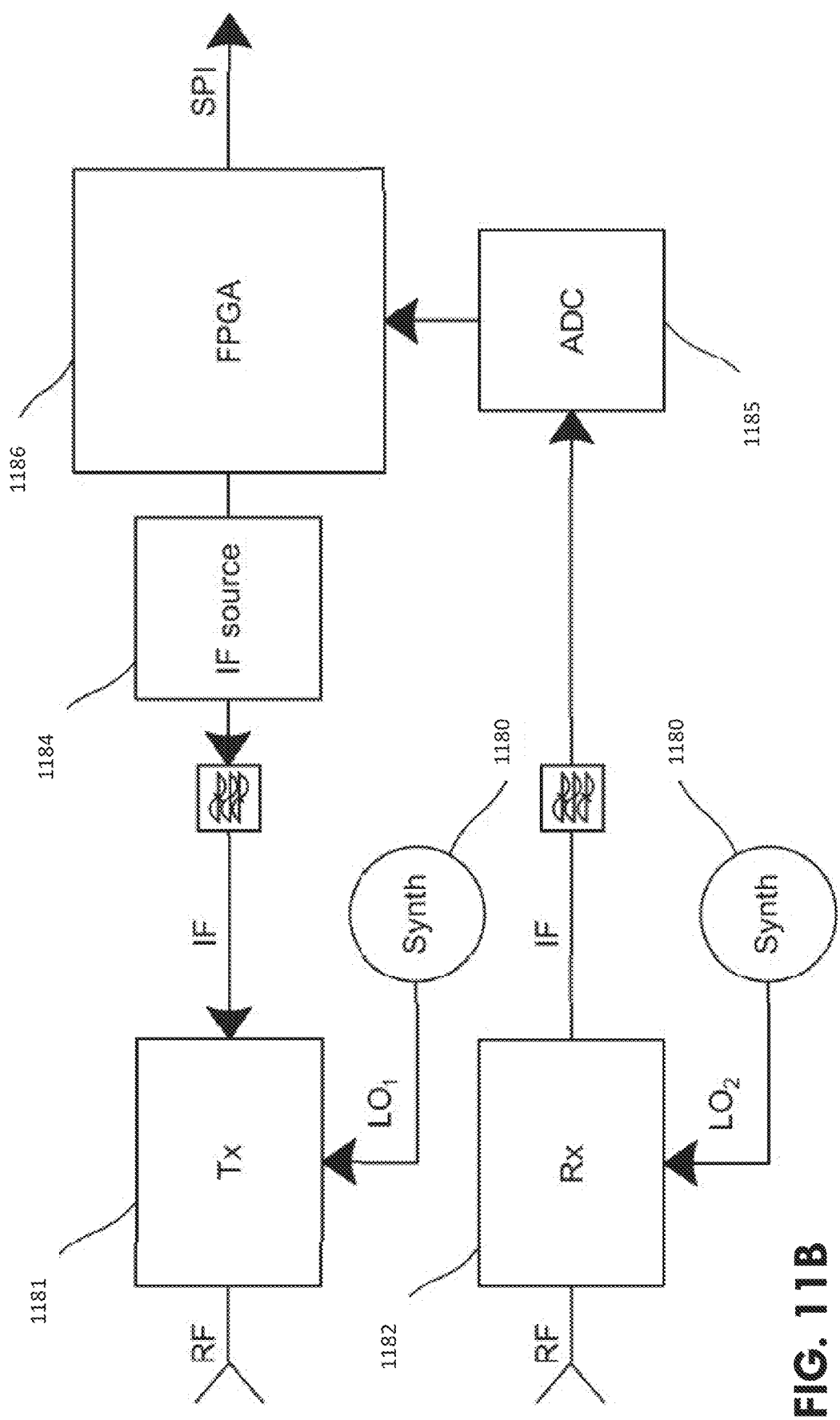
FIG. 11B shows a block diagram of example architecture of a radio frequency (RF) module, according to some embodiments.
Figure 11C:
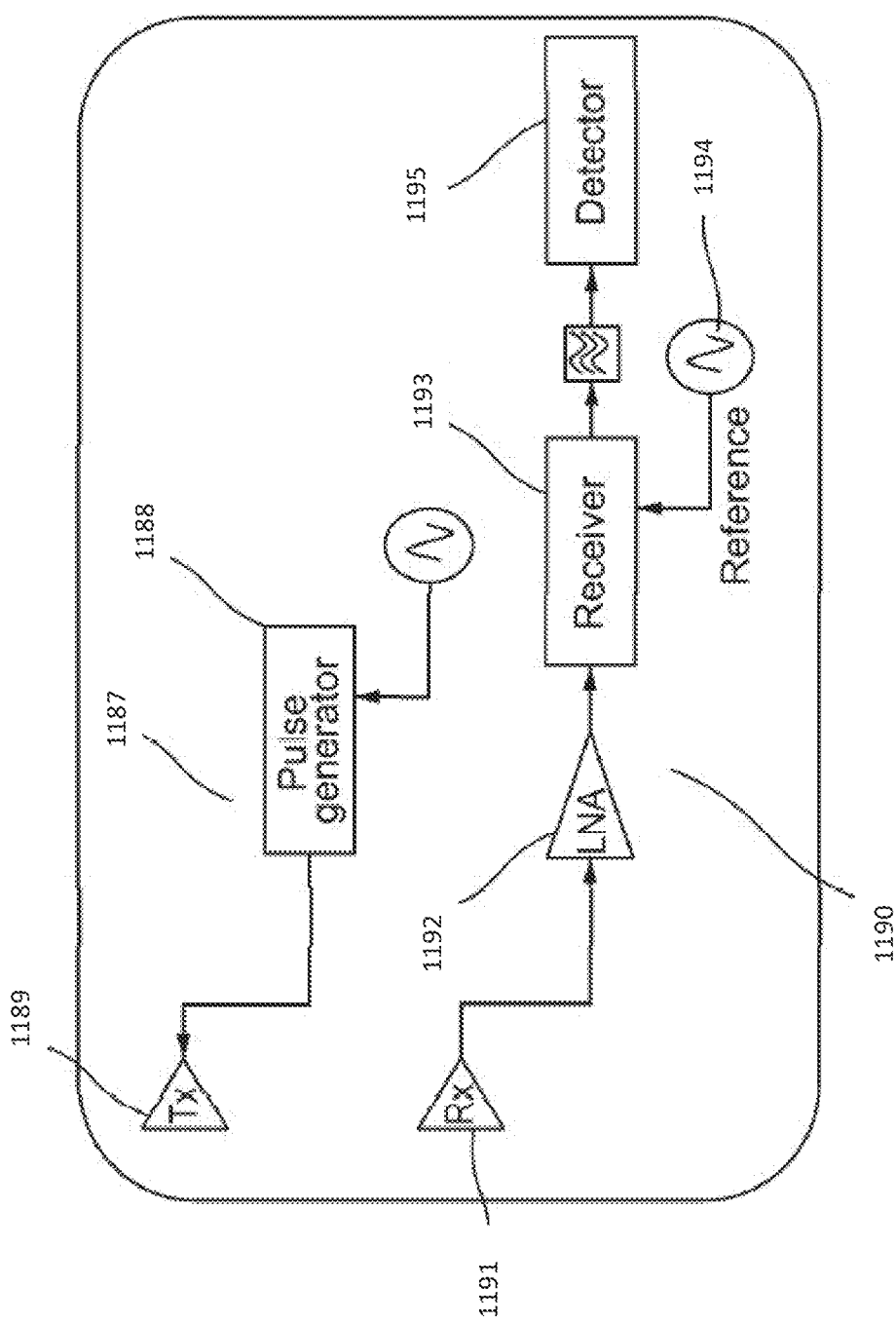
FIG. 11C shows a block diagram of another example architecture of an RF module, according to some embodiments.

FIGS. 11B and 11C are block diagrams that illustrate examples of RF sensor functionality disposed within an RF module (e.g., RF module 1132) according to some embodiments. As noted herein, such functionality may be used for RF based fluid monitoring of fluid accumulation/content in tissue in accordance with the techniques described herein. Referring first to FIG. 11B, initially, one or more RF signals (e.g., a single "LO" signal, or different "$LO_1$," and "$LO_2$" signals, collectively "LO" signals) can be generated by a broadband synthesizer 1180 (e.g., a pulse generator and synthesizer—LO). Such a synthesizer 1180 can preferably include moderate phase noise performance and fast settling time capabilities (in some embodiments, one or the other). The RF module includes a transceiver portion 1181, including a transmitting antenna (Tx) and associated circuitry for transmitting RF waves directed, for example, towards a tissue of interest in the patient's body, and a receiver portion 1182, including a receiver antenna (Rx) and associated circuitry 1182 for receiving reflected RF waves from, for example, the tissue of interest in the patient's body.

The LO signal at the transceiver (Tx) of the transmitter portion 1181 is multiplied with an external sine wave at a low frequency intermediate frequency (IF) signal, generated by an IF source 1184, and directed to the output of the transceiver (Tx). As noted above, the LO signal at transceiver portion 1181 and the receiver portion 1182 can be generated by one or two LO sources (e.g., synthesizer(s) 1180). Output power can be controlled via digital control of a digitally controlled attenuator (DCA) on the RF transceiver path. An external reflected RF wave returning to a receiving antenna (Rx) is directed to the receiver portion and down-converted to an IF frequency by a down conversion mixer. The reflection characteristics (phase and amplitude) can be transformed to a new IF carrier (e.g., on the order of 250 KHz), filtered and amplified before the ADC 1185.

Digital control for the functionality in FIG. 11B may be achieved directly by a processor and/or digital logic (e.g., an FPGA 1186), which may be configured to control both the transceiver's configuration process, IF signal adjustments and associated switching.

Referring now to FIG. 11C, in some embodiments, the RF module 1132 may be implemented using a transmitting portion 1187 and receiver portion 1190 as shown. For example, the transmitting portion 1188 can include a pulse generator 1188 and a transmitting antenna Tx 1189 for transmitting the RF waves directed towards a tissue of interest in the patient's body. the receiver portion 1190 may include a receiving antenna Rx 1191, a low-noise RF amplifier 1192, a receiver 1193 that converts the reflected RF signals to an IF signal by using mixer and local oscillator 1194, which may be a monostatic (sheared LO) or a bi-static system. The signal can be filtered, amplified and fed in to a detector 1195, the output of which may be connected to additional circuitry for further signal processing.

With respect to potential RF/ECG interference, in some embodiments the following steps can be taken:

Ground Separation between digital and RF components: may be achieved by separating the digital and RF grounds, and utilizing a single connection point through ferrite bead.

RF module shielding may also be used which may comprise a metallic cover, for example, radio frequency shield 1090 as shown in FIG. 10C.

Power circuitry considerations: different power paths may be utilized for different components/modules. Additionally, the power circuit may include filters to avoid noise.

ECG filtering may also be used to aid in minimizing RF interference which prevents high frequency signals interfering with the ECG circuitry/module.

Circuitry layout: ECG signal paths are physically separated from RF paths. In some embodiments, the ECG signal paths can also be physically separated from other lines that might interfere.

FIG. 11C shows an example general architecture of the RF module with low frequency IF and shared local oscillator (LO). As an example non-limiting example, with reference to FIG. 11C, the transmitted RF signal may be mixed with the IF signal (e.g., about 250 KHz) before transmission, so the transmission is actually 2 tones around the carrier RF signal, separated by about 500 KHz.

In some embodiments, the RF module 1132 may include a calibration path (e.g., an electric reflector such as but not limited to a resistor on board) which generates a steady and constant or near-constant reflection uncorrelated with the external propagation path. This reflector generates a reflection profile with minimal dependencies to temperature, system noise and device location on the body.

In some embodiments, the RF module 1132 itself may not have any processing components inside. For example, it may be controlled by a field-programmable gate array (FPGA) that defines in each or nearly each frequency point one or more of the frequency, output power levels, system gain, bypassing modes and/or enable/disable transmissions.

In some embodiments, the RF module 1132 may support different types of waveform configurable options, including but not limited to normal operation, calibration frame operation, interleaved switching between normal and calibration frame operation, interleaved switching between normal and delayed path operation, and clear channel sensing. In some of these options, for example the normal and interleaved switching ones, the attenuation may be different per frequency, while in the case of clear channel sensing, there may not be any transmission. For the calibration frame operation, the attenuation can be the same for all frequencies but may be higher when compared to those of the normal operation.

In some embodiments, the transmit (Tx) and receive (Rx) switches may be respectively set to transmit and receive through a calibration path for the case of calibration frame operation, while for the clear channel sensing, Rx switch may be set to antenna and Tx to calibration path. For interleaved switching between normal and calibration frame operations and between normal and delayed path operations, in some embodiments, the Tx and Rx switches may alternate between calibration and antenna path per frequency, and normal and delayed path, respectively.

In some embodiments, the RF waves may be in the frequency ranges from about 100 MHz to about 1 GHz, 200 MHz to about 2.5 GHz, from about 200 MHz to about 3 GHz, from about 500 MHz to about 5 GHz, including values and subranges therebetween. In some embodiments, a thoracic fluid content (TFC) sensitivity may be configured to allow measurement of heart signals at distances up to about 25 cm, about 20 cm, about 15 cm, about 10 cm, about 5 cm, including values and subranges therebetween, inside the body onto which the disclosed sensor is attached. In some embodiments, the dynamic range is no less than 100 dB, measured in the presence of a strong coupling signal between transmission & reception. Further the waveform may be stepped frequency (16-128 frequencies), arbitrary with 1 MHz accuracy & resolution. In some embodiments, actual frequencies selected may be contiguous or not, depending on regulatory requirements. In some embodiments, the dwell and settling times may be configurable to allow 16-128 frequencies within less than 5 to 20 ms, respectively.

Details on RF-based measurements of physiological parameters such as thoracic fluid content have been discussed in U.S. Patent Publication No.: US 2011/0130800, filed Apr. 14, 2010, titled "Methods and Systems for Determining Fluid Content of Tissue"; and PCT International Patent Publication No.: WO 2012/011066, filed Jul. 21, 2011, titled "Implantable Dielectrometer," the disclosures of which are incorporated by reference herein in their entireties.

It has been noted above that the sensor may include indicators providing information on the attachment level of the patch housing the sensor to a skin of the wearer of the sensor. Such information may be obtained from RF-based measurements as discussed in PCT International Patent Publication No.; WO 2016/115175, filed Jan. 12, 2016, titled "Systems, Apparatuses, and Methods for Radio Frequency-Based Attachment Sensing," the disclosure of which is incorporated by reference herein in its entirety.

In some embodiments, the FPGA 1106, with a top-level view of which shown in FIG. 11D, may be configured to interface with the RF module 1132. For example, the FPGA 1106 is configured to one or more of control the transceiver module, control the RF discrete pins, control the ADC module, generate the IF signal for the RF module 1132, and acquire ADC (analog-digital conversion) output samples, synchronized with the generated IF signal. Further, in some embodiments, the FPGA 1106 is configured to process the ADC output samples to generate the baseband data. In addition, in some embodiments, the FPGA 1106 may be configured to interface with the microcontroller or microprocessor 1108. For example, the FPGA 1106 may start RF transmission (per frame) upon command from microprocessor 1108, save baseband data to local RAM, per frame, for microprocessor 1108 to read, allow microprocessor 1108 read/write transactions towards configuration memory, provide a debug interface for the microprocessor 1108, and/or allow microprocessor 1108 to change configuration settings using a dedicated memory.

In some embodiments, the FPGA can support up to 128 frequencies, allowing for a different gain and dwell time per frequency. In some embodiments, power consumption can be minimized by using several clock frequencies within the design and gating unused clock signals. In some embodiments, microprocessor data acquisition can be performed using a separate clock, allowing the shut-down of the entire control & processing pipe while reading the data.

In some embodiments, the sensor disclosed herein may comprise an accelerometer and the accelerometer may be used to determine one or more of the physical activity, posture and respiration rate of a patient wearing the sensor. For example, a three-axis (3D) accelerometer 1122 may be used to acquire data on patient movements and posture as well as the respiration rate, and a processor (of the sensor or an external server, for example) receiving the acquired data may use the data (e.g., in conjunction with data obtained by the sensor such as ECG data or RF-based measurements) to determined physiological parameters of the patient, such as the lung fluid level of the patient. The 3D accelerometer 1122 may be used to aid RF and/or ECG analysis by detecting different types of motion segments in the recording so that the conditions of the measurements of the RF and/or the ECG may be interpreted/analyzed accordingly. For example, in some embodiments, RF and/or ECG measurements may be performed while the patient wearing the sensor is active or at rest. The analysis of the RF and/or ECG data may then depend on the state of the patient's physical activity (e.g., at rest, low intensity activity, high intensity activity, etc.). In such embodiments, the accelerator may be used to identify the patient's physical state so as to properly analyze and interpret the RF and/or ECG measurements.

In some embodiments, the accelerometer 1122 may also contain an internal tap detector, which may be used for generating a patient triggered event (e.g., using "double tap" feature). The acceleration signal can be used to calculate respiration rate. FIG. 11A shows an example embodiment of a sensor comprising a 3D accelerometer 1122, RF antennas 1104a, 1104b, ECG processing circuitry coupled to ECG electrodes, a microcontroller 1108 (which may be alternatively referred as microprocessor throughout this disclosure) and a telemetry (e.g., Bluetooth®) 1114. In such embodiments, for example, the micro-controller 1108 may receive data on patient respiration rate, movements, posture, ECG as well as RF-based measurements of the patient and process, and/or transmit to an external processor via the telemetry 1114 for further processing, to determine a physiological parameter of the patient. As an example, the micro-controller 1108 of the sensor may cause the Bluetooth® telemetry 1114 to transmit the noted data and measurements to an external server which in turn analyzes the RF measurements, the ECG, posture, movement, and/or respiration rate data to determine the lung fluid level of the patient. As an another example, the external server may analyze ECG data to determine patient health conditions related to one or more of a heart rate, atrial fibrillation, flutter, supraventricular tachycardia, ventricular tachycardia, pause, atrioventricular (AV) block, ventricular fibrillation, bigeminy, trigeminy, ventricular ectopic beats, supraventricular ectopic beats (SVEB), bradycardia, and tachycardia. The determination of patient physiological health parameters (e.g., lung fluid level or the above-noted health conditions) may allow the server to provide a notification on health-related events of the patient wearing the sensor for which the data came. For example, upon determining an arrhythmia condition from data received from a sensor, an external server may provide a notification indicating a cardiac event with respect to the wearer of the sensor that transmitted the data.

In some embodiments, the sensor may also include a temperature sensor, conductance sensor, a pressure sensor, a respiration sensor, SPO2, and/or a light sensor. For example, a respiration sensor can include an accelerometer configured to monitor the patient's chest movements, e.g., during certain portions of the day and/or night or during an RF measurement. For instance, a 3D multi-axis, multi-channel accelerometer can be configured to, on a first channel, monitor for a patient movement and/or posture, and on a second, different channel, monitor the chest movements of the patient to determine respiration rate and other related data. Alternatively, a respiration accelerometer can be provided in the device that is separate from a posture sensing accelerometer. In some examples, the respiration rate measurement can be based on the operation of a tri-axis microelectromechanical system (MEMS) accelerometer within the device mounted on the patient's torso. The accelerometer can measure projections of the gravity vector on its intrinsic axes. From these measurements, a respiration rate can be derived based on measured quasi-periodic changes of the projections that occur due to respiration movements of the patient's rib cage.

In other examples, the respiration rate and/or other respiration data can be derived from the RF signals themselves. For example, dedicated respiration circuitry can be provided and/or the processor can be configured with instructions to cause the processor to monitor the reflected RF waves as described herein and determine respiration rate and related data therefrom. In some embodiments, respiration characteristics such as exhale vs. inhale times can also be measured via an accelerometer and health conditions such as sleep apnea may be detected from accelerometer measurements.

In some embodiments, RR, which denotes ventricular interbeat interval on ECG, may be derived from ECG data and the RR accuracy can be improved by fusing the data from two or more of these RR measurement methods.

When using the disclosed sensor, in some embodiments, there are scenarios that involve the removal of the adhesive patch from the skin of a body, either by involving the transfer of sensors from old patient to new patient or when replacing faulty sensors. For example, when a device is in a charger or on a patient in error, it can be disassociated from the patient through a server action. Similarly, if the device is newly assigned to a patient, the device can be associated with a new patient through a server action. In some embodiments, certain operational modes of the sensor may not include all aspects of the sensor's operational capability. For example, situations involving automatic built-in tests, regulation tests, debugging, handling when the sensor is faulty, etc., one or more features of the sensor may not be activated or operational (or may operate differently than when the sensor is fully or normally operational) while the sensor itself is operating. For example, when debugging a faulty system, in some embodiments, transmission may be conducted via a single specific frequency by allowing configuring a specific frequency and triggering start/stop transmission.

| | |
|---|---|
| Overall dimensions | Smaller than about 55 mm × about 70 mm × about 17 mm |
| Maximum weight | Less than about 70 grams |
| ECG attachment | Embedded in adhesive patch |
| Gel | using hydrogel embedded in patch |
| Device liquid/dustproofing | Ultrasonic sealing, tested according to IP67 |
| Package | Contents: 1 device, charging cradle, User manual and disposable patches; Patches must be packed appropriately to avoid glue dehydration. |
| Labelling | Device should be labelled with serial number & FCC ID. Label must withstand environmental conditions according to IP67 |
| Soft feel | Rubber like feel, little or no sharp edges |
| Push-Button | Multipurpose; designed to be used by technician; protected from accidental activation by the patient to preserve power; Used for reset, pairing and to initiate communication |
| LED | Multipurpose; dual color; indicates battery status, pairing, errors, BT connection. |

| | |
|---|---|
| Device-in-patch sensing | electrical-connection |
| Buzzer | Audio notification, between about 1 and about 3 KHz and over about 60 dBSPL intensity at a distance of 1m. |
| PCB placement and case closure | Without screws |
| Drop protection | Device is designed to comply with drop tests according to standard IEC 60601-1 and 60601-1-11 |

Figure 12:
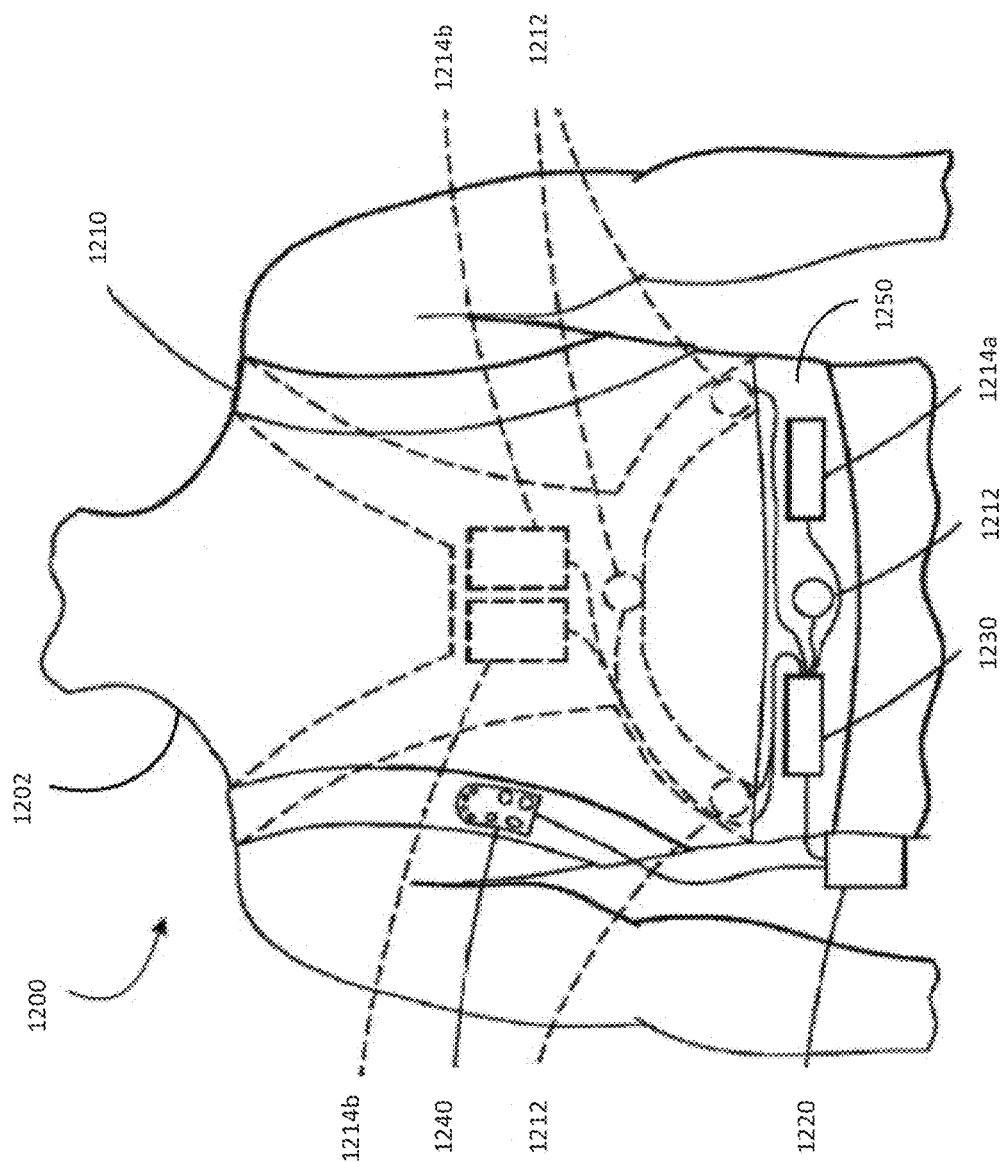
FIG. 12 illustrates an example medical device (e.g., external heart monitoring device) that is external, ambulatory, and wearable by a patient, according to some embodiments.

FIG. 12 illustrates an example heart monitoring device, e.g., medical device 1200 that is external, ambulatory, and wearable by a patient 1202, and configured to implement one or more configurations described herein. For example, the medical device 1200 can be a non-invasive medical device configured to be located substantially external to the patient. Such a medical device 1200 can be, for example, an ambulatory medical device that is capable of and designed for moving with the patient as the patient goes about his or her daily routine. For example, the medical device 1200 as described herein can be bodily-attached to the patient such as the LifeVest® wearable cardioverter defibrillator available from ZOLL® Medical Corporation. In one example scenario, such wearable defibrillators can be worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 1200 can include one or more of the following: a garment 1210, one or more sensing electrodes 1212 (e.g., ECG electrodes), one or more therapy electrodes 1214a and 1214b (collectively referred to herein as therapy electrodes 1214), a medical device controller 1220, a connection pod 1230, a patient interface pod 1240, a belt 1250, or any combination of these. In some examples, at least some of the components of the medical device 1200 can be configured to be affixed to the garment 1210 (or in some examples, permanently integrated into the garment 1210), which can be worn about the patient's torso.

The medical device controller 1220 can be operatively coupled to the sensing electrodes 1212, which can be affixed to the garment 1210, e.g., assembled into the garment 1210 or removably attached to the garment, e.g., using hook and loop fasteners. In some implementations, the sensing electrodes 1212 can be permanently integrated into the garment 1210. The medical device controller 1220 can be operatively coupled to the therapy electrodes 1214. For example, the therapy electrodes 1214 can also be assembled into the garment 1210, or, in some implementations, the therapy electrodes 1214 can be permanently integrated into the garment 1210.

Component configurations other than those shown in FIG. 12 are possible. For example, the sensing electrodes 1212 can be configured to be attached at various positions about the body of the patient 1202. The sensing electrodes 1212 can be operatively coupled to the medical device controller 1220 through the connection pod 1230. In some implementations, the sensing electrodes 1212 can be adhesively attached to the patient 1202. In some implementations, the sensing electrodes 1212 and at least one of the therapy electrodes 1214 can be included on a single integrated patch and adhesively applied to the patient's body.

The sensing electrodes 1212 can be configured to detect one or more cardiac signals. Examples of such signals include ECG signals and/or other sensed cardiac physiological signals from the patient. In certain implementations, the sensing electrodes 1212 can include additional components such as accelerometers, acoustic signal detecting devices, and other measuring devices for recording additional parameters. For example, the sensing electrodes 1212 can also be configured to detect other types of patient physiological parameters and acoustic signals, such as tissue fluid levels, heart vibrations, lung vibrations, respiration vibrations, patient movement, etc. Example sensing electrodes 1212 include a metal electrode with an oxide coating such as tantalum pentoxide electrodes, as described in, for example, U.S. Pat. No. 6,253,099 entitled "Cardiac Monitoring Electrode Apparatus and Method," the disclosure of which is incorporated by reference herein in its entirety.

In some examples, the therapy electrodes 1214 can also be configured to include sensors configured to detect ECG signals as well as other physiological signals of the patient. The connection pod 1230 can, in some examples, include a signal processor configured to amplify, filter, and digitize these cardiac signals prior to transmitting the cardiac signals to the medical device controller 1220. One or more of the therapy electrodes 1214 can be configured to deliver one or more therapeutic defibrillating shocks to the body of the patient 1202 when the medical device 1200 determines that such treatment is warranted based on the signals detected by the sensing electrodes 1212 and processed by the medical device controller 1220. Example therapy electrodes 1214 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 1214 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) or a patient. Alternatively, the optional therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 13:
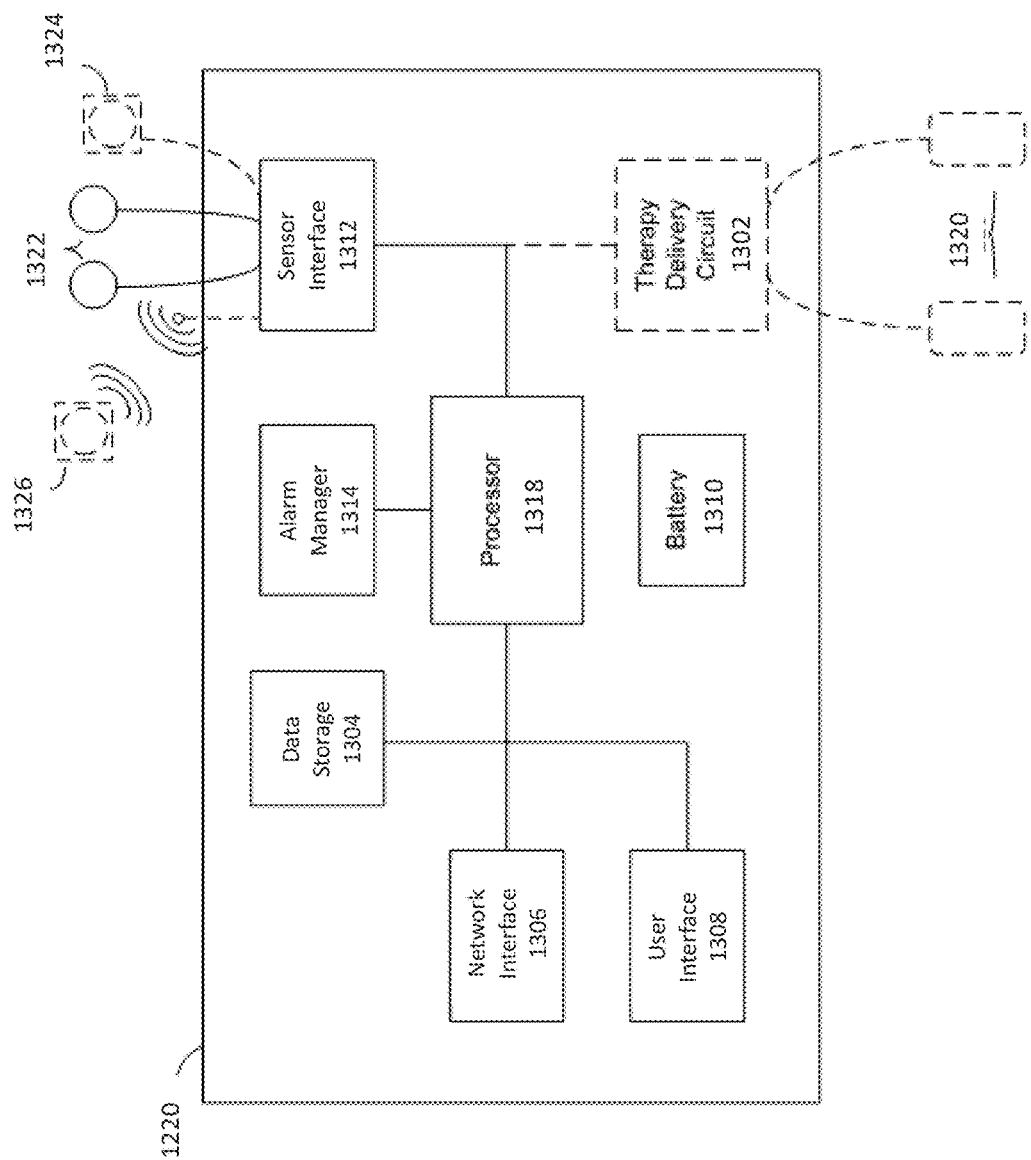
FIG. 13 illustrates an example component-level view of a medical device (e.g., external heart monitoring device), according to some embodiments.

FIG. 13 illustrates a sample component-level view of the medical device controller 1220. As shown in FIG. 13, the medical device controller 1220 can include a therapy delivery circuit 1302, a data storage 1304, a network interface 1306, a user interface 1308, at least one battery 1310, a sensor interface 1312, an alarm manager 1314, and at least one processor 1318. A patient monitoring medical device can include a medical device controller 1220 that includes like components as those described above, but does not include the therapy delivery circuit 1302 (shown in dotted lines).

The therapy delivery circuit 1302 can be coupled to one or more electrodes 1320 configured to provide therapy to the patient (e.g., therapy electrodes 1214 as described above in connection with FIG. 12). For example, the therapy delivery circuit 1302 can include, or be operably connected to, circuitry components that are configured to generate and provide the therapeutic shock. The circuitry components can include, for example, resistors, capacitors, relays and/or switches, electrical bridges such as an h-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 1318) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between 350 to 500 volt surge rating and can be charged in approximately 15 to 30 seconds from a battery pack.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating patients at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the patient's body impedance. The therapy delivery circuit 1302 can be configured to perform the switching and pulse delivery operations, e.g., under control of the processor 1318. As the energy is delivered to the patient, the amount of energy being delivered can be tracked. For example, the amount of energy can be kept to a predetermined constant value even as the pulse waveform is dynamically controlled based on factors such as the patient's body impedance which the pulse is being delivered.

The data storage 1304 can include one or more of non-transitory computer readable media, such as flash memory, solid state memory, magnetic memory, optical memory, cache memory, combinations thereof, and others. The data storage 1304 can be configured to store executable instructions and data used for operation of the medical device controller 1220. In certain implementations, the data storage can include executable instructions that, when executed, are configured to cause the processor 1318 to perform one or more functions.

In some examples, the network interface 1306 can facilitate the communication of information between the medical device controller 1220 and one or more other devices or entities over a communications network. For example, where the medical device controller 1220 is included in an ambulatory medical device (such as medical device 1200), the network interface 1306 can be configured to communicate with a remote computing device such as a remote server or other similar computing device. The network interface 1306 can include communications circuitry for transmitting data in accordance with a Bluetooth® wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain implementations, the user interface 1308 can include one or more physical interface devices such as input devices, output devices, and combination input/output devices and a software stack configured to drive operation of the devices. These user interface elements may render visual, audio, and/or tactile content. Thus the user interface 1308 may receive input or provide output, thereby enabling a user to interact with the medical device controller 1220.

The medical device controller 1220 can also include at least one battery 1310 configured to provide power to one or more components integrated in the medical device controller 1220. The battery 1310 can include a rechargeable multi-cell battery pack. In one example implementation, the battery 1310 can include three or more 13200 mAh lithium ion cells that provide electrical power to the other device components within the medical device controller 1220. For example, the battery 1310 can provide its power output in a range of between 20 mA to 1000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 1220.

The sensor interface 1312 can be coupled to one or more sensors configured to monitor one or more physiological parameters of the patient. As shown, the sensors may be coupled to the medical device controller 1220 via a wired or wireless connection. The sensors can include one or more electrocardiogram (ECG) electrodes 1322 (e.g., similar to sensing electrodes 1212 as described above in connection with FIG. 1), heart vibrations sensors 1324, and tissue fluid monitors 1326 (e.g., based on ultra-wide band radiofrequency devices).

The ECG electrodes 1322 can monitor a patient's ECG information. For example, the ECG electrodes 1322 can be galvanic (e.g., conductive) and/or capacitive electrodes configured to measure changes in a patient's electrophysiology to measure the patient's ECG information. The ECG electrodes 1322 can transmit information descriptive of the ECG signals to the sensor interface 1312 for subsequent analysis.

The heart vibrations sensors 1324 can detect a patient's heart vibration information. For example, the heart vibrations sensors 1324 can be configured to detect heart vibration values including any one or all of S1, S2, S3, and S4. From these heart vibration values, certain heart vibration metrics may be calculated, including any one or more of electromechanical activation time (EMAT), percentage of EMAT (% EMAT), systolic dysfunction index (SDI), and left ventricular systolic time (LVST). The heart vibrations sensors 1324 can include an acoustic sensor configured to detect vibrations from a subject's cardiac system and provide an output signal responsive to the detected heart vibrations. The heart vibrations sensors 1324 can also include a multi-channel accelerometer, for example, a three channel accelerometer configured to sense movement in each of three orthogonal axes such that patient movement/ body position can be detected and correlated to detected heart vibrations information. The heart vibrations sensors 1324 can transmit information descriptive of the heart vibrations information to the sensor interface 1312 for subsequent analysis.

The tissue fluid monitors 1326 can use radio frequency (RF) based techniques to assess fluid levels and accumulation in a patient's body tissue. For example, the tissue fluid monitors 1326 can be configured to measure fluid content in the lungs, typically for diagnosis and follow-up of pulmonary edema or lung congestion in heart failure patients. The tissue fluid monitors 1326 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 1326 can transmit information descriptive of the tissue fluid levels to the sensor interface 1312 for subsequent analysis.

The sensor interface 1312 can be coupled to any one or combination of sensing electrodes/other sensors to receive other patient data indicative of patient parameters. Once data from the sensors has been received by the sensor interface 1312, the data can be directed by the processor 1318 to an appropriate component within the medical device controller 1220. For example, if heart data is collected by heart vibrations sensor 1324 and transmitted to the sensor interface 1312, the sensor interface 1312 can transmit the data to the processor 1318 which, in turn, relays the data to a cardiac event detector. The cardiac event data can also be stored on the data storage 1304.

In certain implementations, the alarm manager 1314 can be configured to manage alarm profiles and notify one or more intended recipients of events specified within the alarm profiles as being of interest to the intended recipients. These intended recipients can include external entities such as users (patients, physicians, and monitoring personnel) as well as computer systems (monitoring systems or emergency response systems). The alarm manager 1314 can be implemented using hardware or a combination of hardware and software. For instance, in some examples, the alarm manager 1314 can be implemented as a software component that is stored within the data storage 1304 and executed by the processor 1318. In this example, the instructions included in the alarm manager 1314 can cause the processor 1318 to configure alarm profiles and notify intended recipients using the alarm profiles. In other examples, alarm manager 1314 can be an application-specific integrated circuit (ASIC) that is coupled to the processor 1318 and configured to manage alarm profiles and notify intended recipients using alarms specified within the alarm profiles. Thus, examples of alarm manager 1314 are not limited to a particular hardware or software implementation.

In some implementations, the processor 1318 includes one or more processors (or one or more processor cores) that each are configured to perform a series of instructions that result in manipulated data and/or control the operation of the other components of the medical device controller 1220. In some implementations, when executing a specific process (e.g., cardiac monitoring), the processor 1318 can be configured to make specific logic-based determinations based on input data received, and be further configured to provide one or more outputs that can be used to control or otherwise inform subsequent processing to be carried out by the processor 1318 and/or other processors or circuitry with which processor 1318 is communicatively coupled. Thus, the processor 1318 reacts to specific input stimulus in a specific way and generates a corresponding output based on that input stimulus. In some example cases, the processor 1318 can proceed through a sequence of logical transitions in which various internal register states and/or other bit cell states internal or external to the processor 1318 may be set to logic high or logic low. As referred to herein, the processor 1318 can be configured to execute a function where software is stored in a data store coupled to the processor 1318, the software being configured to cause the processor 1318 to proceed through a sequence of various logic decisions that result in the function being executed. The various components that are described herein as being executable by the processor 1318 can be implemented in various forms of specialized hardware, software, or a combination thereof. For example, the processor can be a digital signal processor (DSP) such as a 24-bit DSP processor. The processor can be a multi-core processor, e.g., having two or more processing cores. The processor can be an Advanced RISC Machine (ARM) processor such as a 32-bit ARM processor. The processor can execute an embedded operating system, and include services provided by the operating system that can be used for file system manipulation, display & audio generation, basic networking, firewalling, data encryption and communications.

In some embodiments, an ECG analysis system (e.g., arrhythmia monitoring system, heart failure status monitoring, and/or the like) may include ECG being acquired with a sensor on the body (e.g., external heart monitoring device, which may include ECG electrodes and/or ECG processing circuitry, as described herein). Additionally or alternatively, a neural net may process the ECG signal(s) to identify and flag reportable intervals (e.g., ECG signal portions associated with at least one predetermined rhythm change, as descried herein).

In some embodiments, a reportable event may include an ECG snippet (e.g., ECG signal portion), which may include a rhythm change from one rhythm type to another. Additionally or alternatively, the network (e.g., neural network) may identify the rhythm change without having to classify the specific rhythm type. For example, the network (e.g., neural network) may detect rhythm type change from normal sinus rhythm (NSR) to Atrial Fibrillation (AFIB), from AFIB to NSR, from AFIB to Atrial Flutter (AFL), etc. Additionally or alternatively, every time a rhythm change is identified, the ECG strip (e.g., ECG signal portion) containing the change may be marked and/or sent to a server (e.g., remote computer system, as described herein).

In some embodiments, a rhythm change can be of several different types, e.g., (1) an actual change from one clinical condition to another (NSR to AFib, AFib to ventricular tachycardia (VT), etc.), (2) a change in morphology RR-interval statistics or similar change in signal characteristics, and/or the like.

In some embodiments, an input to the neural network may be a vector of raw ECG samples taken during a time window. For example, the time window may be 15-120 seconds, 15-60 second, and/or the like. Additionally or alternatively, the output of the network may be the location of a rhythm change in the ECG strip (e.g., ECG signal portion, vector of ECG samples, and/or the like). In some embodiments, the neural network may be a deep convolutional neural network, recurrent network, attention network, and/or the like.

For example, the neural network may include the following parameters: (i) 7-10 convolutional layers; (ii) an input layer receiving 15-60 seconds of ECG sampled at 100-500 Hz, with overall 1500 to 30000 nodes at the input layer.

In some embodiments, the neural network may include multiple "Siamese" branches that handle multiple ECG channels (e.g., with shared or different parameters), and/or may include with additional layers that integrate these channels.

In some embodiments, the neural network may also integrate (e.g., take as input and/or the like) data from additional sensors, e.g., accelerometers, heart sounds, and/or the like.

In some embodiments, the neural network may detect ECG strips that are different in rhythm type from the patient's pre-acquired ECG baseline. For example, such a baseline may be pre-set to the network based on high accuracy ECG measurements in the clinic, may be automatically detected by the device (e.g., external heart monitoring device and/or the like) during known rest times (e.g. during night hours), and/or the like.

In some embodiments, the network (e.g., neural network) may provide confidence levels to each classifications. Additionally or alternatively, any decision may depend on both the confidence level and the classification (e.g., the device may decide to transmit events which the device is not able to classify with high enough confidence).

In some embodiments, the neural network may be implemented on one of the following:

(a) ECG sensor (e.g., external heart monitoring device): The neural network may be implemented using a specialized, low-power neural network (NN) processing hardware). For example, a specialized NN processor may implement the neural network directly in silicon (e.g., not using a general purpose Von-Neumann machine). This architecture may allow for implementing the neural network with very low power consumption. As such, the neural network may be integrated into the patient worn sensor, relying on a small battery.

(b) Gateway: The system may include a gateway device (e.g., a smartphone, an Android device, a table, a laptop, a portable and/or handheld device, and/or the like) that receives the raw data from the sensor, e.g. using Bluetooth (BT) transmission, and then sends that data to a remote server. The neural network may be implemented on this gateway.

(c) Server (e.g., remote computer system): A first layer of processing at the server-side can be used to reduce the amount of data to be processed in the next processing layers.

In some embodiments, the network (e.g., neural network) logic may be split across the ECG sensor (e.g., external heart monitoring device), the gateway, and/or the server (e.g., remote computer system) in such a way as to optimize power consumption, transmission limitations, other constraints, and/or the like while retaining the desired accuracy levels.

In some embodiments, in addition to the (first) neural network, the server may include a second neural network. For example, the second neural network may be larger, more accurate, and/or the like compared to the (first) neural network. Additionally or alternatively, the second neural network may also be capable of classifying the specific arrhythmia type.

In some embodiments, data transmission and processing may be significantly reduced by sending only the flagged intervals (e.g., ECG signal portions associated with at least one predetermined rhythm change) to the server analysis layers (e.g., remote computer system). Additionally or alternatively, only flagged intervals may be processed at the server for arrhythmia type classification and/or presented to technician for annotation.

In some embodiments, data reduction processing may also "hunt" for rare arrhythmia using non-NN processing (e.g., any suitable signal processing technique (e.g., separate from or including the second neural network)).

In some embodiments, a data reduction layer may "trickle" random strips (e.g., second ECG portions) to provide new annotated data for future algorithm training (e.g., training the first neural network, the second neural network, and/or the like). For example, trickling may be random, may be based on the network confidence, and/or may be based on other predefined rules. In some embodiments, such trickling may allow for enlarging the available annotated dataset that can be used for improving the network performance Additionally or alternatively, such trickling may allow for continued testing of the network (e.g., neural network) performance. For example, changes in the input distribution may affect the detection performance, and/or continued testing may be useful. As such, the system may include a trickling mechanism.

In some embodiments, the system may employ rhythm bucketing. For example, after strips (e.g., ECG signal portions) are flagged (e.g., determined to be associated with at least one predetermined rhythm change), such strips (e.g., ECG signal portions) may be bucketed (e.g., classified, categorized, grouped, clustered, and/or the like) into groups of similar strips, e.g., for batch review by a technician. For example, such bucketing may be accomplished by using a network (e.g., neural network), by commonality/similarity of features (e.g., vectors representations), and/or the like. In some embodiments, bucketing may be shown to technicians (e.g., using a dedicated user interface, such as a graphical user interface (GUI) and/or the like) to aid rapid human processing and interrogation (e.g., of the ECG signal portions in each bucket).

In some embodiments, Independent Diagnostic Testing Facility (IDTF) technicians may currently review every reported arrhythmia, and there may not be a great advantage to telling the technicians what the technicians are seeing (e.g., identifying a rhythm change, type of arrhythmia, and/or the like). In some embodiments, the amount of data displayed to such technicians may be reduced, e.g., to just identified/determined rhythm changes, am amount of data per patient may become more reasonable/manageable (e.g., an average of approximately 10 minutes per day). Additionally or alternatively, bucketing the events (e.g., ECG signal portions associated with and/or identified as containing at least one rhythm change) into classes may enable the technicians to review (e.g., classify, annotate, and/or the like) such events en-batch.

In some embodiments, a system (e.g., arrhythmia monitoring system, heart failure status monitoring system, and/or the like) may be part of an ECG ambulatory monitoring service that employs a group of ECG technicians for reviewing and analyzing ECG strips (e.g., ECG signal portions). Additionally or alternatively, such technicians may have different levels of experience and expertise.

In some embodiments, the system (e.g., arrhythmia monitoring system, heart failure status monitoring system, and/or the like) may monitor the output of the technicians' work and/or identifies inconsistencies. For example, if an inconsistency/anomaly is detected by the system, the relevant strip (e.g., ECG signal portion) may be routed to a senior technician (e.g., supervisor and/or the like) for additional review.

In some embodiments, the system (e.g., arrhythmia monitoring system, heart failure status monitoring system, and/or the like) may include and/or uses a deep learning network (e.g., neural network). In some embodiments, the network (e.g., neural network) may accepts the following inputs: (a) The current ECG strip e.g., ECG signal portion) under review. (b) The result of the ECG technician analysis (e.g., annotation data). The technician's ECG analysis (e.g., annotation data) may be in form of a text describing the rhythm (e.g., "normal sinus rhythm," "atrial fibrillation onset," etc.).

In some embodiments, the network output may include a numeric metric reflecting the plausibility of the decision, taking into account the body of previous decisions which were used for in the training phase.

In some embodiments, the system (e.g., neural network of the arrhythmia monitoring system, heart failure status monitoring system, and/or the like) may have a training stage (e.g., when system (e.g., the neural network of thereof) learns based on a training dataset) and a production stage (e.g., when the system (e.g., the neural network of thereof) is used to evaluate technicians' decisions online.

In some embodiments, for each technician, a different network (e.g., neural network) may be trained based only on other technicians decisions (e.g., to remove "self-persuasion").

In some embodiments, the system (e.g., arrhythmia monitoring system, heart failure status monitoring system, and/or the like) may be set to alert only when there is a deviation with high confidence (e.g., low plausibility).

In some embodiments, over time, conditions affecting the ECG input may change. For example, the characteristics of the populations of subjects may change, e.g., as new populations are indicated for ECG evaluation. Additionally or alternatively, hardware changes may occur over time. In some embodiments, based on this change over time, the performance of the neural network might deteriorate (e.g., accuracy and/or sensitivity may drop).

In some embodiments, the ECG technicians only review the ECG strips (e.g., ECG signal portions) that were detected by the network (e.g., neural network), so such technician may have no indication of this reduction in performance. In some embodiments, a trickling mechanism may be useful in order to detect such performance deterioration, enable performance improvement by generating a continual stream of annotated samples representing the change in conditions that may be used to improve the network, and/or the like.

In some embodiments with such a trickling mechanism, the technicians may be presented with some ECG strips (e.g., ECG signal portions) that where not flagged by the neural network for review (e.g., the "trickle").

In some embodiments, techniques of sampling strips (e.g., ECG signal portions) for review (e.g., generating the "trickle") may be (a) a low-percentage of the strips randomly sent for analysis, (b) a portion of those strips that are not noise/NSR or those that are different from some norm or those that are suspect of being rare arrhythmia events (blocks, etc.), (c) those strips which are flagged as low confidence by the neural network (e.g., using a special network for confidence prediction or other techniques such as clustering or nearest-neighbors).

In some embodiments, if the original performance of the neural network is preserved, the technician review of the "trickle" may be expected to yield only a low proportion of clinical findings, and/or the like. Additionally or alternatively, a deterioration in performance of the neural network may result in an increase in the clinical yield of the trickle. In some embodiments, this change may be monitored. For example, when such change is observed, a retraining may be initiated. In some embodiments, the retraining may utilize the new annotation done by the technicians on the "trickle" that has accumulated up to that point.

In some embodiments, the "trickle" may be used as input to a server-side supervising neural network, which may be tasked to detect a change in the distribution of the inputs.

In some embodiments, two different sensors (e.g., a first set of electrodes (e.g., of a first sensor device) and a second set of electrodes (e.g., of a second sensor device) separate from the first set of electrodes) may carry information on the same phenomenon. In some embodiments, the first sensor (e.g., with the first set of electrodes) may be more suitable for human interpretation, contain more information, have better quality, and/or the like (e.g., compared to the second sensor). Additionally or alternatively, the second sensor may allow (e.g., be suitable for) machine detection of the desired phenomenon at suitable performance, but the output of the second sensor may be unsuitable for human interpretation.

In some embodiments, an annotated reference (e.g., annotations associated with a historical collection of ECG signal portions) may be used for supervised learning. In some embodiments, to obtain such an annotated reference, two sensors may be deployed simultaneously on the subject (e.g., patient). For example, annotation data may be generated based on the first sensor (e.g., by human reviewers/technicians). Additionally or alternatively, the annotation data obtained may be used to train the network (e.g., neural network) using sensor data (e.g., ECG signals and/or samples thereof) from the second sensor. In some embodiments, e.g., if multiple leads or multiple sensors (e.g., wrist-watch, wearable patch, etc.) are available, one lead (e.g., a more reliable, accurate, suitable for human interpretation, and/or the like lead) may be used to annotate the data for the other lead (e.g., less reliable, accurate, suitable for human interpretation, and/or the like lead).

For example, a lead II ECG signal (e.g., the reference signal from a first sensor/set of electrodes) may be suitable for human AFIB detection and interpretation. Additionally or alternatively, a patch sensor may be positioned on the left axillary area (e.g., the target sensor/set or electrodes) may be less suitable for human AFIB detection, but may still carry relevant information that can be used by machine learning algorithms (e.g., neural networks). In some embodiments, an annotated reference database maybe generated using the lead II signal, and such database may be used to train the patch sensor.

In some embodiments, there may be situations in which the amount of data available for training the network may be small. For example, this may be due to (1) lack of enough recorded data, but where the recorded data is annotated, e.g., when a new sensor version is being used or a deployment method has changed and not enough data has yet been collected; (2) availability of enough recorded raw data, but lack of manual labels (e.g., due to time, budget, or expertise constraints)

In some embodiments, to address these problems, the following methods can be applied (e.g., individually or in tandem): (1) The network (e.g., neural network) may be trained for a different task for which enough data and annotation is available (e.g., to identity r-peaks or measure heart rate). The resulting network (e.g., neural network) may then be used for the target task and fine-tuned (e.g., using the limited annotated dataset). (2) Additionally or alternatively, a network (e.g., neural network) may be trained on data from a specific lead (e.g., for which a large amount of annotated data is available), and the trained model (e.g., neural network) may be applied to a target lead (e.g., for which a limited amount of annotated data is available). The base model (e.g., neural network) may be than fined-tuned for the target lead. (3) Additionally or alternatively, when manually labeled data is not available or is available in small quantities, training may utilize signal representations that are learned using a self-supervised proxy tasks on large amounts of unannotated data. These tasks can be, for example: (a) predicting the representation of the signal or the raw signal at different times in the future relative to the current strip (e.g., ECG signal portion), (b) training based on measuring prediction error or using contrastive loss that tries to differentiate between strips (e.g., ECG signal portions) that are more similar than others (e.g. based on their time distance from the predicted strip, them belonging to different patients, and/or the like), (c) predicting the relative time from which a short test strip (e.g., ECG signal portion) was taken relative to another strip, (d) predicting signal features such as heartrate (HR) for which there are other known algorithms.

In some embodiments, augmentation may be used to artificially enrich the annotated dataset for training. Such a method may be based on modifying (e.g., augmenting) the input signal in such a way that its labels are not modified or are modified in a known way.

For example, for ECG classification, the following augmentation methods may be used: (1) linear combinations of different leads (to simulate small differences in positioning of the leads, or extrapolate to unavailable leads); (2) time warping (e.g., signal dependent time dilations) to simulate slightly modified heart rates; (3) filtering (e.g. using short time Fourier transforms); (4) adding noise (e.g., typical and/or expected noise); (5) inversion of the signal; (6) Augmentation with style transfer (e.g., using "style transfer" and other methods to augment arrhythmia events (e.g., rare arrhythmia events) while retaining their arrhythmia and using them for training, which may be useful for training deep learning (DL) nets (e.g., neural network) in order to increase the effectiveness (e.g., amount) of data, which may allow projecting beat morphology onto different rhythms).

In some embodiments, the network (e.g., neural network) may accept the following inputs: (a) current ECG strip for detection/classification and/or (b) ECG context information. For example, the context information may include the following: (a) A baseline ECG strip (e.g., ECG signal portion) of the same patient. For example, such a strip may be from a time known or estimated to be normal (e.g., at sleep time, rest time, and/or the like) or to have some know characteristics. Such context may be the raw data (e.g., ECG signal portion) or some representation of it (e.g., a vector representation built (e.g., generated) by a neural network). (b) A representation of all or some of patient's measurements in the past that are aggregated as a reference (e.g., reference vector) for the current tested strip (e.g., current ECG signal portion). (c) Calibration measurements using high precision ECG (e.g., a 12-lead ECG in the clinic).

In some embodiments, the context data may include multiple time scales. For example, the network (e.g., neural network) may inspect ECG data over different time scales to determine a classification. Additionally or alternatively, the network (e.g., neural network) may integrate data over one or more time periods (e.g., a month, day, the current ECG strip (e.g., a 30-second ECG signal portion)) to take into account trends over time and patient specific baseline.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Embodiments disclosed herein may also be combined with one or more features, as well as complete systems, devices and/or methods, to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

As used herein, the terms "right", "left", "top", and derivatives thereof shall relate to the invention as it is oriented in the drawing figures. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

As used herein, the terms "communication" and "communicate" refer to the receipt or transfer of one or more signals, messages, commands, or other type of data. For one unit or component to be in communication with another unit or component means that the one unit or component is able to directly or indirectly receive data from and/or transmit data to the other unit or component. This can refer to a direct or indirect connection that can be wired and/or wireless in nature. Additionally, two units or components can be in communication with each other even though the data transmitted can be modified, processed, routed, and the like, between the first and second unit or component. For example, a first unit can be in communication with a second unit even though the first unit passively receives data, and does not actively transmit data to the second unit. As another example, a first unit can be in communication with a second unit if an intermediary unit processes data from one unit and transmits processed data to the second unit. It will be appreciated that numerous other arrangements are possible.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is currently claimed:

1. An arrhythmia monitoring system, comprising:
   an external heart monitoring device for a patient comprising:
   (a) a plurality of electrocardiogram (ECG) electrodes configured to sense surface ECG activity of the patient;
   (b) ECG processing circuitry configured to process the surface ECG activity of the patient to provide at least one ECG signal for the patient on at least one ECG channel;
   (c) a non-transitory computer-readable medium comprising a rhythm change classifier, the rhythm change classifier comprising at least one neural network trained based on a historical collection of a plurality of ECG signal portions with known rhythm change information; and (d) at least one processor operatively connected to the at least one ECG channel and the non-transitory computer-readable medium, the at least one processor configured to:
  (i) receive the at least one ECG signal received via the at least one ECG channel,
  (ii) detect, with the rhythm change classifier, time data corresponding to a predetermined rhythm change in the at least one ECG signal, the time data comprising at least one of a start time, a time interval, or any combination thereof,
  (iii) determine, based on the detected time data, at least one ECG signal portion associated with the detected time data corresponding to the predetermined rhythm change in the at least one ECG signal, and
  (iv) transmit the at least one determined ECG signal portion to a remote computer system,
wherein the at least one ECG channel comprises a plurality of ECG channels, wherein the at least one ECG signal comprises at least one respective ECG signal associated with each respective ECG channel of the plurality of ECG channels, wherein the plurality of ECG channels comprises a first ECG channel and a second ECG channel, wherein the at least one ECG signal comprises a first respective ECG signal associated with the first ECG channel and a second respective ECG signal associated with the second ECG channel, and wherein the first respective ECG signal is orthogonal to the second respective ECG signal.

2. The arrhythmia monitoring system of claim 1, further comprising:
at least one sensor and associated sensor circuitry configured to sense non-ECG biometric data of the patient,
wherein the processor is further configured to detect with the rhythm change classifier the predetermined rhythm change based on the at least one ECG signal and the non-ECG biometric data of the patient.

3. The arrhythmia monitoring system of claim 2, wherein the at least one sensor comprises at least one of an accelerometer, a heart sound detector, or a combination thereof, and wherein the non-ECG biometric data comprises at least one of acceleration data, heart sound data, or any combination thereof.

4. The arrhythmia monitoring system of claim 2, wherein the at least one ECG signal portion comprises an ECG signal portion having a duration greater than or equal to 15 seconds and less than or equal to 120 seconds.

5. The arrhythmia monitoring system of claim 2, wherein the at least one ECG signal comprises a plurality of ECG signal samples, and wherein the plurality of ECG signal samples are sampled at a rate greater than or equal to 100 Hz and less than or equal to 500 Hz.

6. The arrhythmia monitoring system of claim 2, wherein the external heart monitoring device comprises a wearable patch.

7. The arrhythmia monitoring system of claim 2, wherein the external heart monitoring device comprises a wearable cardioverter defibrillator.

8. The arrhythmia monitoring system of claim 1, wherein the remote computer system is in communication with the external heart monitoring device, the remote computer system configured to:
receive the at least one determined ECG signal portion from the external heart monitoring device, and
analyze the at least one determined ECG signal portion to classify a type of arrhythmia for the rhythm change in the at least one ECG signal.

9. The arrhythmia monitoring system of claim 8, wherein the remote computer system comprises an arrhythmia type classifier comprising at least one second neural network trained based on a second historical collection of a second plurality of ECG signal portions with known arrhythmia type information,
wherein analyzing the at least one determined ECG signal portion comprises detecting with the arrhythmia type classifier the type of arrhythmia associated with the rhythm change based on the at least one determined ECG signal portion.

10. The arrhythmia monitoring system of claim 8, wherein the processor is further configured to determine with the rhythm change classifier a confidence score associated with the predetermined rhythm change based on the at least one ECG signal.

11. The arrhythmia monitoring system of claim 8, wherein the external heart monitoring device comprises a wearable patch.

12. The arrhythmia monitoring system of claim 8, wherein the external heart monitoring device comprises a wearable cardioverter defibrillator.

13. An arrhythmia monitoring system, comprising:
an external heart monitoring device for a patient comprising:
  (a) a plurality of electrocardiogram (ECG) electrodes configured to sense surface ECG activity of the patient;
  (b) ECG processing circuitry configured to process the surface ECG activity of the patient to provide at least one ECG signal for the patient on at least one ECG channel;
  (c) a non-transitory computer-readable medium comprising a rhythm change classifier, the rhythm change classifier comprising at least one neural network trained based on a historical collection of a plurality of ECG signal portions with known rhythm change information; and
  (d) at least one processor operatively connected to the at least one ECG channel and the non-transitory computer-readable medium, the at least one processor configured to:
    (i) receive the at least one ECG signal received via the at least one ECG channel,
    (ii) detect, with the rhythm change classifier, time data corresponding to a predetermined rhythm change in the at least one ECG signal, the time data comprising at least one of a start time, a time interval, or any combination thereof,
    (iii) determine, based on the detected time data, at least one ECG signal portion associated with the detected time data corresponding to the predetermined rhythm change in the at least one ECG signal, and
    (iv) transmit the at least one determined ECG signal portion to a remote computer system,
wherein the at least one ECG channel comprises a plurality of ECG channels, wherein the at least one ECG signal comprises at least one respective ECG signal associated with each respective ECG channel of the plurality of ECG channels,
wherein the at least one neural network comprises a plurality of Siamese branches, each respective Siamese branch of the plurality of Siamese branches associated with a respective ECG channel of the plurality of ECG channels, and wherein the at least one neural network further comprises at least one further layer connected to the plurality of Siamese branches.

14. The arrhythmia monitoring system of claim 13, wherein each Siamese branch of the plurality of Siamese branches comprises a plurality of convolutional layers, wherein dimensions of each of the plurality of convolutional layers of each respective Siamese branch are the same as the dimensions of each of the plurality of convolutional layers of each other Siamese branch.

15. The arrhythmia monitoring system of claim 13, wherein the at least one neural network comprises at least one convolutional neural network having a plurality of convolutional layers, and wherein the plurality of convolutional layers comprises at least seven convolutional layers and no more than ten convolutional layers.

16. The arrhythmia monitoring system of claim 13, wherein the plurality of ECG channels comprises a first ECG channel and a second ECG channel, wherein the at least one ECG signal comprises a first respective ECG signal associated with the first ECG channel and a second respective ECG signal associated with the second ECG channel, and wherein the first respective ECG signal is orthogonal to the second respective ECG signal.

17. The arrhythmia monitoring system of claim 13, wherein the external heart monitoring device comprises a wearable patch.

18. The arrhythmia monitoring system of claim 13, wherein the external heart monitoring device comprises a wearable cardioverter defibrillator.

19. An arrhythmia monitoring system, comprising:
an external heart monitoring device for a patient comprising:
  (a) a plurality of electrocardiogram (ECG) electrodes configured to sense surface ECG activity of the patient;
  (b) ECG processing circuitry configured to process the surface ECG activity of the patient to provide at least one ECG signal for the patient on at least one ECG channel;
  (c) a non-transitory computer-readable medium comprising a rhythm change classifier, the rhythm change classifier comprising at least one neural network trained based on a historical collection of a plurality of ECG signal portions with known rhythm change information;
  (d) at least one processor operatively connected to the at least one ECG channel and the non-transitory computer-readable medium, the at least one processor configured to:
    (i) receive the at least one ECG signal received via the at least one ECG channel,
    (ii) detect, with the rhythm change classifier, time data corresponding to a predetermined rhythm change in the at least one ECG signal, the time data comprising at least one of a start time, a time interval, or any combination thereof,
    (iii) determine, based on the detected time data, at least one ECG signal portion associated with the detected time data corresponding to the predetermined rhythm change in the at least one ECG signal, and
    (iv) transmit the at least one determined ECG signal portion to a remote computer system; and at least one sensor and associated sensor circuitry configured to sense non-ECG biometric data of the patient, wherein the processor is further configured to detect with the rhythm change classifier the predetermined rhythm change based on the at least one ECG signal and the non-ECG biometric data of the patient, wherein detecting the predetermined rhythm change is further based on at least one of:
at least one baseline ECG signal portion of the patient;
at least one reference vector of the patient;
at least one calibration measurement of the patient, the at least one calibration measurement based on at least one second ECG signal from second surface ECG activity sensed by a second plurality of ECG electrodes, the second plurality of ECG electrodes independent of the plurality of ECG electrodes of the external heart monitoring device; or
at least one previous ECG signal portion.

20. The arrhythmia monitoring system of claim 19, wherein the external heart monitoring device comprises a wearable patch.

21. The arrhythmia monitoring system of claim 19, wherein the external heart monitoring device comprises a wearable cardioverter defibrillator.

22. The arrhythmia monitoring system of claim 19, wherein the at least one sensor comprises at least one of an accelerometer, a heart sound detector, or a combination thereof, and wherein the non-ECG biometric data comprises at least one of acceleration data, heart sound data, or any combination thereof.

23. An arrhythmia detection system, comprising:
  (a) a non-transitory computer-readable medium comprising an arrhythmia type classifier comprising at least one neural network trained based on a historical collection of a plurality of ECG signal portions with known arrhythmia type information; and
  (b) at least one processor operatively connected to the non-transitory computer readable medium, the at least one processor configured to:
    (i) receive at least one ECG signal and annotation data associated with at least one annotation for each of the at least one ECG signal,
    (ii) detect, with the arrhythmia type classifier, a type of arrhythmia in the at least one ECG signal and time data associated with the detected type of arrhythmia, the time data comprising at least one of a start time, a time interval, or any combination thereof,
    (iii) determine, based on the time data, at least one ECG signal portion associated with the detected type of arrhythmia in the at least one ECG signal,
    (iv) determine a plausibility score for the at least one annotation based on the detected type of arrhythmia,
    (v) generate at least one message based on the at least one determined ECG signal portion and the plausibility score for the at least one annotation, wherein the at least one message indicates at least one of:
      a recommendation to annotate the at least one determined ECG signal portion based on the detected type of arrhythmia, or
      a recommendation to reevaluate the annotation data associated with the at least one determined ECG signal portion based on the plausibility score, and
    (vi) transmit the at least one message associated with the at least one determined ECG signal portion.

24. The arrhythmia detection system of claim 23, wherein the known arrhythmia type information comprises a plurality of annotations, each annotation of the plurality of annotations associated with a respective ECG signal portion of the plurality of ECG signal portions,
wherein the arrhythmia type classifier is trained based on the plurality of ECG signals and the plurality of annotations.

25. The arrhythmia detection system of claim 23, wherein the historical collection of the plurality of ECG signal portions comprises a first plurality of ECG signal portions associated with at least one first ECG electrode and a second plurality of ECG signal portions associated with at least one second ECG electrode, wherein each respective ECG signal portion of the second plurality of ECG signal portions corresponds to a respective ECG signal portion of the first plurality of ECG signal portions,
wherein the known arrhythmia type information comprises a plurality of annotations, each respective annotation of the plurality of annotations associated with a respective ECG signal portion of the first plurality of ECG signal portions,
wherein the arrhythmia type classifier is trained by:
predicting with the arrhythmia type classifier a predicted type of arrhythmia in each respective ECG signal portion of the second plurality of ECG signal portions,
determining at least one error value based on the predicted type of arrhythmia and the respective annotation of the plurality of annotations associated with a respective ECG signal portion of the first plurality of ECG signal portions corresponding to the respective ECG signal portion of the second plurality of ECG signal portions, and
training the arrhythmia type classifier based on the at least one error value.

26. The arrhythmia detection system of claim 23, wherein the historical collection of the plurality of ECG signal portions comprises a first plurality of ECG signal portions of at least one first ECG signal based on first surface ECG activity sensed by at least one first ECG electrode and a second plurality of ECG signal portions of at least one second ECG signal based on second surface ECG activity sensed by at least one second ECG electrode, the at least one second ECG electrode independent of the at least one first ECG electrode,
wherein each ECG signal portion of the first plurality of ECG signal portions is combined with a respective ECG signal portion of the second plurality of ECG signal portions to form a plurality of extrapolated ECG signal portion,
wherein the known arrhythmia type information comprises a plurality of annotations, each respective annotation of the plurality of annotations associated with a respective extrapolated ECG signal portion of the plurality of extrapolated ECG signal portions.

* * * * *